United States Patent
Dowling et al.

(10) Patent No.: US 12,268,739 B2
(45) Date of Patent: Apr. 8, 2025

(54) USE OF TOLL-LIKE RECEPTOR 2 (TLR-2) AGONIST FOR MODULATING HUMAN IMMUNE RESPONSE

(71) Applicants: Children's Medical Center Corporation, Boston, MA (US); Dana-Farber Cancer Institute, Inc., Boston, MA (US)

(72) Inventors: David J. Dowling, Brighton, MA (US); Ofer Levy, Cambridge, MA (US); Francesco Borriello, Jamaica Plain, MA (US); David A. Scott, Newton, MA (US); Spencer E. Brightman, San Diego, CA (US)

(73) Assignees: Children's Medical Center Corporation, Boston, MA (US); Dana-Farber Cancer Institute, Inc., Boston, MA (US)

( * ) Notice: Subject to any disclaimer, the term of this patent is extended or adjusted under 35 U.S.C. 154(b) by 903 days.

(21) Appl. No.: 17/263,515

(22) PCT Filed: Jul. 26, 2019

(86) PCT No.: PCT/US2019/043656
§ 371 (c)(1),
(2) Date: Jan. 26, 2021

(87) PCT Pub. No.: WO2020/023872
PCT Pub. Date: Jan. 30, 2020

(65) Prior Publication Data
US 2021/0236632 A1 Aug. 5, 2021
US 2022/0118085 A9 Apr. 21, 2022
US 2023/0132397 A9 Apr. 27, 2023

Related U.S. Application Data

(60) Provisional application No. 62/711,450, filed on Jul. 27, 2018.

(51) Int. Cl.
*A61K 39/39* (2006.01)
*A61K 31/381* (2006.01)
(Continued)

(52) U.S. Cl.
CPC .......... *A61K 39/39* (2013.01); *A61K 31/381* (2013.01); *A61K 31/4025* (2013.01);
(Continued)

(58) Field of Classification Search
None
See application file for complete search history.

(56) References Cited

U.S. PATENT DOCUMENTS

2007/0275962 A1* 11/2007 Koul .................... C07D 493/04
514/408
2010/0297165 A1   11/2010 Berzofsky et al.
(Continued)

FOREIGN PATENT DOCUMENTS

WO   WO 2005/033102 A2   4/2005
WO   WO 2017/102703 A1   6/2017

OTHER PUBLICATIONS

Guan, The Journal of Biological Chemistry vol. 285, No. 31, pp. 23755-23762 Jul. 30, 2010. (Year: 2010).*
(Continued)

*Primary Examiner* — Layla D Berry
(74) *Attorney, Agent, or Firm* — Wolf, Greenfield & Sacks, P.C.

(57) ABSTRACT

Provided herein are Toll-like receptor 2 (TLR2) agonists for use in enhancing human immune response and/or as adjuvants in vaccines. The TLR2 agonists include thiophenes, imidazoles, or phenyl-containing compounds, which may be compounds of Formulae (I), (II), (III), and pharmaceutically acceptable salts, solvates, hydrates, polymorphs, co-crystals, tautomers, stereoisomers, isotopically labeled derivatives, prodrugs, and compositions thereof. The compounds described herein are used as enhancers of an immune response (e.g., innate and/or adaptive immune response), and are useful in treating and/or preventing a disease, as adjuvants in a vaccine for the disease. (e.g., proliferative disease, inflammatory disease, autoimmune disease, infectious disease, or chronic disease). Also provided in the present disclosure are pharmaceutical compositions, kits, methods, and uses including or using a compound described herein.

(Continued)

-continued

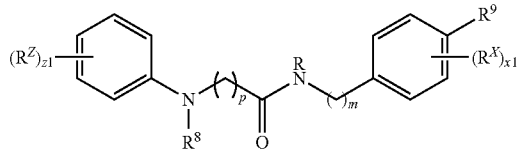

(III)

18 Claims, 14 Drawing Sheets

(51) Int. Cl.

| | | |
|---|---|---|
| *A61K 31/4025* | (2006.01) | |
| *A61K 31/438* | (2006.01) | |
| *A61K 31/4535* | (2006.01) | |
| *A61K 31/496* | (2006.01) | |
| *A61K 31/739* | (2006.01) | |
| *A61K 39/00* | (2006.01) | |
| *A61K 45/06* | (2006.01) | |
| *A61P 37/04* | (2006.01) | |
| *A61K 31/18* | (2006.01) | |
| *A61K 31/4164* | (2006.01) | |

(52) U.S. Cl.
CPC ........ *A61K 31/438* (2013.01); *A61K 31/4535* (2013.01); *A61K 31/496* (2013.01); *A61K 31/739* (2013.01); *A61K 45/06* (2013.01); *A61P 37/04* (2018.01); *A61K 31/18* (2013.01); *A61K 31/4164* (2013.01); *A61K 2039/55505* (2013.01); *A61K 2039/55511* (2013.01); *A61K 2039/55555* (2013.01); *A61K 2039/55566* (2013.01); *A61K 2039/55572* (2013.01); *A61K 2039/572* (2013.01); *A61K 2039/575* (2013.01); *C12N 2760/16134* (2013.01); *C12N 2760/16234* (2013.01)

(56) References Cited

U.S. PATENT DOCUMENTS

| | | |
|---|---|---|
| 2013/0065861 A1 | 3/2013 | Wu et al. |
| 2017/0072044 A1 | 3/2017 | Mills et al. |

OTHER PUBLICATIONS

Duthie, Immunol Rev. Jan. 2011: 239(1): 178-196. (Year: 2011).*
Borriello et al., Identification and Characterization of Stimulator of Interferon Genes As a Robust Adjuvant Target for Early Life Immunization. Front Immunol. Dec. 12, 2017;8:1772. doi: 10.3389/fimmu.2017.01772.
Cheng et al., Specific activation of the TLR1-TLR2 heterodimer by small-molecule agonists. Sci Adv. 2015;1(3):e1400139. doi: 10.1126/sciadv.1400139.
Guan et al., Identification of novel synthetic toll-like receptor 2 agonists by high throughput screening. J Biol Chem. Jul. 30, 2010;285(31):23755-62. doi: 10.1074/jbc.M110.116046. Epub May 26, 2010.
Murgueitio et al., Enhanced immunostimulatory activity of in silico discovered agonists of Toll-like receptor 2 (TLR2). Biochim Biophys Acta Gen Subj. Nov. 2017;1861(11 Pt A):2680-2689. doi: 10.1016/j.bbagen.2017.07.011. Epub Jul. 19, 2017.

* cited by examiner

| Levy lab ID | Plate | Well | Reagent Vendor/Library | Vendor Reagent ID | Molecular Formula | Compound SMILES | Molecular Weight | PubChem CIDs | Screened Count (including current BCH ADP screen) | Screen Positives Count (including current BCH ADP screen) |
|---|---|---|---|---|---|---|---|---|---|---|
| 004 | 1606 | E19 | ChemBridge3 | 9047153 | C19H26N2O5S | COC(=O)c1c(NC(=O)CN2CCC3(OCCO3)CC2)sc2CCCCc12 | 394.5 | 6466680 | 134 | 3 |
| 070 | 656 | D21 | ChemDiv1 (Combilab and International) | 4333-3837 | C20H24N2O4S2 | CCOC(=O)c1c(NC(=S)Nc2cccc2OC)sc2OC(C)(C)Cc12 | 420.5.5 | 1330660 | 59 | 1 |
| 080 | 3522 | E02 | ChemDiv Targeted Diversity Library | G839-0037 | C18H21N3O4S2 | c1(NC(=O)c(cc2)ccc2S(=O)(=O)N(C)C)sc(c3c1C(NC)=O)CCC3 | 407.51 | 7474989 | 39 | 1 |

FIG. 2

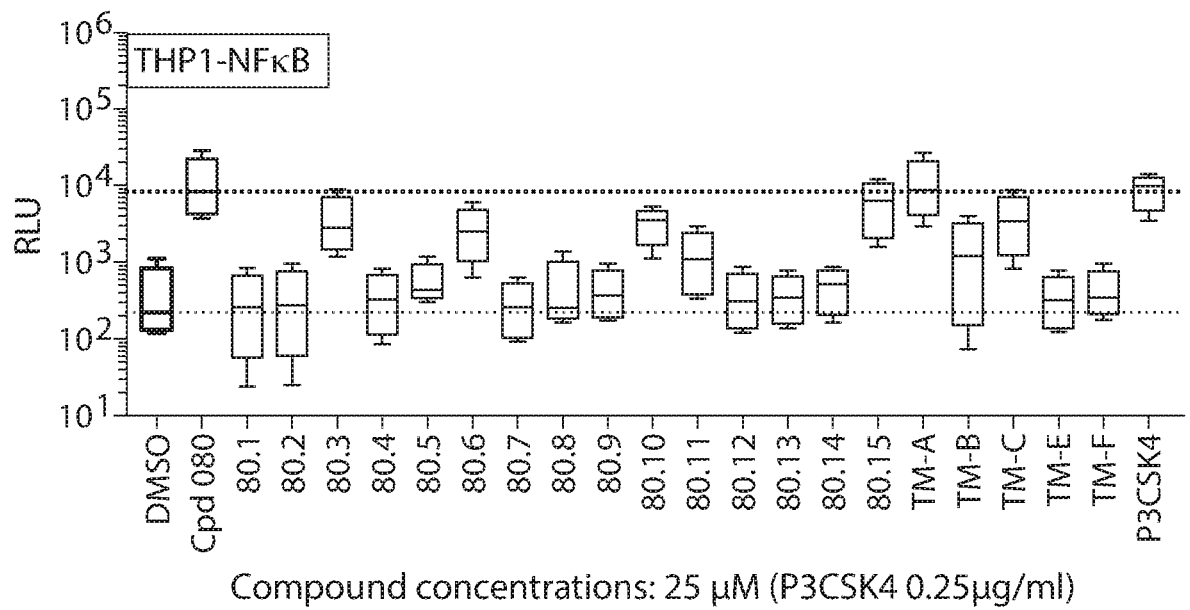
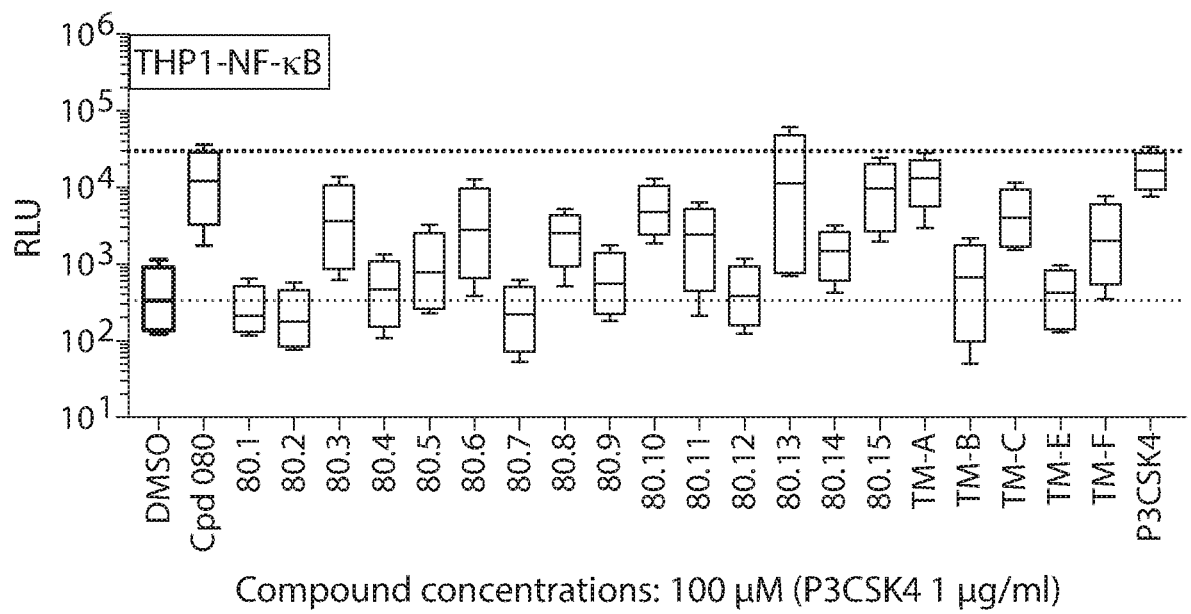
FIG. 8

USE OF TOLL-LIKE RECEPTOR 2 (TLR-2) AGONIST FOR MODULATING HUMAN IMMUNE RESPONSE

RELATED APPLICATIONS

This application is a national stage filing under 35 U.S.C. § 371 of international application number PCT/US2019/043656, filed Jul. 26, 2019, which claims the benefit under 35 U.S.C. § 119 (e) to U.S. Provisional Application No. 62/711,450, filed Jul. 27, 2018, and entitled "USE OF TOLL-LIKE RECEPTOR 2 (TLR-2) AGONIST FOR MODULATING HUMAN IMMUNE RESPONSE," the entire contents of each of which are incorporated herein by reference.

GOVERNMENT SUPPORT

This invention was made with government support under contract number HHSN272201400052C awarded by the National Institutes of Health. The government has certain rights in this invention.

BACKGROUND

Human immunity is crucial to both health and illness, playing key roles in multiple major diseases including infectious diseases, allergy, and cancer. Animal and human studies suggest that certain small molecules act as immune activators.

SUMMARY

Provided herein are Toll-like receptor 2 (TLR2) agonists for use in enhancing human immune responses. Therapeutic and/or prophylactic use of the TLR2 agonist (e.g., thiophene compound) are described. In some embodiments, the Toll-like receptor 2 (TLR2) agonists are used alone as immune-enhancing agents. In some embodiments, the Toll-like receptor 2 (TLR2) agonists are used as adjuvants in compositions including a vaccine for a disease, e.g., proliferative disease, inflammatory disease, autoimmune disease, infectious disease, or chronic disease, in a subject in need thereof. Adjuvants can enhance, prolong, and modulate immune responses to vaccinal antigens to maximize protective immunity. In some embodiments, using Toll-like receptor 2 (TLR2) agonists as vaccine adjuvants enable effective immunization in vulnerable populations (e.g., neonates, the elderly, or immunocompromised individuals). In some embodiments, the Toll-like receptor 2 (TLR2) agonists enhance both innate and adaptive immune response.

Some aspects of the present disclosure provide compositions comprising an antigen and a Toll-like receptor 2 (TLR2) agonist. In some embodiments, the antigen comprises a protein or polypeptide. In some embodiments, the antigen comprises a nucleic acid encoding a protein or a polypeptide. In some embodiments, the nucleic acid is DNA or RNA.

In some embodiments, the antigen is from a microbial pathogen. In some embodiments, the microbial pathogen is a bacterium, *mycobacterium*, fungus, virus, parasite, or prion. In some embodiments, the bacterium is *Bacillus anthracis, Bordetella pertussis, Corynebacterium diphtheriae, Clostridium tetani, Haemophilus influenzae* type b, pneumococcus, Staphylococci spp., *Mycobacterium tuberculosis, Neiserria meningitidis, Salmonella typhi, Vibrio cholerae,* or *Yersinia pestis*. In some embodiments, the virus is adenovirus, enterovirus such as poliomyelitis, dengue virus, Ebola virus, herpes viruses such as herpes simplex virus, cytomegalovirus and varicella-zoster, measles, mumps, rubella, hepatitis A virus, hepatitis B virus, hepatitis C virus, human papilloma virus, Influenza virus, rabies, Japanese encephalitis, rotavirus, human immunodeficiency virus (HIV), respiratory syncytial virus (RSV), smallpox, yellow fever, dengue virus, or Zika virus. In some embodiments, the parasite is *Plasmodium* spp., *Leishmania*, or a helminth. In some embodiments, the fungus is *Candida* spp., *Aspergillus* spp., *Cryptococcus* spp., *Mucormycete, Blastomyces dermatitidis, Histoplasma capsulatum*, or *Sporothrix schenckii*.

In some embodiments, the antigen is a cancer-specific antigen. In some embodiments, the antigen is a heteroclitic epitope or a cryptic epitope derived from the cancer-specific antigen. In some embodiments, the cancer-specific antigen is a neoantigen.

In some embodiments, the antigen comprises a lipopolysaccharide (LPS).

In some embodiments, the TLR2 agonist is conjugated to the antigen. In some embodiments, the TLR2 agonist is not conjugated to the antigen.

In some embodiments, the composition further comprises a pharmaceutically acceptable carrier.

In some embodiments, the composition is a vaccine composition. In some embodiments, the TLR2 agonist is an adjuvant. In some embodiments, the antigen is adsorbed onto alum. In some embodiments, the TLR2 agonist is adsorbed onto alum.

In some embodiments, the vaccine composition further comprises a second adjuvant. In some embodiments, second adjuvant is an agonist of a Pattern Recognition Receptor (PRR). In some embodiments, the PRR is selected from the group consisting of toll-like receptors (TLRs), NOD-like receptors (NLRs), RIG-I-like receptor (RLR), C-type Lectin receptors (CLRs), and a stimulator of interferon genes (STING). In some embodiments, second adjuvant is bound to or adsorbed to alum. In some embodiments, the second adjuvant is alum. In some embodiments, the second adjuvant is an emulsion.

In some embodiments, the TLR2 agonist is lipidated.

In some embodiments, the TLR2 agonist is a thiophene, an imidazole, or a phenyl-containing compound. In some embodiments, the thiophene comprises a compound of Formula (I), (II), (III), and a pharmaceutically acceptable salt, solvate, hydrates, polymorph, co-crystal, tautomer, stereoisomer, isotopically labeled derivative, or prodrug, thereof. In some embodiments, the thiophene comprises a compound of Formula (I), (II), (III), and a pharmaceutically acceptable salt thereof. In some embodiments, the thiophene comprises a compound of Formula (I):

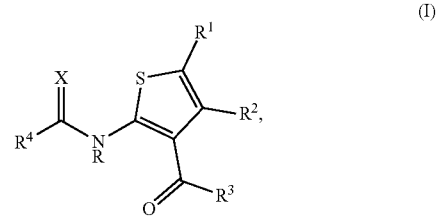

or a pharmaceutically acceptable salt thereof, wherein:
R¹ is hydrogen or optionally substituted alkyl;
R² is hydrogen or optionally substituted alkyl; or optionally, R¹ and R² are joined together with the intervening atoms to form a substituted or unsubstituted carbocyclic ring, substituted or unsubstituted heterocyclic ring, substituted or unsubstituted aryl ring, or substituted or unsubstituted heteroaryl ring;
R³ is hydrogen, halogen, optionally substituted alkyl, —OR$^{a1}$, or —N(R$^{a2}$)$_2$, wherein R$^{a1}$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group when attached to an oxygen atom;
wherein each occurrence of R$^{a2}$ is independently hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group;
R is hydrogen or optionally substituted alkyl;
X is O or S;
R⁴ is hydrogen, optionally substituted alkyl, optionally substituted carbocyclyl, optionally substituted heterocyclyl, optionally substituted aryl, optionally substituted heteroaryl, or —N(R$^{a2}$)$_2$.

In some embodiments, the compound is of Formula (IA):

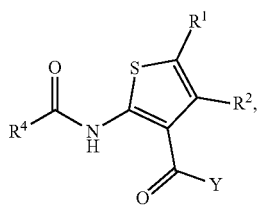

(IA)

or a pharmaceutically acceptable salt thereof, wherein:
R¹ and R² are joined together with the intervening atoms to form a substituted or unsubstituted carbocyclic ring, substituted or unsubstituted heterocyclic ring, substituted or unsubstituted aryl ring, or substituted or unsubstituted heteroaryl ring;
Y is —OR$^{a1}$, or —N(R$^{a2}$)$_2$, wherein R$^{a1}$ is optionally substituted C$_{1-6}$ alkyl; and each occurrence of R$^{a2}$ is independently hydrogen or optionally substituted C$_{1-6}$ alkyl.

A31. The composition of claim A30, wherein R¹ and R² are joined together with the intervening atoms to form a 5-membered carbocyclic ring, 6-membered carbocyclic ring, or 7-membered carbocyclic ring.

In some embodiments, R¹ and R² are joined together with the intervening atoms to form a 6-membered heterocyclic ring containing one nitrogen.

In some embodiments, the compound is of the formula:

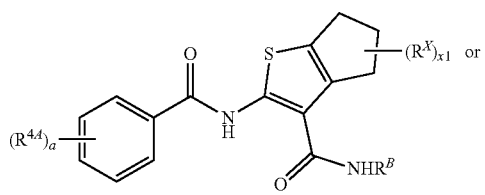

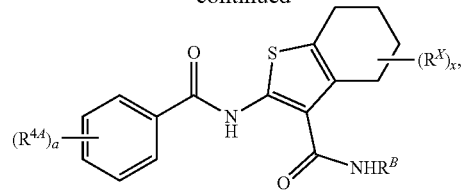

or a pharmaceutically acceptable salt thereof, wherein:
R$^{4A}$ is halogen, optionally substituted alkyl, optionally substituted acyl, —SO$_2$N(R$^a$)$_2$, —OR$^b$, optionally substituted alkenyl, optionally substituted alkynyl, optionally substituted carbocyclyl, optionally substituted heterocyclyl, optionally substituted aryl, optionally substituted heteroaryl;
each instance of RX is independently hydrogen, halogen, or optionally substituted alkyl;
R$^B$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, or optionally substituted heteroaryl;
x is 0, 1, 2, 3, 4, 5, or 6;
x1 is 0, 1, 2, 3, 4, 5, or 6;
a is 0, 1, 2, 3, 4, or 5;
each instance of R$^a$ is independently hydrogen, optionally substituted alkyl, a nitrogen protecting group, or two instances of R$^a$ are joined together with the intervening atoms to form optionally substituted heterocyclyl; and
R$^b$ is hydrogen, optionally substituted alkyl, or an oxygen protecting group.

In some embodiments, the compound is of the formula:

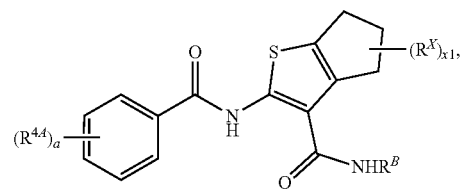

or a pharmaceutically acceptable salt thereof, wherein:
R$^{4A}$ is optionally substituted alkyl, optionally substituted acyl, —SO$_2$N(R$^a$)$_2$, optionally substituted alkenyl, optionally substituted alkynyl, optionally substituted carbocyclyl, optionally substituted heterocyclyl, optionally substituted aryl, optionally substituted heteroaryl;
each instance of RX is independently hydrogen, halogen, or optionally substituted alkyl;
R$^B$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, or optionally substituted heteroaryl;
x1 is 0, 1, 2, 3, 4, 5, or 6;
a is 0, 1, 2, 3, 4, or 5; and
each instance of R$^a$ is independently hydrogen, optionally substituted alkyl, or a nitrogen protecting group.

In some embodiments, at least one instance of R$^{4A}$ is —SO$_2$N(R$^a$)$_2$, or —C(=O)R$^a$, wherein each instance of $R^a$ is independently hydrogen, optionally substituted alkyl, or a nitrogen protecting group.

In some embodiments, the compound is of the formula:

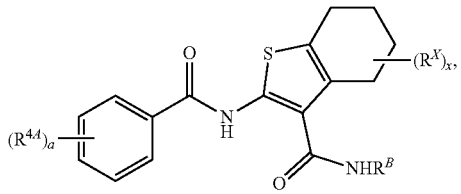

or a pharmaceutically acceptable salt thereof, wherein:
- $R^{4A}$ is optionally substituted alkyl, optionally substituted acyl, —$SO_2N(R^a)_2$, optionally substituted alkenyl, optionally substituted alkynyl, optionally substituted carbocyclyl, optionally substituted heterocyclyl, optionally substituted aryl, optionally substituted heteroaryl;
- each instance of RX is independently hydrogen, halogen, or optionally substituted alkyl;
- $R^B$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, or optionally substituted heteroaryl;
- x is 0, 1, 2, 3, 4, 5, or 6;
- a is 0, 1, 2, 3, 4, or 5; and
- each instance of $R^a$ is independently hydrogen, optionally substituted alkyl, a nitrogen protecting group, or two instances of $R^a$ are joined together with the intervening atoms to form optionally substituted heterocyclyl.

In some embodiments, $R^{4A}$ is —$SO_2N(R^a)_2$, and two instances of $R^a$ are joined together with the intervening atoms to form optionally substituted, 5-membered heterocyclyl or optionally substituted, 6-membered heterocyclyl.

In some embodiments, two instances of $R^a$ are joined together with the intervening atoms to form optionally substituted, 5-membered heterocyclyl.

In some embodiments, two instances of $R^a$ are joined together with the intervening atoms to form optionally substituted pyrrolidinyl.

In some embodiments, $R^1$ is optionally substituted $C_{1-6}$ alkyl; and $R^2$ is optionally substituted $C_{1-6}$ alkyl.

In some embodiments, $R^4$ is optionally substituted $C_{1-6}$ alkyl, optionally substituted 5-membered heteroaryl, or optionally substituted phenyl.

In some embodiments, the compound is of Formula (IB):

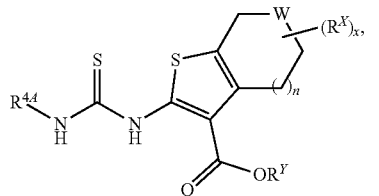

or a pharmaceutically acceptable salt thereof, wherein:
- W is —$C(R^{a1})$—, —$N(R^{a2})$—, or —O—, wherein $R^{a1}$ is hydrogen, halogen, or optionally substituted alkyl;
- each instance of RX is independently hydrogen, halogen, or optionally substituted alkyl;
- x is 0, 1, 2, 3, 4, 5, or 6;
- n is 0 or 1;
- $R^Y$ is hydrogen or optionally substituted $C_{1-6}$ alkyl; and
- $R^{4A}$ is hydrogen, optionally substituted $C_{1-6}$ alkyl, optionally substituted carbocyclyl, optionally substituted heterocyclyl, or optionally substituted aryl.

In some embodiments, W is —CH— and n is 0. In some embodiments, W is —CH— and n is 1. In some embodiments, W is —O— and n is 1. In some embodiments, W is —N(optionally substituted acyl)- and n is 1. In some embodiments, W is —N(optionally substituted alkyl)- and n is 1.

In some embodiments, $R^{4A}$ is optionally substituted phenyl or

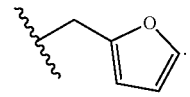 [SMILES: *Cc1ccco1]

In some embodiments, the compound is of the formula:

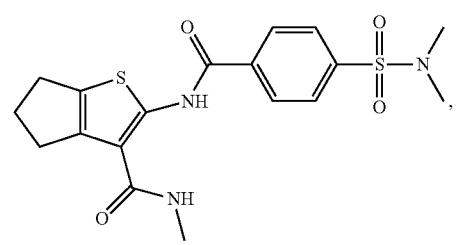
(80)

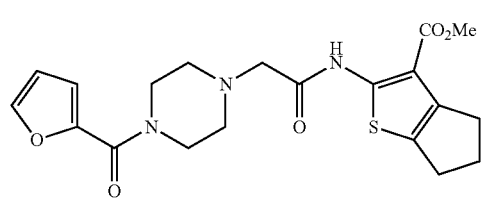
(3)

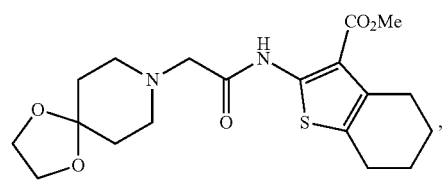
(4)

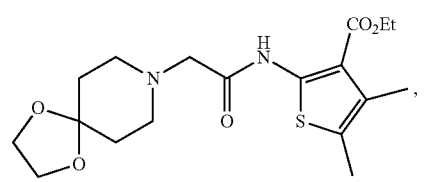
(5)

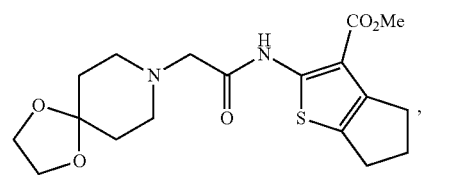
(004.19)

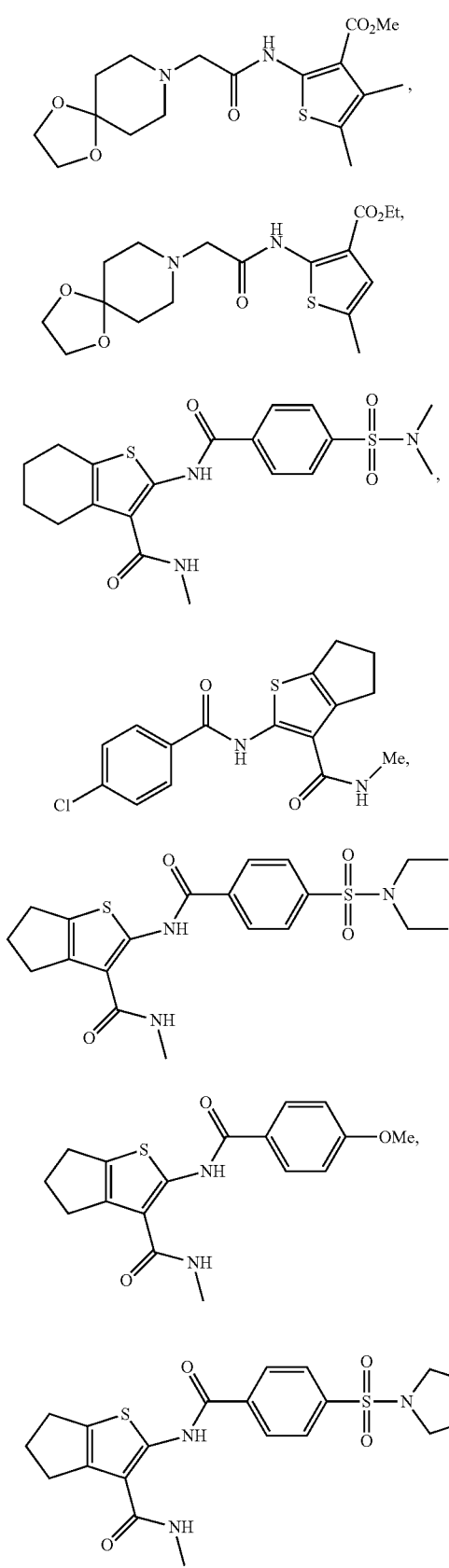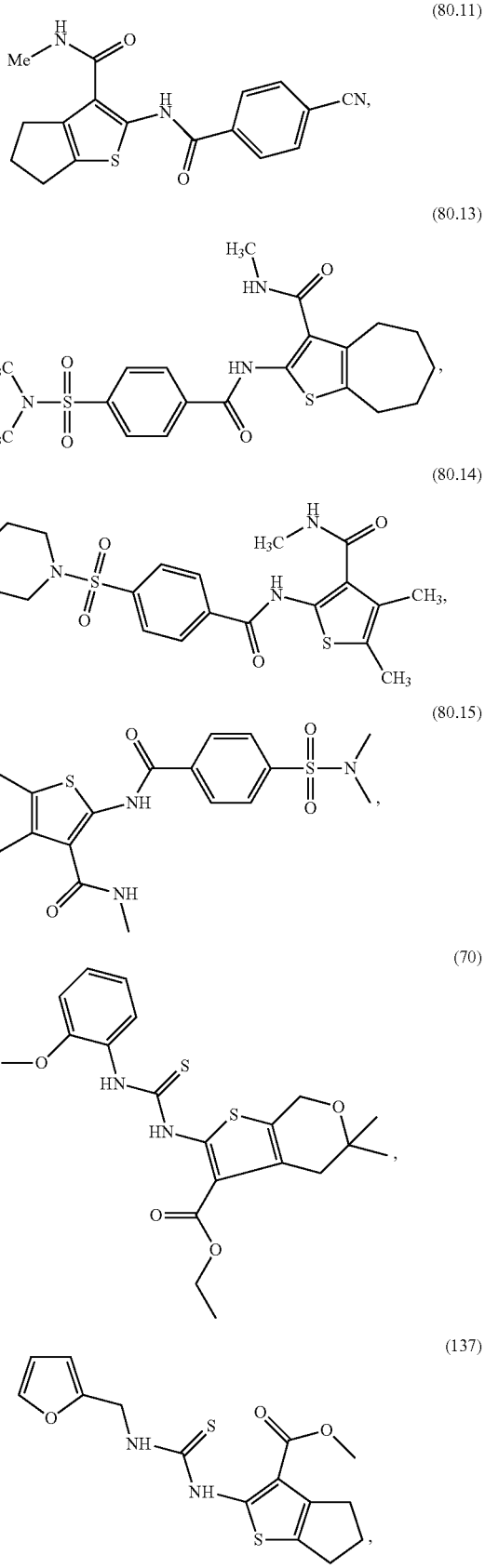

-continued

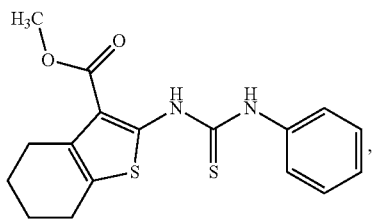
(TM-B)

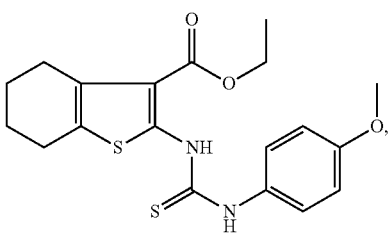
(TM-C)

or a pharmaceutically acceptable salt thereof.

In some embodiments, the compound is of Formula (II):

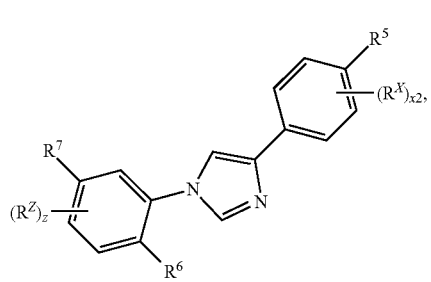
(II)

or a pharmaceutically acceptable salt thereof, wherein:
R$^5$ is hydrogen, halogen, optionally substituted alkyl, —NO$_2$, —OR$^{a1}$, or —N(R$^{a2}$)$_2$, wherein R$^{a1}$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group when attached to an oxygen atom;
wherein each occurrence of R$^{a2}$ is independently hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group;
each instance of RX is independently hydrogen, halogen, or optionally substituted alkyl;
x2 is 0, 1, 2, 3, or 4;
each instance of R$^6$ is independently hydrogen, optionally substituted acyl, optionally substituted alkyl, optionally substituted alkenyl, optionally substituted alkynyl, optionally substituted carbocyclyl, optionally substituted heterocyclyl, optionally substituted aryl, or —N(R$^{6A}$)$_2$;
each instance of R$^{6A}$ is independently hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group;
R$^7$ is hydrogen, halogen, optionally substituted alkyl, —NO$_2$, —OR$^{a1}$, or —N(R$^{a2}$)$_2$;
each instance of R$^Z$ is independently hydrogen, halogen, or optionally substituted alkyl; and
z is 0, 1, 2, or 3.

In some embodiments, R$^5$ is -NO$_2$. In some embodiments, R$^6$ is —N(R$^{6A}$)$_2$, and one instance of R$^{6A}$ is hydrogen and the other instance of R$^{6A}$ is optionally substituted C$_{1-6}$ alkyl. In some embodiments, R$^7$ is -NO$_2$.

In some embodiments, the compound is of the formula:

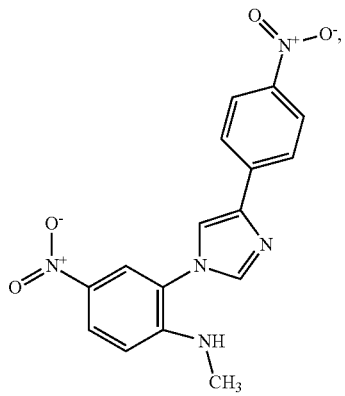
(TM-A)

or a pharmaceutically acceptable salt thereof.

In some embodiments, the compound is of Formula (III):

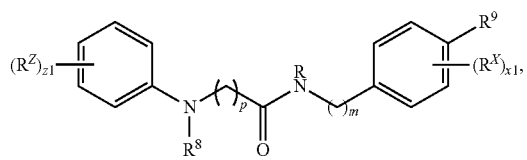
(III)

or a pharmaceutically acceptable salt thereof, wherein:
each instance of R$^Z$ is independently hydrogen, halogen, optionally substituted acyl, optionally substituted alkyl, —OR$^{a1}$, or —N(R$^{a2}$)$_2$, wherein R$^{a1}$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group when attached to an oxygen atom;
wherein each occurrence of R$^{a2}$ is independently hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group; and
m is 0 or 1;
p is 0 or 1;
z1 is 0, 1, 2, 3, 4, or 5;
each instance of RX is independently hydrogen, halogen, or optionally substituted alkyl;

x1 is 0, 1, 2, 3, or 4;

R is hydrogen or optionally substituted alkyl;

$R^8$ is hydrogen, optionally substituted alkyl, or —SO$_2$ ($R^{8A}$);

$R^{8A}$ is hydrogen, optionally substituted alkyl, optionally substituted carbocyclyl, optionally substituted heterocyclyl, or optionally substituted aryl; and $R^9$ is hydrogen, halogen, optionally substituted alkyl, —OR$^{a1}$, —N(R$^{a2}$)$_2$, or —SO$_2$N(R$^{a2}$)$_2$.

In some embodiments, m is 0 and p is 0. In some embodiments, m is 1 and p is 1. In some embodiments, $R^Z$ is halogen or optionally substituted alkyl. In some embodiments, $R^8$ is —SO$_2$ (R$^{8A}$), and $R^{8A}$ is optionally substituted $C_{1-6}$ alkyl or optionally substituted phenyl. In some embodiments, $R^9$ is halogen or —O (optionally substituted $C_{1-6}$ alkyl). In some embodiments, $R^9$ is —SO$_2$N (Me)$_2$.

In some embodiments, the compound is of the formula:

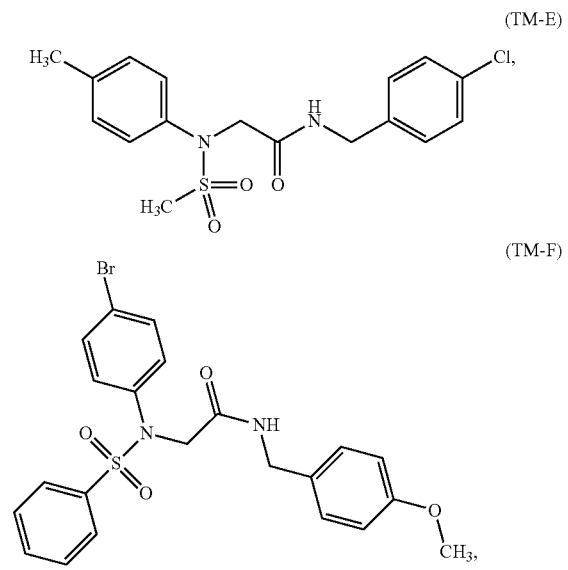

or a pharmaceutically acceptable salt thereof.

Further provided herein are TLR2 agonists for use as an adjuvant in a vaccine and/or for use in enhancing an immune response in a subject.

Other aspects of the present disclosure provide vaccines comprising an antigen and an adjuvant comprising a TLR2 agonist. In some embodiments, the vaccine is a subunit vaccine, an attenuated vaccine, or a conjugate vaccine. In some embodiments, the vaccine composition comprises an adjuvant system. In some embodiments, the adjuvant system comprises two or more adjuvants.

Other aspects of the present disclosure provide methods of enhancing an immune response to an antigen in a subject in need thereof, the method comprising administering to the subject an effective amount of an antigen and an effective amount of a TLR2 agonist.

In some embodiments, the antigen comprises a protein or polypeptide. In some embodiments, the antigen comprises a nucleic acid encoding a protein or a polypeptide. In some embodiments, the nucleic acid is DNA or RNA. In some embodiments, the antigen is from a microbial pathogen. In some embodiments, the microbial pathogen is a *mycobacterium*, bacterium, fungus, virus, parasite, or prion. In some embodiments, the bacterium is *Bacillus anthracis, Bordetella pertussis, Corynebacterium diphtheriae, Clostridium tetani, Haemophilus influenzae* type b, pneumococcus, Staphylococci spp., *Mycobacterium tuberculosis, Neiserria meningitidis, Salmonella typhi, Vibrio cholerae*, or *Yersinia pestis*. In some embodiments, the virus is adenovirus, enterovirus such as poliomyelitis, dengue virus, Ebola virus, herpes viruses such as herpes simplex virus, cytomegalovirus and varicella-zoster, measles, mumps, rubella, hepatitis A virus, hepatitis B virus, hepatitis C virus, human papilloma virus, Influenza virus, rabies, Japanese encephalitis, rotavirus, human immunodeficiency virus (HIV), respiratory syncytial virus (RSV), smallpox, yellow fever, dengue virus, or Zika Virus. In some embodiments, the parasite is *Plasmodium* spp., *Leishmania*, or a helminth. In some embodiments, the fungus is *Candida* spp., *Aspergillus* spp., *Cryptococcus* spp., *Mucormycete, Blastomyces dermatitidis, Histoplasma capsulatum*, or *Sporothrix schenckii*.

In some embodiments, the antigen is a cancer-specific antigen. In some embodiments, the antigen is a heteroclitic epitope or a cryptic epitope derived from the cancer-specific antigen. In some embodiments, the cancer-specific antigen is a neoantigen.

In some embodiments, the antigen comprises a lipopolysaccharide (LPS).

In some embodiments, the TLR2 agonist is conjugated to the antigen. In some embodiments, the TLR2 agonist is not conjugated to the antigen. In some embodiments, the antigen is adsorbed onto alum. In some embodiments, the TLR2 agonist is adsorbed onto alum. In some embodiments, the TLR2 agonist is lipidated. In some embodiments, the antigen and/or the TLR2 agonist is formulated in a liposome. In some embodiments, the antigen and/or the TLR2 agonist is formulated in a nanoparticle. In some embodiments, the antigen and/or the TLR2 agonist is in an aqueous formulation.

In some embodiments, the method further comprises administering to the subject a second adjuvant. In some embodiments, second adjuvant is an agonist of a Pattern Recognition Receptor (PRR). In some embodiments, the PRR is selected from the group consisting of Toll-like receptors (TLRs), NOD-like receptors (NLRs), RIG-I-like receptor (RLR), C-type Lectin receptors (CLRs), and a stimulator of interferon genes (STING). In some embodiments, the second adjuvant is bound to or adsorbed to alum. In some embodiments, the second adjuvant is alum. In some embodiments, the second adjuvant is an emulsion.

In some embodiments, the antigen and the TLR2 agonist are administered simultaneously. In some embodiments, the antigen and the TLR2 agonist are administered separately. In some embodiments, the antigen and the TLR2 agonist is administered once to the subject. In some embodiments, antigen and the TLR2 agonist is administered repeatedly to the subject.

In some embodiments, the TLR2 agonist activates T cell immunity. In some embodiments, the TLR2 agonist activates B cell immunity. In some embodiments, the TLR2 agonist enhances the production of antigen-specific antibodies, compared to when the antigen is administered alone. In some embodiments, the TLR2 agonist enhances the activation of antigen-specific cytotoxic T cells, compared to when the antigen is administered alone. In some embodiments, the TLR2 agonist prolongs a protective effect in the subject against the antigen, compared to when the antigen is administered alone. In some embodiments, the TLR2 agonist increases rate of an immune response, compared to when the antigen is administered alone. In some embodiments, the antigen produces a same level of immune response against the antigen at a lower dose in the presence of the TLR2 agonist, compared to when the antigen is administered alone.

In some embodiments, the subject has or is at risk of developing an infectious disease. In some embodiments, the infectious disease is caused a bacterium, a *mycobacterium*, a fungus, a virus, a parasite or a prion. In some embodiments, the infectious disease is sepsis.

In some embodiments, the subject has or is at risk of developing is cancer. In some embodiments, the cancer is metastatic cancer. In some embodiments, the cancer is melanoma.

In some embodiments, the subject has or is at risk of developing allergy.

In some embodiments, the administering is done systemically or locally. In some embodiments, the administering is done intramuscularly, intradermally, orally, intravenously, topically, intranasally, intravaginally, or sublingually. In some embodiments, the administration is prophylactic.

In some embodiments, the subject is a human neonate, an infant, an adult, or an elderly. In some embodiments, the subject is a human neonate. In some embodiments, the human infant is less than 28 days of age at the time of administration. In some embodiments, the human infant is less than 24 hours of age at the time of administration. In some embodiments, the administration occurs at birth. In some embodiments, a second administration occurs when the subject is less than or equal to 28 days of age. In some embodiments, a second administration occurs when the subject is less than 6 months of age. In some embodiments, the administration occurs when the human infant is 2 months, 4 months, and 6 months of age.

In some embodiments, the subject is born prematurely or has low birth weight. In some embodiments, the subject is a human adult. In some embodiments, the subject is an elderly. In some embodiments, the administration occurs when the subject is more than 65 years of age.

In some embodiments, the subject is a companion animal or a research animal.

In some embodiments, the subject is immune-compromised.

In some embodiments, the TLR2 composition includes the TLR2 agonist described herein. In some embodiments, the TLR2 composition includes the TLR2 agonist described herein.

Further provided herein are methods of vaccinating a subject in need thereof, the method comprising administering to the subject an effective amount of the composition or the vaccine described herein.

Further provided herein are methods of treating a disease, the method comprising administering to a subject in need thereof an effective amount of the composition or the vaccine described herein.

Yet other aspects of the present disclosure provide methods of enhancing an immune response in a subject in need thereof and/or methods of treating a disease or reducing the risk of a disease, the method comprising administering to the subject an effective amount of a TLR2 agonist.

In some embodiments, the immune response is an innate immune response. In some embodiments, the TLR2 agonist activates peripheral blood mononuclear cell (PBMC). In some embodiments, the TLR2 agonist induces the production of a proinflammatory cytokine in the subject. In some embodiments, the proinflammatory cytokine is TNF, IL-12, IL-6, or IL1-β. In some embodiments, the TLR2 agonist enhances mucosal immunity. In some embodiments, the TLR2 agonist is administered systemically or locally. In some embodiments, the administering is done intramuscularly, intradermally, orally, intravenously, topically, intranasally, intravaginally, or sublingually. In some embodiments, the administration is prophylactic. In some embodiments, the subject has or is at risk of developing an infection, allergy, or cancer. In some embodiments, the subject has radiation injury.

The summary above is meant to illustrate, in a non-limiting manner, some of the embodiments, advantages, features, and uses of the technology disclosed herein. Other embodiments, advantages, features, and uses of the technology disclosed herein will be apparent from the Detailed Description, the Drawings, the Examples, and the Claims.

Definitions

Definitions of specific functional groups and chemical terms are described in more detail below. The chemical elements are identified in accordance with the Periodic Table of the Elements, CAS version, *Handbook of Chemistry and Physics*, $75^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, $5^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, $3^{rd}$ Edition, Cambridge University Press, Cambridge, 1987. The disclosure is not intended to be limited in any manner by the exemplary listing of substituents described herein.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., Enantiomers, *Racemates and Resolutions* (Wiley Interscience, New York, 1981); Wilen et al., *Tetrahedron* 33:2725 (1977); Eliel, *Stereochemistry of Carbon Compounds* (McGraw-Hill, NY, 1962); and Wilen, *Tables of Resolving Agents and Optical Resolutions* p. 268 (E. L. Eliel, Ed., Univ. of Notre Dame Press, Notre Dame, IN 1972). The disclosure additionally encompasses compounds described herein as individual isomers substantially free of other isomers, and alternatively, as mixtures of various isomers.

When a range of values is listed, it is intended to encompass each value and sub-range within the range. For example "$C_{1-6}$" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$.

The term "aliphatic" includes both saturated and unsaturated, straight chain (i.e., unbranched), branched, acyclic, cyclic, or polycyclic aliphatic hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, the term "alkyl" includes straight, branched and cyclic alkyl groups. An analogous convention applies to other generic terms such as "alkenyl", "alkynyl", and the like. Furthermore, the terms "alkyl", "alkenyl", "alkynyl", and the like encompass both substituted and unsubstituted groups. In certain embodiments, "lower alkyl" is used to indicate those alkyl groups (cyclic, acyclic, substituted, unsubstituted, branched or unbranched) having 1-6 carbon atoms.

In certain embodiments, the alkyl, alkenyl, and alkynyl groups employed in the disclosure contain 1-20 aliphatic carbon atoms. In certain other embodiments, the alkyl, alkenyl, and alkynyl groups employed in the disclosure contain 1-10 aliphatic carbon atoms. In yet other embodiments, the alkyl, alkenyl, and alkynyl groups employed in the disclosure contain 1-8 aliphatic carbon atoms. In still other embodiments, the alkyl, alkenyl, and alkynyl groups employed in the disclosure contain 1-6 aliphatic carbon atoms. In yet other embodiments, the alkyl, alkenyl, and alkynyl groups employed in the disclosure contain 1-4 carbon atoms. Illustrative aliphatic groups thus include, but are not limited to, for example, methyl, ethyl, n-propyl, isopropyl, cyclopropyl, —CH$_2$-cyclopropyl, vinyl, allyl, n-butyl, sec-butyl, isobutyl, tert-butyl, cyclobutyl, —CH$_2$-cyclobutyl, n-pentyl, sec-pentyl, isopentyl, tert-pentyl, cyclopentyl, —CH$_2$-cyclopentyl, n-hexyl, sec-hexyl, cyclohexyl, —CH$_2$-cyclohexyl moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl, and the like.

The term "alkyl" refers to a radical of a straight-chain or branched saturated hydrocarbon group having from 1 to 10 carbon atoms ("C$_{1-10}$ alkyl"). In some embodiments, an alkyl group has 1 to 9 carbon atoms ("C$_{1-9}$ alkyl"). In some embodiments, an alkyl group has 1 to 8 carbon atoms ("C$_{1-8}$ alkyl"). In some embodiments, an alkyl group has 1 to 7 carbon atoms ("C$_{1-7}$ alkyl"). In some embodiments, an alkyl group has 1 to 6 carbon atoms ("C$_{1-6}$ alkyl"). In some embodiments, an alkyl group has 1 to 5 carbon atoms ("C$_{1-5}$ alkyl"). In some embodiments, an alkyl group has 1 to 4 carbon atoms ("C$_{1-4}$ alkyl"). In some embodiments, an alkyl group has 1 to 3 carbon atoms ("C$_{1-3}$ alkyl"). In some embodiments, an alkyl group has 1 to 2 carbon atoms ("C$_{1-2}$ alkyl"). In some embodiments, an alkyl group has 1 carbon atom ("C$_1$ alkyl"). In some embodiments, an alkyl group has 2 to 6 carbon atoms ("C$_{2-6}$ alkyl"). Examples of C$_{1-6}$ alkyl groups include methyl (C$_1$), ethyl (C$_2$), propyl (C$_3$) (e.g., n-propyl, isopropyl), butyl (C$_4$) (e.g., n-butyl, tert-butyl, sec-butyl, iso butyl), pentyl (C$_5$) (e.g., n-pentyl, 3-pentanyl, amyl, neopentyl, 3-methyl-2-butanyl, tertiary amyl), and hexyl (C$_6$) (e.g., n-hexyl). Additional examples of alkyl groups include n-heptyl (C$_7$), n-octyl (C$_8$), and the like. Unless otherwise specified, each instance of an alkyl group is independently unsubstituted (an "unsubstituted alkyl") or substituted (a "substituted alkyl") with one or more substituents (e.g., halogen, such as F). In certain embodiments, the alkyl group is an unsubstituted C$_{1-10}$ alkyl (such as unsubstituted C$_{1-6}$ alkyl, e.g., —CH$_3$ (Me), unsubstituted ethyl (Et), unsubstituted propyl (Pr, e.g., unsubstituted n-propyl (n-Pr), unsubstituted isopropyl (i-Pr)), unsubstituted butyl (Bu, e.g., unsubstituted n-butyl (n-Bu), unsubstituted tert-butyl (tert-Bu or t-Bu), unsubstituted sec-butyl (sec-Bu), unsubstituted isobutyl (i-Bu)). In certain embodiments, the alkyl group is a substituted C$_{1-10}$ alkyl (such as substituted C$_{1-6}$ alkyl, e.g., —CF$_3$, Bn).

"Alkenyl" refers to a radical of a straight-chain or branched hydrocarbon group having from 2 to 20 carbon atoms, one or more carbon-carbon double bonds, and no triple bonds ("C$_{2-20}$ alkenyl"). In some embodiments, an alkenyl group has 2 to 10 carbon atoms ("C$_{2-10}$ alkenyl"). In some embodiments, an alkenyl group has 2 to 9 carbon atoms ("C$_{2-9}$ alkenyl"). In some embodiments, an alkenyl group has 2 to 8 carbon atoms ("C$_{2-8}$ alkenyl"). In some embodiments, an alkenyl group has 2 to 7 carbon atoms ("C$_{2-7}$ alkenyl"). In some embodiments, an alkenyl group has 2 to 6 carbon atoms ("C$_{2-6}$ alkenyl"). In some embodiments, an alkenyl group has 2 to 5 carbon atoms ("C$_{2-5}$ alkenyl"). In some embodiments, an alkenyl group has 2 to 4 carbon atoms ("C$_{2-4}$ alkenyl"). In some embodiments, an alkenyl group has 2 to 3 carbon atoms ("C$_{2-3}$ alkenyl"). In some embodiments, an alkenyl group has 2 carbon atoms ("C$_2$ alkenyl"). The one or more carbon-carbon double bonds can be internal (such as in 2-butenyl) or terminal (such as in 1-butenyl). Examples of C$_{2-4}$ alkenyl groups include ethenyl (C$_2$), 1-propenyl (C$_3$), 2-propenyl (C$_3$), 1-butenyl (C$_4$), 2-butenyl (C$_4$), butadienyl (C$_4$), and the like. Examples of C$_{2-6}$ alkenyl groups include the aforementioned C$_{2-4}$ alkenyl groups as well as pentenyl (C$_5$), pentadienyl (C$_5$), hexenyl (C$_6$), and the like. Additional examples of alkenyl include heptenyl (C$_7$), octenyl (C$_8$), octatrienyl (C$_8$), and the like. Unless otherwise specified, each instance of an alkenyl group is independently optionally substituted, i.e., unsubstituted (an "unsubstituted alkenyl") or substituted (a "substituted alkenyl") with one or more substituents. In certain embodiments, the alkenyl group is unsubstituted C$_{2-10}$ alkenyl. In certain embodiments, the alkenyl group is substituted C$_{2-10}$ alkenyl. In an alkenyl group, a C═C double bond for which the stereochemistry is not specified (e.g., —CH═CHCH$_3$ or

)

may be an (E)- or (Z)-double bond.

"Alkynyl" refers to a radical of a straight-chain or branched hydrocarbon group having from 2 to 20 carbon atoms, one or more carbon-carbon triple bonds, and optionally one or more double bonds ("C$_{2-20}$ alkynyl"). In some embodiments, an alkynyl group has 2 to 10 carbon atoms ("C$_{2-10}$ alkynyl"). In some embodiments, an alkynyl group has 2 to 9 carbon atoms ("C$_{2-9}$ alkynyl"). In some embodiments, an alkynyl group has 2 to 8 carbon atoms ("C$_{2-8}$ alkynyl"). In some embodiments, an alkynyl group has 2 to 7 carbon atoms ("C$_{2-7}$ alkynyl"). In some embodiments, an alkynyl group has 2 to 6 carbon atoms ("C$_{2-6}$ alkynyl"). In some embodiments, an alkynyl group has 2 to 5 carbon atoms ("C$_{2-5}$ alkynyl"). In some embodiments, an alkynyl group has 2 to 4 carbon atoms ("C$_{2-4}$ alkynyl"). In some embodiments, an alkynyl group has 2 to 3 carbon atoms ("C$_{2-3}$ alkynyl"). In some embodiments, an alkynyl group has 2 carbon atoms ("C$_2$ alkynyl"). The one or more carbon-carbon triple bonds can be internal (such as in 2-butynyl) or terminal (such as in 1-butynyl). Examples of C$_{2-4}$ alkynyl groups include, without limitation, ethynyl (C$_2$), 1-propynyl (C$_3$), 2-propynyl (Ca), 1-butynyl (C$_4$), 2-butynyl (C$_4$), and the like. Examples of C$_{2-6}$ alkenyl groups include the aforementioned C$_{2-4}$ alkynyl groups as well as pentynyl (C$_5$), hexynyl (C$_6$), and the like. Additional examples of alkynyl include heptynyl (C$_7$), octynyl (C$_8$), and the like. Unless otherwise specified, each instance of an alkynyl group is independently optionally substituted, i.e., unsubstituted (an "unsubstituted alkynyl") or substituted (a "substituted alkynyl") with one or more substituents. In certain embodiments, the alkynyl group is unsubstituted C$_{2-10}$ alkynyl. In certain embodiments, the alkynyl group is substituted C$_{2-10}$ alkynyl.

"Carbocyclyl" or "carbocyclic" refers to a radical of a non-aromatic cyclic hydrocarbon group having from 3 to 10 ring carbon atoms ("C$_{3-10}$ carbocyclyl") and zero heteroatoms in the non-aromatic ring system. In some embodiments, a carbocyclyl group has 3 to 8 ring carbon atoms ("C$_{3-8}$ carbocyclyl"). In some embodiments, a carbocyclyl group has 3 to 6 ring carbon atoms ("C$_{3-6}$ carbocyclyl"). In some embodiments, a carbocyclyl group has 3 to 6 ring carbon atoms ("C$_{3-6}$ carbocyclyl"). In some embodiments, a carbocyclyl group has 5 to 10 ring carbon atoms ("C$_{5-10}$ carbocyclyl"). Exemplary C$_{3-6}$ carbocyclyl groups include, without limitation, cyclopropyl (C$_3$), cyclopropenyl (C$_3$), cyclobutyl (C$_4$), cyclobutenyl (C$_4$), cyclopentyl (C$_5$), cyclopentenyl (C$_5$), cyclohexyl (C$_6$), cyclohexenyl (C$_6$), cyclohexadienyl (C$_6$), and the like. Exemplary C$_{3-8}$ carbocyclyl groups include, without limitation, the aforementioned C$_{3-6}$ carbocyclyl groups as well as cycloheptyl (C$_7$), cycloheptenyl (C$_7$), cycloheptadienyl (C$_7$), cycloheptatrienyl (C$_7$), cyclooctyl (C$_8$), cyclooctenyl (C$_8$), bicyclo[2.2.1]heptanyl (C$_7$), bicyclo[2.2.2]octanyl (C$_8$), and the like. Exemplary C$_{3-10}$ carbocyclyl groups include, without limitation, the aforementioned C$_{3-8}$ carbocyclyl groups as well as cyclononyl (C$_9$), cyclononenyl (C$_9$), cyclodecyl (C$_{10}$), cyclodecenyl (C$_{10}$), octahydro-1H-indenyl (C$_9$), decahydronaphthalenyl (C$_{10}$), spiro[4.5]decanyl (C$_{10}$), and the like. As the foregoing examples illustrate, in certain embodiments, the carbocyclyl group is either monocyclic ("monocyclic carbocyclyl") or contain a fused, bridged or spiro ring system such as a bicyclic system ("bicyclic carbocyclyl") and can be saturated or can be partially unsaturated. "Carbocyclyl" also includes ring systems wherein the carbocyclic ring, as defined above, is fused with one or more aryl or heteroaryl groups wherein the point of attachment is on the carbocyclic ring, and in such instances, the number of carbons continue to designate the number of carbons in the carbocyclic ring system. Unless otherwise specified, each instance of a carbocyclyl group is independently optionally substituted, i.e., unsubstituted (an "unsubstituted carbocyclyl") or substituted (a "substituted carbocyclyl") with one or more substituents. In certain embodiments, the carbocyclyl group is unsubstituted C$_3$ 10 carbocyclyl. In certain embodiments, the carbocyclyl group is substituted C$_{3-10}$ carbocyclyl.

In some embodiments, "carbocyclyl" is a monocyclic, saturated carbocyclyl group having from 3 to 10 ring carbon atoms ("C$_{3-10}$ cycloalkyl"). In some embodiments, a cycloalkyl group has 3 to 8 ring carbon atoms ("C$_{3-8}$ cycloalkyl"). In some embodiments, a cycloalkyl group has 3 to 6 ring carbon atoms ("C$_{3-6}$ cycloalkyl"). In some embodiments, a cycloalkyl group has 5 to 6 ring carbon atoms ("C$_{5-6}$ cycloalkyl"). In some embodiments, a cycloalkyl group has 5 to 10 ring carbon atoms ("C$_{5-10}$ cycloalkyl"). Examples of C$_{5-6}$ cycloalkyl groups include cyclopentyl (C$_5$) and cyclohexyl (C$_5$). Examples of C$_{3-6}$ cycloalkyl groups include the aforementioned C$_{5-6}$ cycloalkyl groups as well as cyclopropyl (C$_3$) and cyclobutyl (C$_4$). Examples of C$_{3-8}$ cycloalkyl groups include the aforementioned C$_{3-6}$ cycloalkyl groups as well as cycloheptyl (C$_7$) and cyclooctyl (C$_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted C$_{3-10}$ cycloalkyl. In certain embodiments, the cycloalkyl group is substituted C$_{3-10}$ cycloalkyl.

"Heterocyclyl" or "heterocyclic" refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged, or spiro ring system, such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclic ring, as defined above, is fused with one or more carbocyclyl groups wherein the point of attachment is either on the carbocyclyl or heterocyclic ring, or ring systems wherein the heterocyclic ring, as defined above, is fused with one or more aryl or heteroaryl groups, wherein the point of attachment is on the heterocyclic ring, and in such instances, the number of ring members continue to designate the number of ring members in the heterocyclic ring system. Unless otherwise specified, each instance of heterocyclyl is independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, thiiranyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, and dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

"Aryl" refers to a radical of a monocyclic or polycyclic (e.g., bicyclic or tricyclic) 4n+2 aromatic ring system (e.g., having 6, 10, or 14 pi electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted $C_{6-14}$ aryl. In certain embodiments, the aryl group is substituted $C_{6-14}$ aryl.

"Aralkyl" is a subset of alkyl and aryl and refers to an optionally substituted alkyl group substituted by an optionally substituted aryl group. In certain embodiments, the aralkyl is optionally substituted benzyl. In certain embodiments, the aralkyl is benzyl. In certain embodiments, the aralkyl is optionally substituted phenethyl. In certain embodiments, the aralkyl is phenethyl.

"Heteroaryl" refers to a radical of a 5-10 membered monocyclic or bicyclic 4n+2 aromatic ring system (e.g., having 6 or 10 pi electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system.

"Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, i.e., unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl, and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

"Heteroaralkyl" is a subset of alkyl and heteroaryl and refers to an optionally substituted alkyl group substituted by an optionally substituted heteroaryl group.

"Unsaturated" or "partially unsaturated" refers to a group that includes at least one double or triple bond. A "partially unsaturated" ring system is further intended to encompass rings having multiple sites of unsaturation, but is not intended to include aromatic groups (e.g., aryl or heteroaryl groups). Likewise, "saturated" refers to a group that does not contain a double or triple bond, i.e., contains all single bonds.

Alkyl, alkenyl, alkynyl, carbocyclyl, heterocyclyl, aryl, and heteroaryl groups, which are divalent bridging groups, are further referred to using the suffix-ene, e.g., alkylene, alkenylene, alkynylene, carbocyclylene, heterocyclylene, arylene, and heteroarylene.

An atom, moiety, or group described herein may be unsubstituted or substituted, as valency permits, unless otherwise provided expressly. The term "optionally substituted" refers to substituted or unsubstituted.

A group is optionally substituted unless expressly provided otherwise. The term "optionally substituted" refers to being substituted or unsubstituted. In certain embodiments, alkyl, alkenyl, alkynyl, carbocyclyl, heterocyclyl, aryl, and heteroaryl groups are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present disclosure contemplates any and all such combinations in order to arrive at a stable compound. For purposes of this disclosure, heteroatoms such as nitrogen may have hydrogen substituents and/or any suitable substituent as described herein which satisfy the valencies of the heteroatoms and results in the formation of a stable moiety. In certain embodiments, the substituent is a carbon atom substituent. In certain embodiments, the substituent is a nitrogen atom substituent. In certain embodiments, the substituent is an oxygen atom substituent. In certain embodiments, the substituent is a sulfur atom substituent.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$) N(R$^{bb}$)$_2$, —OC(=NR$^{bb}$) N(R$^{bb}$)$_2$, —NR$^{bb}$C(=NR$^{bb}$) N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$ —C(=S)N(R$^{bb}$)$_2$, —C(=O)SR$^{aa}$, —C(=S) SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)(R$^{aa}$)$_2$, —P(=O)(OR$^{cc}$)$_2$, —OP(=O)(R$^{aa}$)$_2$, —OP(=O)(OR$^{cc}$)$_2$, —P(=O)(N(R$^{bb}$)$_2$)$_2$, —OP(=O)(N(R$^{bb}$)$_2$)$_2$, —NR$^{bb}$P (=O)(R$^{aa}$)$_2$, —NR$^{bb}$P(=O)(OR(C)$_2$, —NR$^{bb}$P(=O)(N(R$^{bb}$)$_2$)$_2$, —P(R$^{cc}$)$_2$, —P(OR$^{cc}$)$_2$, —P(R$^{cc}$)$_3$$^+$X$^-$, —P(OR$^{cc}$)$_3$$^+$X$^-$, —P(R$^{cc}$)$_4$, —P(OR$^{cc}$)$_4$, —OP(R$^{cc}$)$_2$, —OP(R$^{cc}$)$_3$$^+$X$^-$, —OP(OR$^{cc}$)$_2$, —OP(OR$^{cc}$)$_3$$^+$X$^-$, —OP(R$^{cc}$)$_4$, —OP(OR$^{cc}$)$_4$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups; wherein X$^-$ is a counterion;

or two geminal hydrogens on a carbon atom are replaced with the group =O, =S, =NN(R$^{bb}$)$_2$, =NNR$^{bb}$C (=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_2$-alkenyl, C$_{2-10}$ alkynyl, heteroC$_{1-10}$ alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$) N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)(R$^{aa}$)$_2$, —P(=O)(OR$^{cc}$)$_2$, —P(=O)(N(R$^{cc}$)$_2$)$_2$, C$_{1-10}$ alkyl, C$_{1-10}$ perhaloalkyl, C$_{2-10}$ alkenyl, C$_{2-10}$ alkynyl, heteroC$_{1-10}$alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups; wherein X$^-$ is a counterion;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of $R^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O) R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$) OR$^{ee}$, —C(=NR$^{ff}$) N(R$^{ff}$)$_2$, —OC(=NR$^{ff}$) N(R$^{ff}$)$_2$, —NR$^{ff}$C(=NR$^{ff}$) N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N (R$^{ff}$)$_2$, —C(=O)SR$^{ee}$, —C(=S)SR$^{ee}$, —SC(=S)SR$^{ee}$, —P(=O)(OR$^{ee}$)$_2$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, 3-10 membered heterocyclyl, C$_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups, or two geminal Rod substituents can be joined to form =O or =S; wherein X$^-$ is a counterion;

each instance of R$^{ee}$ is, independently, selected from C$_{1-6}$ alkyl, C$_{1-6}$ perhaloalkyl, C$_{2-6}$ alkenyl, C$_{2-6}$ alkynyl, heteroC$_{1-6}$ alkyl, heteroC$_{2-6}$alkenyl, heteroC$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, 3-10 membered heterocyclyl, C$_{6-10}$ aryl and 5-10 membered heteroaryl, or two R$^{ff}$ groups are joined to form a 3-10 membered heterocyclyl or 5-10 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups; and each instance of R$^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3^+$X$^-$, —NH(C$_{1-6}$ alkyl)$_2^+$X$^-$, —NH$_2$ (C$_{1-6}$ alkyl)$^+$X$^-$, —NH$_3^+$X$^-$, —N(OC$_{1-6}$ alkyl) (C$_{1-6}$ alkyl), —N(OH) (C$_{1-6}$ alkyl), —NH(OH), —SH, —SC$_{1-6}$ alkyl, —SS(C$_{1-6}$ alkyl), —C(=O) (C$_{1-6}$ alkyl), —CO$_2$H, —CO$_2$ (C$_{1-6}$ alkyl), —OC(=O) (C$_{1-6}$ alkyl), —OCO$_2$ (C$_{1-6}$ alkyl), —C(=O)NH$_2$, —C(=O)N(C$_{1-6}$ alkyl)$_2$, —OC(=O)NH(C$_{1-6}$ alkyl), —NHC(=O) (C$_{1-6}$ alkyl), —N(C$_{1-6}$ alkyl) C(=O) (C$_{1-6}$ alkyl), —NHCO$_2$ (C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH) O(C$_{1-6}$ alkyl), —OC(=NH) (C$_{1-6}$ alkyl), —OC(=NH) OC$_{1-6}$ alkyl, —C(=NH) N(C$_{1-6}$ alkyl)$_2$, —C(=NH) NH(C$_{1-6}$ alkyl), —C(=NH) NH$_2$, —OC (=NH) N(C$_{1-6}$ alkyl)$_2$, —OC(NH) NH(C$_{1-6}$ alkyl), —OC(NH) NH$_2$, —NHC(NH) N(C$_{1-6}$ alkyl)$_2$, —NHC (=NH) NH$_2$, —NHSO$_2$ (C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$ —C(=S) N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC (=S)SC$_{1-6}$ alkyl, —P(=O)(OC$_{1-6}$ alkyl)$_2$, —P(=O) (C$_{1-6}$ alkyl)$_2$, —OP(=O) (C$_{1-6}$ alkyl)$_2$, —OP(=O) (OC$_{1-6}$ alkyl)$_2$, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, C$_{6-10}$ aryl, 3-10 membered heterocyclyl, 5-10 membered heteroaryl; or two geminal R$^{gg}$ substituents can be joined to form =O or =S; wherein X$^-$ is a counterion.

A "counterion" or "anionic counterion" is a negatively charged group associated with a positively charged group in order to maintain electronic neutrality. An anionic counterion may be monovalent (i.e., including one formal negative charge). An anionic counterion may also be multivalent (i.e., including more than one formal negative charge), such as divalent or trivalent. Exemplary counterions include halide ions (e.g., F$^-$, Cl$^-$, Br$^-$, I$^-$), NO$_3^-$, ClO$_4^-$, OH$^-$, H$_2$PO$_4^-$, HCO$_3^-$, HSO$_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), carboxylate ions (e.g., acetate, propanoate, benzoate, glycerate, lactate, tartrate, glycolate, gluconate, and the like), BF$_4^-$, PF$_4^-$, PF$_6^-$, AsF$_6^-$, SbF$_6^-$, B[3,5-(CF$_3$)$_2$C$_6$H$_3$]$_4^-$, B(C$_6$F$_5$)$_4^-$, BPh$_4^-$, Al(OC (CF$_3$)$_3$)$_4^-$, and carborane anions (e.g., CB$_{11}$H$_{12}^-$ or (HCB$_1$Me$_5$Br$_6$)$^-$). Exemplary counterions which may be multivalent include CO$_3^{2-}$, HPO$_4^{2-}$, PO$_4^{3-}$, B$_4$O$_7^{2-}$, SO$_4^{2-}$, S$_2$O$_3^{2-}$, carboxylate anions (e.g., tartrate, citrate, fumarate, maleate, malate, malonate, gluconate, succinate, glutarate, adipate, pimelate, suberate, azelate, sebacate, salicylate, phthalates, aspartate, glutamate, and the like), and carboranes.

"Halo" or "halogen" refers to fluorine (fluoro, —F), chlorine (chloro, —Cl), bromine (bromo, —Br), or iodine (iodo, —I).

"Acyl" refers to a moiety selected from the group consisting of —C(=O)R$^{aa}$, —CHO, —CO$_2$R$^{aa}$, —C(=O)N (R$^{bb}$)$_2$, —C(=NR$^{bb}$)R$^{aa}$, —C(=NR$^{bb}$)OR$^{aa}$, —C(=NR$^{bb}$) N(R$^{bb}$)$_2$, —C(=O)NR$^{bb}$SO$_2$R$^{aa}$, —C(=S)N(R$^{bb}$)$_2$, —C(=O)SR$^{aa}$, or —C(=S)SR$^{aa}$, wherein R$^{aa}$ and R$^{bb}$ are as defined herein.

Nitrogen atoms can be substituted or unsubstituted as valency permits, and include primary, secondary, tertiary, and quaternary nitrogen atoms. Exemplary nitrogen atom substituents include, but are not limited to, hydrogen, —OH, —OR$^{aa}$, —N(R$^{cc}$)$_2$, —CN, —C(=O)R$^{aa}$, —C(=O) N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$) N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)(OR$^{cc}$)$_2$, —P(=O)(R$^{aa}$)$_2$, —P(=O)(N(R$^{cc}$)$_2$)$_2$, C$_{1-10}$ alkyl, C$_{1-10}$ perhaloalkyl, C$_{2-10}$ alkenyl, C$_{2-10}$ alkynyl, heteroC$_{1-10}$alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{cc}$ groups attached to an N atom are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, Rec and R$^{dd}$ are as defined above.

In certain embodiments, the substituent present on the nitrogen atom is an nitrogen protecting group (also referred to herein as an "amino protecting group"). Nitrogen protecting groups include, but are not limited to, —OH, —OR$^{aa}$, —N(R$^{cc}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$) OR$^{aa}$, —C(=NR$^{cc}$) N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, C$_{1-10}$ alkyl (e.g., aralkyl, heteroaralkyl), C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl groups, wherein each alkyl, alkenyl, alkynyl, heteroalkyl, heteroalkenyl, heteroalkynyl, carbocyclyl, heterocyclyl, aralkyl, aryl, and heteroaryl is independently substituted with 0, 1, 2, 3, 4, or 5 R$^{dd}$ groups, and wherein R$^{aa}$, R$^{bb}$, Rec and R$^{dd}$ are as defined herein. Nitrogen protecting groups are well known in the art and include those described in detail in Protecting Groups in Organic Synthesis, T. W. Greene and P. G. M. Wuts, 3rd edition, John Wiley & Sons, 1999, incorporated herein by reference.

For example, nitrogen protecting groups such as amide groups (e.g., —C(=O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxyacylamino) acetamide, 3-(p-hydroxyphenyl) propanamide, 3-(o-nitrophenyl) propanamide, 2-methyl-2-(o-nitrophenoxy) propanamide, 2-methyl-2-(o-phenylazophenoxy) propanamide, 4-chlorobutanamide, 3-methyl-3-nitrobutanamide, o-nitrocinnamide, N-acetylmethionine derivative, o-nitrobenzamide and o-(benzoyloxymethyl)benzamide.

Nitrogen protecting groups such as carbamate groups (e.g., —C(=O)OR$^{aa}$) include, but are not limited to, methyl carbamate, ethyl carbamate, 9-fluorenylmethyl carbamate (Fmoc), 9-(2-sulfo) fluorenylmethyl carbamate, 9-(2,7-dibromo) fluoroenylmethyl carbamate, 2,7-di-t-butyl-[9-(10, 10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl) ethyl carbamate (Pyoc), 2-(N,N-dicyclohexylcarboxamido) ethyl carbamate, t-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitrobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl (o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido) propyl carbamate, 1,1-dimethylpropynyl carbamate, di (2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo) benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., —S(=O)$_2$R$^{aa}$) include, but are not limited to, p-toluenesulfonamide (Ts), benzenesulfonamide, 2,3,6-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide. Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl) ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di (4-methoxyphenyl) methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl) mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl) phenylmethyleneamine, N-cyclohexylideneamine, N-(5,5-dimethyl-3-oxo-1-cyclohexenyl)amine, N-borane derivative, N-diphenylborinic acid derivative, N-[phenyl (pentaacylchromium- or tungsten) acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfonamide (Npys).

In certain embodiments, the substituent present on an oxygen atom is an oxygen protecting group (also referred to herein as an "hydroxyl protecting group"). Oxygen protecting groups include, but are not limited to, $-R^{aa}$, $-N(R^{bb})_2$, $-C(=O)SR^{aa}$, $-C(=O)R^{aa}$, $-CO_2R^{aa}$, $-C(=O)N(R^{bb})_2$, $-C(=NR^{bb})R^{aa}$, $-C(=NR^{bb})OR^{aa}$, $-C(=NR^{bb})N(R^{bb})_2$, $-S(=O)R^{aa}$, $-SO_2R^{aa}$, $-Si(R^{aa})_3$, $-P(R^{cc})_2$, $-P(R^{cc})_3{}^+X^-$, $-P(OR^{cc})_2$, $-P(OR^{cc})_3{}^+X^-$, $-P(=O)(R^{aa})_2$, $-P(=O)(OR^{cc})_2$, and $-P(=O)(N(R^{bb})_2)_2$, wherein $X^-$, $R^{aa}$, $R^{bb}$, and $R^{cc}$ are as defined herein. Oxygen protecting groups are well known in the art and include those described in detail in Protecting Groups in Organic Synthesis, T. W. Greene and P. G. M. Wuts, $3^{rd}$ edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxido, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, a-naphthyldiphenylmethyl, p-methoxyphenyldiphenylmethyl, di (p-methoxyphenyl)phenylmethyl, tri (p-methoxyphenyl)methyl, 4-(4'-bromophenacyloxyphenyl)diphenylmethyl, 4,4',4"-tris (4,5-dichlorophthalimidophenyl)methyl, 4,4',4"-tris (levulinoyloxyphenyl)methyl, 4,4',4"-tris (benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl) xanthenyl, 9-(9-phenyl-10-oxo) anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio) pentanoate (levulinoyldithioacetal), pivaloate, adamantoate, crotonate, 4-methoxycrotonate, benzoate, p-phenylbenzoate, 2,4,6-trimethylbenzoate (mesitoate), methyl carbonate, 9-fluorenylmethyl carbonate (Fmoc), ethyl carbonate, 2,2,2-trichloroethyl carbonate (Troc), 2-(trimethylsilyl)ethyl carbonate (TMSEC), 2-(phenylsulfonyl)ethyl carbonate (Psec), 2-(triphenylphosphonio)ethyl carbonate (Peoc), isobutyl carbonate, vinyl carbonate, allyl carbonate, t-butyl carbonate (BOC or Boc), p-nitrophenyl carbonate, benzyl carbonate, p-methoxybenzyl carbonate, 3,4-dimethoxybenzyl carbonate, o-nitrobenzyl carbonate, p-nitrobenzyl carbonate, S-benzyl thiocarbonate, 4-ethoxy-1-napthhyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy) butyrate, 2-(methylthiomethoxymethyl)benzoate, 2,6-dichloro-4-methylphenoxyacetate, 2,6-dichloro-4-(1,1,3,3-tetramethylbutyl) phenoxyacetate, 2,4-bis(1,1-dimethylpropyl) phenoxyacetate, chlorodiphenylacetate, isobutyrate, monosuccinoate, (E)-2-methyl-2-butenoate, o-(methoxyacyl)benzoate, a-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, the substituent present on a sulfur atom is a sulfur protecting group (also referred to as a "thiol protecting group"). Sulfur protecting groups include, but are not limited to, $-R^{aa}$, $-N(R^{bb})_2$, $-C(=O)SR^{aa}$, $-C(=O)R^{aa}$, $-CO_2R^{aa}$, $-C(=O)N(R^{bb})_2$, $-C(=NR^{bb})R^{aa}$, $-C(=NR^{bb})OR^{aa}$, $-C(=NR^{bb})N(R^{bb})_2$, $-S(=O)R^{aa}$, $-SO_2R^{aa}$, $-Si(R^{aa})_3$, $-P(R^{cc})_2$, $-P(R^{cc})_3{}^+X^-$, $-P(OR^{cc})_2$, $-P(OR^{cc})_3{}^+X^-$, $-P(=O)(R^{aa})_2$, $-P(=O)(OR^{cc})_2$, and $-P(=O)(N(R^{bb})_2)_2$, wherein $R^{aa}$, $R^{bb}$, and $R^{cc}$ are as defined herein. Sulfur protecting groups are well known in the art and include those described in detail in Protecting Groups in Organic Synthesis, T. W. Greene and P. G. M. Wuts, $3^{rd}$ edition, John Wiley & Sons, 1999, incorporated herein by reference.

As used herein, a "leaving group" (LG) is an art-understood term referring to a molecular fragment that departs with a pair of electrons in heterolytic bond cleavage, wherein the molecular fragment is an anion or neutral molecule. As used herein, a leaving group can be an atom or a group capable of being displaced by a nucleophile. See, for example, Smith, March Advanced Organic Chemistry 6th ed. (501-502). Exemplary leaving groups include, but are not limited to, halo (e.g., chloro, bromo, iodo) and activated substituted hydroxyl groups (e.g., $-OC(=O)SR^{aa}$, $-OC(=O)R^{aa}$, $-OCO_2R^{aa}$, $-OC(=O)N(R^{bb})_2$, $-OC(=NR^{bb})R^{aa}$, $-OC(=NR^{bb})OR^{aa}$, $-OC(=NR^{bb})N(R^{bb})_2$, $-OS(=O)R^{aa}$, $-OSO_2R^{aa}$, $-OP(R^{cc})_2$, $-OP(R^{cc})_3$, $-OP(=O)_2R^{aa}$, $-OP(=O)(R^{aa})_2$, $-OP(=O)(OR^{cc})_2$, $-OP(=O)_2N(R^{bb})_2$, and $-OP(=O)(NR^{bb})_2$, wherein $R^{aa}$, $R^{bb}$, and $R^{cc}$ are as defined herein).

A "hydrocarbon chain" refers to a substituted or unsubstituted divalent alkyl, alkenyl, or alkynyl group. A hydrocarbon chain includes (1) one or more chains of carbon atoms immediately between the two radicals of the hydrocarbon chain; (2) optionally one or more hydrogen atoms on the chain(s) of carbon atoms; and (3) optionally one or more substituents ("non-chain substituents," which are not hydrogen) on the chain(s) of carbon atoms. A chain of carbon atoms consists of consecutively connected carbon atoms ("chain atoms") and does not include hydrogen atoms or heteroatoms. However, a non-chain substituent of a hydrocarbon chain may include any atoms, including hydrogen atoms, carbon atoms, and heteroatoms. For example, hydrocarbon chain —C$^A$H(C$^B$H$_2$C$^C$H$_3$)— includes one chain atom C$^A$, one hydrogen atom on C$^A$, and non-chain substituent —(C$^B$H$_2$C$^C$H$_3$). The term "C$_x$ hydrocarbon chain," wherein x is a positive integer, refers to a hydrocarbon chain that includes x number of chain atom(s) between the two radicals of the hydrocarbon chain. If there is more than one possible value of x, the smallest possible value of x is used for the definition of the hydrocarbon chain. For example, —CH(C$_2$H$_5$)— is a C$_1$ hydrocarbon chain, and

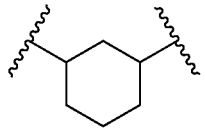 [SMILES: *C1CCCC(*)C1]

is a C$_3$ hydrocarbon chain. When a range of values is used, the meaning of the range is as described herein. For example, a C$_{3-10}$ hydrocarbon chain refers to a hydrocarbon chain where the number of chain atoms of the shortest chain of carbon atoms immediately between the two radicals of the hydrocarbon chain is 3, 4, 5, 6, 7, 8, 9, or 10. A hydrocarbon chain may be saturated (e.g., —(CH$_2$)$_4$—). A hydrocarbon chain may also be unsaturated and include one or more C═C and/or C≡C bonds anywhere in the hydrocarbon chain. For instance, —CH═CH—(CH$_2$)$_2$—, —CH$_2$—C≡C—CH$_2$—, and —C≡C—CH═CH— are all examples of a unsubstituted and unsaturated hydrocarbon chain. In certain embodiments, the hydrocarbon chain is unsubstituted (e.g., —C≡C— or —(CH$_2$)$_4$—). In certain embodiments, the hydrocarbon chain is substituted (e.g., —CH(C$_2$H$_5$)— and —CF$_2$—). Any two substituents on the hydrocarbon chain may be joined to form an optionally substituted carbocyclyl, optionally substituted heterocyclyl, optionally substituted aryl, or optionally substituted heteroaryl ring. For instance,

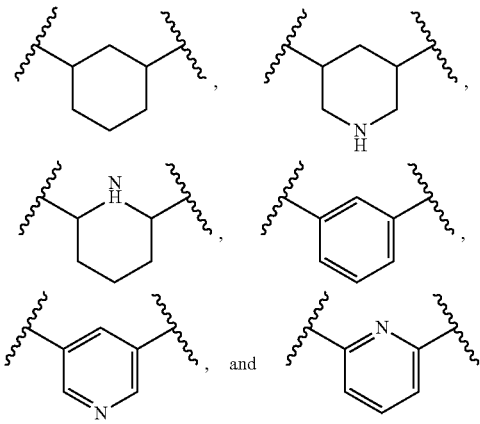

are all examples of a hydrocarbon chain. In contrast, in certain embodiments,

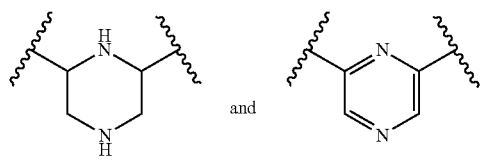 [SMILES: *C1CNCC(*)N1 ; *c1cncc(*)n1]

are not within the scope of the hydrocarbon chains described herein. When a chain atom of a C$_x$ hydrocarbon chain is replaced with a heteroatom, the resulting group is referred to as a C$_x$ hydrocarbon chain wherein a chain atom is replaced with a heteroatom, as opposed to a C$_{x-1}$ hydrocarbon chain. For example,

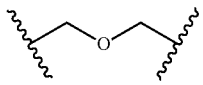 [SMILES: *COC*]

is a C$_3$ hydrocarbon chain wherein one chain atom is replaced with an oxygen atom.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. For example, Berge et al., describe pharmaceutically acceptable salts in detail in *J. Pharmaceutical Sciences*, 1977, 66, 1-19, incorporated herein by reference. Pharmaceutically acceptable salts of the compounds described herein include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid, and perchloric acid or with organic acids such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and N$^+$(C$_{1-4}$ alkyl)$_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

The term "solvate" refers to forms of the compound, or a salt thereof, that are associated with a solvent, usually by a solvolysis reaction. This physical association may include hydrogen bonding. Conventional solvents include water, methanol, ethanol, acetic acid, DMSO, THF, diethyl ether, and the like. The compounds described herein may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolatable solvates. Representative solvates include hydrates, ethanolates, and methanolates.

The term "hydrate" refers to a compound that is associated with water. Typically, the number of the water molecules contained in a hydrate of a compound is in a definite ratio to the number of the compound molecules in the hydrate. Therefore, a hydrate of a compound may be represented, for example, by the general formula R·x H$_2$O, wherein R is the compound, and x is a number greater than 0. A given compound may form more than one type of hydrate, including, e.g., monohydrates (x is 1), lower hydrates (x is a number greater than 0 and smaller than 1, e.g., hemihydrates (R·0.5H$_2$O)), and polyhydrates (x is a number greater than 1, e.g., dihydrates (R·2H$_2$O) and hexahydrates (R·6H$_2$O)).

The term "tautomers" or "tautomeric" refers to two or more interconvertible compounds resulting from at least one formal migration of a hydrogen atom and at least one change in valency (e.g., a single bond to a double bond, a triple bond to a single bond, or vice versa). The exact ratio of the tautomers depends on several factors, including temperature, solvent, and pH. Tautomerizations (i.e., the reaction providing a tautomeric pair) may catalyzed by acid or base. Exemplary tautomerizations include keto-to-enol, amide-to-imide, lactam-to-lactim, enamine-to-imine, and enamine-to-(a different enamine) tautomerizations.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The term "polymorphs" refers to a crystalline form of a compound (or a salt, hydrate, or solvate thereof). All polymorphs have the same elemental composition. Different crystalline forms usually have different X-ray diffraction patterns, infrared spectra, melting points, density, hardness, crystal shape, optical and electrical properties, stability, and solubility. Recrystallization solvent, rate of crystallization, storage temperature, and other factors may cause one crystal form to dominate. Various polymorphs of a compound can be prepared by crystallization under different conditions.

The term "prodrugs" refers to compounds that have cleavable groups and become by solvolysis or under physiological conditions the compounds described herein, which are pharmaceutically active in vivo. Such examples include, but are not limited to, choline ester derivatives and the like, N-alkylmorpholine esters and the like. Other derivatives of the compounds described herein have activity in both their acid and acid derivative forms, but in the acid sensitive form often offer advantages of solubility, tissue compatibility, or delayed release in the mammalian organism (see, Bundgard, H., *Design of Prodrugs*, pp. 7-9, 21-24, Elsevier, Amsterdam 1985). Prodrugs include acid derivatives well known to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides, and anhydrides derived from acidic groups pendant on the compounds described herein are particular prodrugs. In some cases it is desirable to prepare double ester type prodrugs such as (acyloxy)alkyl esters or ((alkoxycarbonyl)oxy)alkylesters. $C_1$-$C_8$ alkyl, $C_2$-$C_8$ alkenyl, $C_2$-$C_8$ alkynyl, aryl, $C_7$-$C_{12}$ substituted aryl, and $C_7$-$C_{12}$ arylalkyl esters of the compounds described herein may be preferred.

The term "small molecule" refers to molecules, whether naturally-occurring or artificially created (e.g., via chemical synthesis) that have a relatively low molecular weight. Typically, a small molecule is an organic compound (i.e., it contains carbon). The small molecule may contain multiple carbon-carbon bonds, stereocenters, and other functional groups (e.g., amines, hydroxyl, carbonyls, and heterocyclic rings, etc.). In certain embodiments, the molecular weight of a small molecule is not more than about 1,000 g/mol, not more than about 900 g/mol, not more than about 800 g/mol, not more than about 700 g/mol, not more than about 600 g/mol, not more than about 500 g/mol, not more than about 400 g/mol, not more than about 300 g/mol, not more than about 200 g/mol, or not more than about 100 g/mol. In certain embodiments, the molecular weight of a small molecule is at least about 100 g/mol, at least about 200 g/mol, at least about 300 g/mol, at least about 400 g/mol, at least about 500 g/mol, at least about 600 g/mol, at least about 700 g/mol, at least about 800 g/mol, or at least about 900 g/mol, or at least about 1,000 g/mol. Combinations of the above ranges (e.g., at least about 200 g/mol and not more than about 500 g/mol) are also possible. In certain embodiments, the small molecule is a therapeutically active agent such as a drug (e.g., a molecule approved by the U.S. Food and Drug Administration as provided in the Code of Federal Regulations (C.F.R.)). The small molecule may also be complexed with one or more metal atoms and/or metal ions. In this instance, the small molecule is also referred to as a "small organometallic molecule." Preferred small molecules are biologically active in that they produce a biological effect in animals, preferably mammals, more preferably humans. Small molecules include, but are not limited to, radionuclides and imaging agents. In certain embodiments, the small molecule is a drug. Preferably, though not necessarily, the drug is one that has already been deemed safe and effective for use in humans or animals by the appropriate governmental agency or regulatory body. For example, drugs approved for human use are listed by the FDA under 21 C.F.R. §§ 330.5, 331 through 361, and 440 through 460, incorporated herein by reference; drugs for veterinary use are listed by the FDA under 21 C.F.R. §§ 500 through 589, incorporated herein by reference. All listed drugs are considered acceptable for use in accordance with the present invention.

The terms "composition" and "formulation" are used interchangeably.

A "subject" to which administration is contemplated refers to a human (i.e., male or female of any age group, e.g., pediatric subject (e.g., infant, child, or adolescent) or adult subject (e.g., young adult, middle-aged adult, or senior adult)) or non-human animal. In certain embodiments, the non-human animal is a mammal (e.g., primate (e.g., cynomolgus monkey or rhesus monkey), commercially relevant mammal (e.g., cattle, pig, horse, sheep, goat, cat, or dog), or bird (e.g., commercially relevant bird, such as chicken, duck, goose, or turkey)). In certain embodiments, the non-human animal is a fish, reptile, or amphibian. The non-human animal may be a male or female at any stage of development. The non-human animal may be a transgenic animal or genetically engineered animal. A "patient" refers to a human subject in need of treatment of a disease. The subject may also be a plant. In certain embodiments, the plant is a land plant. In certain embodiments, the plant is a non-vascular land plant. In certain embodiments, the plant is a vascular land plant. In certain embodiments, the plant is a seed plant. In certain embodiments, the plant is a cultivated plant. In certain embodiments, the plant is a dicot. In certain embodiments, the plant is a monocot. In certain embodiments, the plant is a flowering plant. In some embodiments, the plant is a cereal plant, e.g., maize, corn, wheat, rice, oat, barley, rye, or millet. In some embodiments, the plant is a legume, e.g., a bean plant, e.g., soybean plant. In some embodiments, the plant is a tree or shrub.

The term "biological sample" refers to any sample including tissue samples (such as tissue sections and needle biopsies of a tissue); cell samples (e.g., cytological smears (such as Pap or blood smears) or samples of cells obtained by microdissection); samples of whole organisms (such as samples of yeasts or bacteria); or cell fractions, fragments or organelles (such as obtained by lysing cells and separating the components thereof by centrifugation or otherwise). Other examples of biological samples include blood, serum, urine, semen, fecal matter, cerebrospinal fluid, interstitial fluid, mucous, tears, sweat, pus, biopsied tissue (e.g., obtained by a surgical biopsy or needle biopsy), nipple aspirates, milk, vaginal fluid, saliva, swabs (such as buccal swabs), or any material containing biomolecules that is derived from a first biological sample.

The terms "administer," "administering," or "administration" refers to implanting, absorbing, ingesting, injecting, inhaling, or otherwise introducing a compound described herein, or a composition thereof, in or on a subject.

The terms "treatment," "treat," and "treating" refer to reversing, alleviating, delaying the onset of, or inhibiting the progress of a disease described herein. In some embodiments, treatment may be administered after one or more signs or symptoms of the disease have developed or have been observed. In other embodiments, treatment may be administered in the absence of signs or symptoms of the disease. For example, treatment may be administered to a susceptible subject prior to the onset of symptoms (e.g., in light of a history of symptoms and/or in light of exposure to a pathogen). Treatment may also be continued after symptoms have resolved, for example, to delay or prevent recurrence.

The term "prevent," "preventing," or "prevention" refers to a prophylactic treatment of a subject who is not and was not with a disease but is at risk of developing the disease or who was with a disease, is not with the disease, but is at risk of regression of the disease. In certain embodiments, the subject is at a higher risk of developing the disease or at a higher risk of regression of the disease than an average healthy member of a population.

The terms "condition," "disease," and "disorder" are used interchangeably.

An "effective amount" of a compound described herein refers to an amount sufficient to elicit the desired biological response. An effective amount of a compound described herein may vary depending on such factors as the desired biological endpoint, the pharmacokinetics of the compound, the condition being treated, the mode of administration, and the age and health of the subject. In certain embodiments, an effective amount is a therapeutically effective amount. In certain embodiments, an effective amount is a prophylactic treatment. In certain embodiments, an effective amount is the amount of a compound described herein in a single dose. In certain embodiments, an effective amount is the combined amounts of a compound described herein in multiple doses. When an effective amount of a composition is referred herein, it means the amount is prophylactically and/or therapeutically effective, depending on the subject and/or the disease to be treated. Determining the effective amount or dosage is within the abilities of one skilled in the art.

A "therapeutically effective amount" of a compound described herein is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms, signs, or causes of the condition, and/or enhances the therapeutic efficacy of another therapeutic agent.

A "prophylactically effective amount" of a compound described herein is an amount effective to prevent a condition, or one or more symptoms associated with the condition or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent.

An "antigen" refers to an entity that is bound by an antibody or receptor, or an entity that induces the production of the antibody. In some embodiments, an antigen increases the production of antibodies that specifically bind the antigen. In some embodiments, an antigen comprises a protein or polypeptide. Such proteins or peptides are referred to herein as "immunogenic polypeptide." In some embodiments, the term "antigen" encompasses nucleic acids (e.g., DNA or RNA molecules) that encode immunogenic polypeptides. In some embodiments, the antigen is from a microbial pathogen. For example, the antigen may comprise parts (coats, capsules, cell walls, flagella, fimbriae, and toxins) of bacteria, viruses, fungi, and other microorganisms. In some embodiments, the antigen is a cancer-specific antigen.

Being "immunogenic" means that the composition elicits immune response when administered to a subject (e.g., a mammalian subject such as a human). As used herein, an "immune response" refers to a response by a cell of the immune system, such as a B cell, T cell (CD4 or CD8), regulatory T cell, antigen-presenting cell, dendritic cell, monocyte, macrophage, NKT cell, NK cell, basophil, eosinophil, or neutrophil, to a stimulus (e.g., to an antigen or an adjuvant). As used herein, an "immune response" refers to a response by a cell of the immune system, such as an antigen-presenting cell, dendritic cell, monocyte, macrophage, NKT cell, NK cell, basophil, eosinophil, or neutrophil, B cell, T cell (CD4 or CD8), regulatory T cell, antigen-presenting cell, dendritic cell, monocyte, macrophage, NKT cell, NK cell, basophil, eosinophil, or neutrophil, to a stimulus (e.g., to an antigen or an adjuvant).

An "antigen-specific response" or "adaptive immune response" refers to a response by a CD4 T cell, CD8 T cell, or B cell via their antigen-specific receptor. In some embodiments, an immune response is a T cell response, such as a CD4+ response or a CD8+ response. Such responses by these cells can include, for example, cytotoxicity, proliferation, cytokine or chemokine production, trafficking, or phagocytosis, and can be dependent on the nature of the immune cell undergoing the response.

In some embodiments, an antigen-specific immune response includes both a humoral and/or a cell-mediated immune response to the antigen. A "humoral immune response" is an antibody-mediated immune response and involves the induction and generation of antibodies that recognize and bind with some affinity for the antigen in the immunogenic composition of the invention, while a "cell-mediated immune response" is one mediated by T-cells and/or other white blood cells. A "cell-mediated immune response" is elicited by the presentation of antigenic epitopes in association with Class I or Class II molecules of the major histocompatibility complex (MHC), CD1 or other non-classical MHC-like molecules. This activates antigen-specific CD4+T helper cells or CD8+ cytotoxic lymphocyte cells ("CTLs"). CTLs have specificity for peptide antigens that are presented in association with proteins encoded by classical or non-classical MHCs and expressed on the surfaces of cells. CTLs help induce and promote the intracellular destruction of intracellular microbes, or the lysis of cells infected with such microbes. Another aspect of cellular immunity involves an antigen-specific response by helper T-cells. Helper T-cells act to help stimulate the function, and focus the activity of, nonspecific effector cells against cells displaying peptide or other antigens in association with classical or non-classical MHC molecules on their surface. A "cell-mediated immune response" also refers to the production of cytokines, chemokines and other such molecules produced by activated T-cells and/or other white blood cells, including those derived from CD4+ and CD8+ T-cells. The ability of a particular antigen or composition to stimulate a cell-mediated immunological response may be determined by a number of assays, such as by lymphoproliferation (lymphocyte activation) assays, CTL cytotoxic cell assays, by assaying for T-lymphocytes specific for the antigen in a sensitized subject, or by measurement of cytokine production by T cells in response to re-stimulation with antigen. Such assays are well known in the art. See, e.g., Erickson et al. (1993) J. Immunol. 151:4189-4199; and Doe et al. (1994) Eur. J. Immunol. 24:2369-2376.

In some embodiments, the immune response elicited by the composition described herein is an innate immune response. An "innate immune response" refers to the response by the innate immune system. The innate immune system uses a set of germline-encoded receptors ("pattern recognition receptor" or "PRR") for the recognition of conserved molecular patterns present in microorganisms. These molecular patterns occur in certain constituents of microorganisms including: lipopolysaccharides, peptidoglycans, lipoteichoic acids, phosphatidyl cholines, bacteria-specific proteins, including lipoproteins, bacterial DNAs, viral single and double-stranded RNAs, unmethylated CpG-DNAs, mannans and a variety of other bacterial and fungal cell wall components. Such molecular patterns can also occur in other molecules such as plant alkaloids. These targets of innate immune recognition are called Pathogen Associated Molecular Patterns (PAMPs) since they are produced by microorganisms and not by the infected host organism. In some embodiments, the innate immune response elicited by the composition described herein confers heterologous ("non-specific") immunity to a broad range of pathogenic microbes by enhancing innate immune responses to subsequent stimuli, a phenomenon known as "trained immunity", a form of innate memory, e.g., as described in Netea et al. (Trained Immunity: An Ancient Way of Remembering. Cell Host Microbe. 2017 Mar. 8; 21 (3): 297-300, incorporated herein by reference).

An "adjuvant" refers to a pharmacological or immunological agent that modifies the effect of other agents, for example, of an antigen in a vaccine. Adjuvants are typically included in vaccines to enhance the recipient subject's immune response to an antigen. The use of adjuvants allows the induction of a greater immune response in a subject with the same dose of antigen, or the induction of a similar level of immune response with a lower dose of injected antigen. Adjuvants that are known to those of skill in the art, include, without limitation: aluminum salts, liposomes, lipopolysaccharide (LPS), molecular cages for antigen, components of bacterial cell walls, endocytosed nucleic acids such as double-stranded RNA (dsRNA), single-stranded DNA (ssDNA), and unmethylated CpG dinucleotide-containing DNA. Adjuvants are thought to function in several ways, for example, but not limited to, increasing the surface area of antigen, prolonging the retention of the antigen in the body thus allowing time for the lymphoid system to have access to the antigen, slowing the release of antigen, targeting antigen to macrophages, activating macrophages, activating leukocytes such as antigen-presenting cells (e.g., monocytes, macrophages, and/or dendritic cells), or otherwise eliciting broad activation of the cells of the immune system see, e.g., H. S. Warren et al, Annu. Rev. Immunol., 4:369 (1986), incorporated herein by reference. Heterologous immunity refers to the phenomenon whereby a history of an immune response against a stimulus or pathogen can provide a level of immunity to a second unrelated stimulus or pathogen (e.g., as described in Chen et al., Virology 2015 482:89-97, incorporated herein by reference). For example, an antigen that induces cross-reactive memory CD8+ T cells against multiple unrelated viruses such as influenza A and Epstein-Barr Virus (EBV), as described in Watkin et al., J Allerg Clin Immunol 2017 October; 140 (4) 1206-1210, incorporated herein by reference. In some embodiments, the compounds described herein induce and/or enhance the heterologous protection.

The ability of an adjuvant to induce and increase a specific type of immune response and the identification of that ability is thus a key factor in the selection of particular adjuvants for vaccine use against a particular pathogen. Adjuvants that are known to those of skill in the art, include, without limitation: aluminum salts (referred to herein as "alum"), liposomes, lipopolysaccharide (LPS) or its derivatives such as monophosphoryl lipid A (MPLA), molecular cages for antigen, components of bacterial cell walls, endocytosed nucleic acids such as double-stranded RNA (dsRNA), single stranded RNA (ssRNA), single-stranded DNA (ssDNA), and unmethylated CpG dinucleotide-containing DNA. Typical adjuvants include water and oil emulsions, e.g., Freund's adjuvant and MF59, and chemical compounds such as aluminum hydroxide or alum. At present, currently licensed vaccines in the United states contain only a limited number of adjuvants, such as alum that enhances production of TH 2 cells and MPLA which activates innte immunity via Toll-like receptor 4 (TLR4). Many of the most effective adjuvants include bacteria or their products, e.g., microorganisms such as the attenuated strain of *Mycobacterium bovis, Bacillus* Calmette-Guérin (BCG); microorganism components, e.g., alum-precipitated diphtheria toxoid, bacterial lipopolysaccharide and endotoxins or their derivatives such as MPLA.

As used herein, the term "infectious disease" refers to an illness caused by a pathogenic biological agent that results from transmission from an infected person, animal, or reservoir to a susceptible host, either directly or indirectly, through an intermediate plant or animal host, vector, or inanimate environment. See Last J M. ed. A dictionary of epidemiology. 4th ed., New York: Oxford University Press, 1988. Infectious disease is also known as transmissible disease or communicable disease. In certain embodiments, infectious diseases may be asymptomatic for much or even all of their course in a given host. Infectious pathogens include some viruses, bacteria, fungi, protozoa, multicellular parasites, and aberrant proteins known as prions.

A "proliferative disease" refers to a disease that occurs due to abnormal growth or extension by the multiplication of cells (Walker, Cambridge Dictionary of Biology; Cambridge University Press: Cambridge, UK, 1990). A proliferative disease may be associated with: 1) the pathological proliferation of normally quiescent cells; 2) the pathological migration of cells from their normal location (e.g., metastasis of neoplastic cells); 3) the pathological expression of proteolytic enzymes such as the matrix metalloproteinases (e.g., collagenases, gelatinases, and elastases); or 4) the pathological angiogenesis as in proliferative retinopathy and tumor metastasis. Exemplary proliferative diseases include cancers (i.e., "malignant neoplasms"), benign neoplasms, angiogenesis, inflammatory diseases, and autoimmune diseases.

The term "angiogenesis" refers to the physiological process through which new blood vessels form from pre-existing vessels. Angiogenesis is distinct from vasculogenesis, which is the de novo formation of endothelial cells from mesoderm cell precursors. The first vessels in a developing embryo form through vasculogenesis, after which angiogenesis is responsible for most blood vessel growth during normal or abnormal development. Angiogenesis is a vital process in growth and development, as well as in wound healing and in the formation of granulation tissue. However, angiogenesis is also a fundamental step in the transition of tumors from a benign state to a malignant one, leading to the use of angiogenesis inhibitors in the treatment of cancer. Angiogenesis may be chemically stimulated by angiogenic proteins, such as growth factors (e.g., VEGF). "Pathological angiogenesis" refers to abnormal (e.g., excessive or insufficient) angiogenesis that amounts to and/or is associated with a disease.

The terms "neoplasm" and "tumor" are used herein interchangeably and refer to an abnormal mass of tissue wherein the growth of the mass surpasses and is not coordinated with the growth of a normal tissue. A neoplasm or tumor may be "benign" or "malignant," depending on the following characteristics: degree of cellular differentiation (including morphology and functionality), rate of growth, local invasion, and metastasis. A "benign neoplasm" is generally well differentiated, has characteristically slower growth than a malignant neoplasm, and remains localized to the site of origin. In addition, a benign neoplasm does not have the capacity to infiltrate, invade, or metastasize to distant sites. Exemplary benign neoplasms include, but are not limited to, lipoma, chondroma, adenomas, acrochordon, senile angiomas, seborrheic keratoses, lentigos, and sebaceous hyperplasias. In some cases, certain "benign" tumors may later give rise to malignant neoplasms, which may result from additional genetic changes in a subpopulation of the tumor's neoplastic cells, and these tumors are referred to as "pre-malignant neoplasms." An exemplary pre-malignant neoplasm is a teratoma. In contrast, a "malignant neoplasm" is generally poorly differentiated (anaplasia) and has characteristically rapid growth accompanied by progressive infiltration, invasion, and destruction of the surrounding tissue. Furthermore, a malignant neoplasm generally has the capacity to metastasize to distant sites. The term "metastasis," "metastatic," or "metastasize" refers to the spread or migration of cancerous cells from a primary or original tumor to another organ or tissue and is typically identifiable by the presence of a "secondary tumor" or "secondary cell mass" of the tissue type of the primary or original tumor and not of that of the organ or tissue in which the secondary (metastatic) tumor is located. For example, a prostate cancer that has migrated to bone is said to be metastasized prostate cancer and includes cancerous prostate cancer cells growing in bone tissue.

The term "cancer" refers to a class of diseases characterized by the development of abnormal cells that proliferate uncontrollably and have the ability to infiltrate and destroy normal body tissues. See, e.g., *Stedman's Medical Dictionary*, 25th ed.; Hensyl ed.; Williams & Wilkins: Philadelphia, 1990. Exemplary cancers include, but are not limited to, hematological malignancies. Additional exemplary cancers include, but are not limited to, lung cancer (e.g., bronchogenic carcinoma, small cell lung cancer (SCLC), non-small cell lung cancer (NSCLC), adenocarcinoma of the lung); kidney cancer (e.g., nephroblastoma, a.k.a. Wilms' tumor, renal cell carcinoma); acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma); choriocarcinoma; chordoma; craniopharyngioma; colorectal cancer (e.g., colon cancer, rectal cancer, colorectal adenocarcinoma); connective tissue cancer; epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarcinoma); Ewing's sarcoma; ocular cancer (e.g., intraocular melanoma, retinoblastoma); familiar hypereosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); heavy chain disease (e.g., alpha chain disease, gamma chain disease, mu chain disease; hemangioblastoma; hypopharynx cancer; inflammatory myofibroblastic tumors; immunocytic amyloidosis; liver cancer (e.g., hepatocellular cancer (HCC), malignant hepatoma); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendoctrine tumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic andenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva). In some embodiments, the cancer treated using the composition and methods of the present disclosure is melanoma.

The term "inflammatory disease" refers to a disease caused by, resulting from, or resulting in inflammation. The term "inflammatory disease" may also refer to a dysregulated inflammatory reaction that causes an exaggerated response by macrophages, granulocytes, and/or T-lymphocytes leading to abnormal tissue damage and/or cell death. An inflammatory disease can be either an acute or chronic inflammatory condition and can result from infections or non-infectious causes. Inflammatory diseases include, without limitation, atherosclerosis, arteriosclerosis, autoimmune disorders, multiple sclerosis, systemic lupus erythematosus, polymyalgia rheumatica (PMR), gouty arthritis, degenerative arthritis, tendonitis, bursitis, psoriasis, cystic fibrosis, arthrosteitis, rheumatoid arthritis, inflammatory arthritis, Sjogren's syndrome, giant cell arteritis, progressive systemic sclerosis (scleroderma), ankylosing spondylitis, polymyositis, dermatomyositis, pemphigus, pemphigoid, diabetes (e.g., Type I), myasthenia gravis, Hashimoto's thyroiditis, Graves' disease, Goodpasture's disease, mixed connective tissue disease, sclerosing cholangitis, inflammatory bowel disease, Crohn's disease, ulcerative colitis, pernicious anemia, inflammatory dermatoses, usual interstitial pneumonitis (UIP), asbestosis, silicosis, bronchiectasis, berylliosis, talcosis, pneumoconiosis, sarcoidosis, desquamative interstitial pneumonia, lymphoid interstitial pneumonia, giant cell interstitial pneumonia, cellular interstitial pneumonia, extrinsic allergic alveolitis, Wegener's granulomatosis and related forms of angiitis (temporal arteritis and polyarteritis nodosa), inflammatory dermatoses, hepatitis, delayed-type hypersensitivity reactions (e.g., poison ivy dermatitis), pneumonia, respiratory tract inflammation, Adult Respiratory Distress Syndrome (ARDS), encephalitis, immediate hypersensitivity reactions, asthma, hayfever, allergies, acute anaphylaxis, rheumatic fever, glomerulonephritis, pyelonephritis, cellulitis, cystitis, chronic cholecystitis, ischemia (ischemic injury), reperfusion injury, appendicitis, arteritis, blepharitis, bronchiolitis, bronchitis, cervicitis, cholangitis, chorioamnionitis, conjunctivitis, dacryoadenitis, dermatomyositis, endocarditis, endometritis, enteritis, enterocolitis, epicondylitis, epididymitis, fasciitis, fibrositis, gastritis, gastroenteritis, gingivitis, ileitis, iritis, laryngitis, myelitis, myocarditis, nephritis, omphalitis, oophoritis, orchitis, osteitis, otitis, pancreatitis, parotitis, pericarditis, pharyngitis, pleuritis, phlebitis, pneumonitis, proctitis, prostatitis, rhinitis, salpingitis, sinusitis, stomatitis, synovitis, testitis, tonsillitis, urethritis, urocystitis, uveitis, vaginitis, vasculitis, vulvitis, vulvovaginitis, angitis, chronic bronchitis, osteomyelitis, optic neuritis, temporal arteritis, transverse myelitis, necrotizing fasciitis, and necrotizing enterocolitis. An ocular inflammatory disease includes, but is not limited to, post-surgical inflammation.

An "autoimmune disease" refers to a disease arising from an inappropriate immune response of the body of a subject against substances and tissues normally present in the body. In other words, the immune system mistakes some part of the body as a pathogen and attacks its own cells. This may be restricted to certain organs (e.g., in autoimmune thyroiditis) or involve a particular tissue in different places (e.g., Goodpasture's disease which may affect the basement membrane in both the lung and kidney). The treatment of autoimmune diseases is typically with immunosuppression, e.g., medications which decrease the immune response. Exemplary autoimmune diseases include, but are not limited to, glomerulonephritis, Goodpasture's syndrome, necrotizing vasculitis, lymphadenitis, peri-arteritis nodosa, systemic lupus erythematosis, rheumatoid arthritis, psoriatic arthritis, systemic lupus erythematosis, psoriasis, ulcerative colitis, systemic sclerosis, dermatomyositis/polymyositis, anti-phospholipid antibody syndrome, scleroderma, pemphigus vulgaris, ANCA-associated vasculitis (e.g., Wegener's granulomatosis, microscopic polyangiitis), uveitis, Sjogren's syndrome, Crohn's disease, Reiter's syndrome, ankylosing spondylitis, Lyme disease, Guillain-Barre syndrome, Hashimoto's thyroiditis, and cardiomyopathy.

A "chronic disease" refers to a disease lasting for three or more months. Exemplary chronic diseases include, but are not limited to, arthritis, cardiovascular disease such as heart disease, stroke, cancer (e.g., breast cancer or colon cancer), chronic respiratory diseases, diabetes, epilepsy, seizures, obesity, and oral health problems.

A "vaccine" or "vaccine composition" refers to a composition that activates or enhances a subject's immune response to an antigen after the vaccine is administered to the subject.

BRIEF DESCRIPTION OF THE DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

(FIG. 1B). The positive control R848 is labelled. NF-κB activation was measured by quantifying the luminescence from the secreted luciferase enzyme in cell-free supernatants. The five most effective compounds (003, 004, 005, 070 and 080, depicted in blue) share some structural similarity. N=1-2.

FIG. 2. Compounds 004, 007, and 080 are rare screen positives. The figure depicts the total number of times compounds 004, 070 and 080 have been screened (134, 59 and 39 times, respectively) and the number of screening campaigns that identified these compounds as positive hits (3, 1 and 1, respectively). These data suggest that these compounds are likely true positives, not pan assay interference compounds.

(FIG. 4A) Results are expressed as mean±SEM of N=3. (FIGS. 4B and 4C) TNF production at the top concentration of compound 004 and other THP1-NF-κB hits plotted against the inverse of the EC50, highlighting compounds with favorable efficacy and potency. Each graph is representative of an individual adult donor.

FIG. 8. Compound 080 analog activities on THP1-NF-κB cells. THP1-NF-κB cells were stimulated for 24 hours with compound 080, its analogs (80.1-80.15), published known TLR2 agonists (e.g., the "Tappling molecules (TM)" in Guan et al., J Biol Chem 2010; 285:23755-23762), including TM-A, TM-B, TM-C, TM-E and TM-F, and the TLR2 agonist P3CSK4 at the indicated concentrations. NF-kB activation was measured by quantifying the luminescence from the secreted luciferase enzyme in cell-free supernatants. Results are shown as the median, the 25th and 75th percentiles (boxes) and the 5th and 95th percentiles (whiskers) of N=4.

FIG. 11C-11D show that compounds 080, 080.3, 080.10, 080.15 induced TLR2 specific activation, without induction of TLR8, in a titratable dependent fashion in vitro (FIG. 11E).

DETAILED DESCRIPTION OF CERTAIN EMBODIMENTS

Figure 1A:
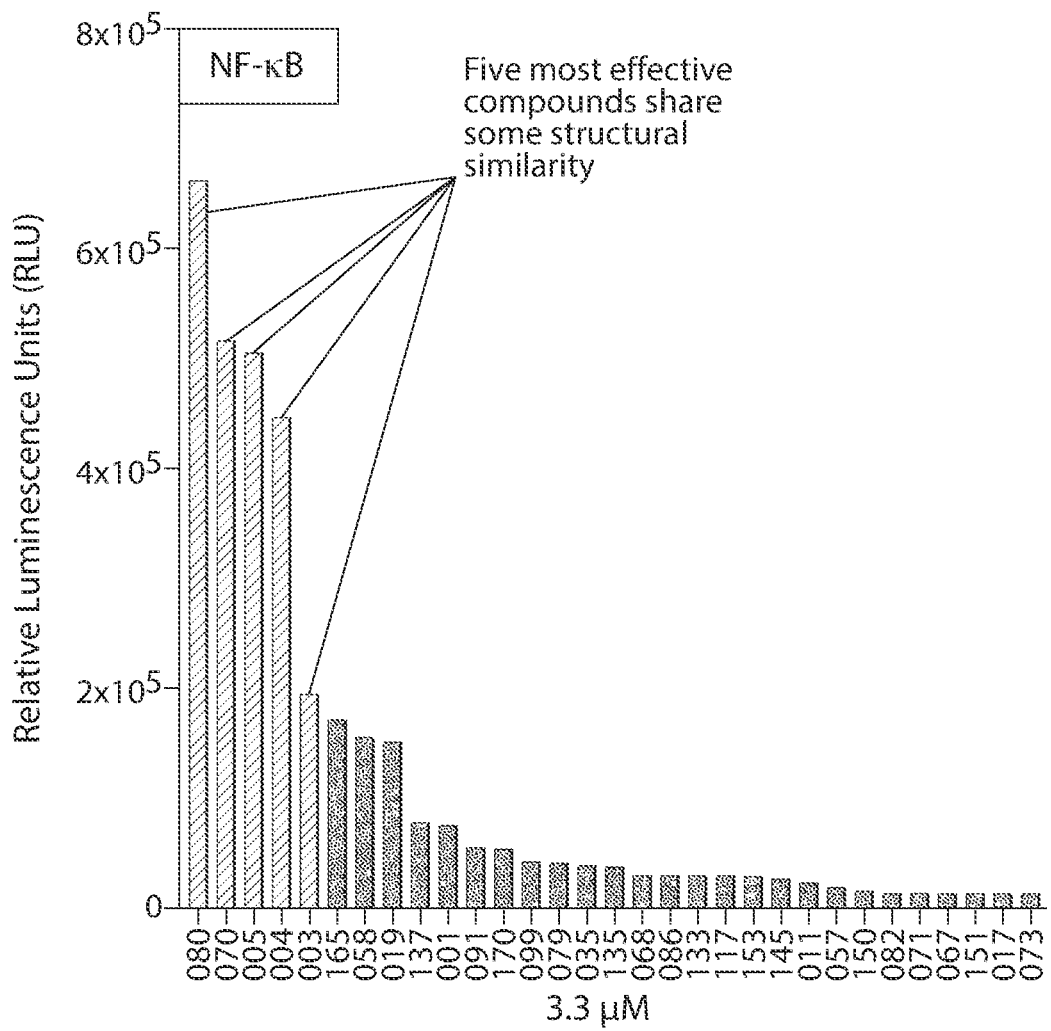
FIGS. 1A-1B. Efficacy and potency of potency of NF-κB-activating THP1 screening hits. The top 31 THP1 screening hits were ranked based on efficacy in activating NF-κB at 3.3 µM (FIG. 1A) and assessed for potency across a concentration range (0.05 µM-33 µM).

Some aspects of the present disclosure are based, at least in part, on the finding that Toll-like receptor 2 (TLR2) agonists induce robust activation of human leukocytes in vitro and act as adjuvants in vivo. As described herein, TLR2 agonists may be used for modifying human immune responses, including innate and adaptive immune responses. In some embodiments, the TLR2 agonists are used as adjuvants in vaccines. Adjuvants can enhance, prolong, and modulate immune responses to vaccinal antigens to maximize protective immunity. In some aspects, using TLR2 agonists as vaccine adjuvants enable effective immunization in vulnerable populations (e.g., neonates, elderly, or immunocompromised individuals). In some embodiments, the TLR2 agonists are used in the treatment (both prophylactically or therapeutically) of infectious diseases, cancer, or allergy. In some embodiments, the TRL-2 agonist is a thiophene.

Toll-Like Receptor 2 (TLR2) Agonists

Some aspects of the present disclosure provide compositions comprising an antigen and a TLR2 agonist. "Toll-like receptor 2" refers to a protein that in human is encoded by the TLR2 gene, also designated cluster of differentiation 282 (CD282). TLR2 is one of the Toll-like receptors and plays a role in the immune system. TLR2 is a membrane protein expressed on the surface of certain cells and recognizes foreign substances and passes on appropriate signals to the cells of the immune system. Toll-like receptor 2 (TLR2) is required for recognition of diverse microbial molecules from broad groups of species such as Gram-positive and Gram-negative bacteria, as well as mycoplasma and yeast. Specifically, TLR2 is involved in the recognition of cell-wall components, lipoteichoic acid and lipoprotein, from gram-positive bacteria; lipoarabinomannan, from mycobacteria; and zymosan, from yeast. TLR2 is involved in the specific recognition of a wide range of ligands, either as a homodimer or as a heterodimer with TLR1 or TLR6.

An "agonist" refers to a substance that initiates a physiological response when combined with a receptor. A "TLR2 agonist," as used herein, encompasses any molecule that bind to TLR2 and activates TLR2 to produce a biological response. A TLR2 agonist may be, e.g., without limitation, a protein, a nucleic acid (e.g., DNA or RNA), a small molecule, a lipid, or a polysacharride. For example, TLR2 can be activated by substances found in microbial pathogens such as microbial proteins or surface molecules (e.g., lipopolysaccharides). Such microbial proteins or surface molecules can be used as TLR2 agonists.

In some embodiments, the TLR2 agonist is a small molecule. A "small molecule," as used herein, refers to an organic compound, whether naturally-occurring or artificially created (e.g., via chemical synthesis) that has a relatively low molecular weight. Typically, an organic compound contains carbon. An organic compound may contain multiple carbon-carbon bonds, stereocenters, and other functional groups (e.g., amines, hydroxyl, carbonyls, or heterocyclic rings). In some embodiments, small molecules are monomeric organic compounds that have a molecular weight of less than about 1500 g/mol. In some embodiments, the molecular weight of the small molecule is less than about 1000 g/mol or less than about 500 g/mol. In some embodiments, the small molecule is a drug, for example, a drug that has already been deemed safe and effective for use in humans or animals by the appropriate governmental agency or regulatory body. Small molecule TLR2 agonists that have been described in the art (e.g., in Guan et al., The Journal of Biological Chemistry, vol. 285, No. 31, pp. 23755-23762, 2010, incorporated herein by reference) can be used in accordance with the present disclosure.

In some embodiments, the TLR2 agonist is a thiophene. In one aspect, the thiophene comprises a compound of Formula (I):

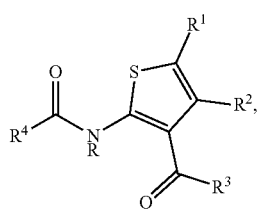

(I)

and pharmaceutically acceptable salts, solvates, hydrates, polymorphs, co-crystals, tautomers, stereoisomers, isotopically labeled derivatives, and prodrugs thereof, wherein:

$R^1$ is hydrogen or optionally substituted alkyl;

$R^2$ is hydrogen or optionally substituted alkyl; or optionally, $R^1$ and $R^2$ are joined together with the intervening atoms to form a substituted or unsubstituted carbocyclic ring, substituted or unsubstituted heterocyclic ring, substituted or unsubstituted aryl ring, or substituted or unsubstituted heteroaryl ring;

$R^3$ is hydrogen, halogen, optionally substituted alkyl, $-OR^{a1}$, or $-N(R^{a2})_2$, wherein $R^{a1}$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group when attached to an oxygen atom;

wherein each occurrence of $R^{a2}$ is independently hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group;

R is hydrogen or optionally substituted alkyl;

X is O or S; and $R^4$ is hydrogen, optionally substituted alkyl, optionally substituted carbocyclyl, optionally substituted heterocyclyl, optionally substituted aryl, optionally substituted heteroaryl, or $-N(R^{a2})_2$.

Formula (I) includes substituent $R^1$. In certain embodiments, $R^1$ is hydrogen. In certain embodiments, $R^1$ is optionally substituted alkyl (e.g., substituted or unsubstituted $C_{1-6}$ alkyl (e.g., substituted or unsubstituted Me or substituted or unsubstituted Et)). In certain embodiments, $R^1$ is optionally substituted $C_{1-6}$ alkyl. In certain embodiments, $R^1$ is substituted or unsubstituted Me. In certain embodiments, $R^1$ is unsubstituted Me.

Formula (I) includes substituent $R^2$. In certain embodiments, $R^2$ is hydrogen. In certain embodiments, $R^2$ is optionally substituted alkyl (e.g., substituted or unsubstituted $C_{1-6}$ alkyl (e.g., substituted or unsubstituted Me or substituted or unsubstituted Et)). In certain embodiments, $R^2$ is optionally substituted $C_{1-6}$ alkyl. In certain embodiments, $R^2$ is substituted or unsubstituted Me. In certain embodiments, $R^2$ is unsubstituted Me. In certain embodiments, $R^1$ is optionally substituted $C_{1-6}$ alkyl; and $R^2$ is optionally substituted $C_{1-6}$ alkyl. In certain embodiments, $R^1$ is unsubstituted Me and $R^2$ is unsubstituted Me.

In certain embodiments, $R^1$ and $R^2$ are joined together with the intervening atoms to form a substituted or unsubstituted carbocyclic ring, substituted or unsubstituted heterocyclic ring, substituted or unsubstituted aryl ring, or substituted or unsubstituted heteroaryl ring. In certain embodiments, $R^1$ and $R^2$ are joined together with the intervening atoms to form a substituted or unsubstituted 5-membered carbocyclic ring, substituted or unsubstituted 6-membered carbocyclic ring, or substituted or unsubstituted 7-membered carbocyclic ring. In certain embodiments, $R^1$ and $R^2$ are joined together with the intervening atoms to form a substituted or unsubstituted 5-membered carbocyclic ring. In certain embodiments, $R^1$ and $R^2$ are joined together with the intervening atoms to form a substituted or unsubstituted 6-membered carbocyclic ring. In certain embodiments, $R^1$ and $R^2$ are joined together with the intervening atoms to form a substituted or unsubstituted 7-membered carbocyclic ring. In certain embodiments, R¹ and R² are joined together with the intervening atoms to form a substituted or unsubstituted 6-membered heterocyclic ring containing one nitrogen. In certain embodiments, R¹ and R² are joined together with the intervening atoms to form a substituted or unsubstituted 6-membered heterocyclic ring containing one oxygen. In certain embodiments, R¹ and R² are joined together with the intervening atoms to form substituted or unsubstituted tetrahydropyran. In certain embodiments, R¹ and R² are joined together with the intervening atoms to form substituted or unsubstituted 3,6-dihydro-2H-pyran.

Formula (I) includes substituent R³. In certain embodiments, R³ is hydrogen. In certain embodiments, R³ is optionally substituted alkyl (e.g., substituted or unsubstituted $C_{1-6}$ alkyl (e.g., substituted or unsubstituted Me or substituted or unsubstituted Et)). In certain embodiments, R³ is optionally substituted $C_{1-6}$ alkyl. In certain embodiments, R³ is halogen. In certain embodiments, R³ is F. In certain embodiments, R³ is Br. In certain embodiments, R³ is Cl. In certain embodiments, R³ is I. In certain embodiments, R³ is —$OR^{a1}$ (e.g., —OH, —O (substituted or unsubstituted $C_{1-6}$ alkyl) (e.g., —OMe, —OEt, —OPr, —OBu, or —OBn). In certain embodiments, R³ is —$N(R^{a2})_2$ (e.g., —$NH_2$, —NH (substituted or unsubstituted $C_{1-6}$ alkyl) (e.g., —NHMe), or —N(substituted or unsubstituted $C_{1-6}$ alkyl)-(substituted or unsubstituted $C_{1-6}$ alkyl) (e.g., —$NMe_2$)). In certain embodiments, $R^{a1}$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group when attached to an oxygen atom. In certain embodiments, each occurrence of $R^{a2}$ is independently hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group.

Formula (I) includes substituent R⁴. In certain embodiments, R⁴ is hydrogen. In certain embodiments, R⁴ is optionally substituted alkyl (e.g., substituted or unsubstituted $C_{1-6}$ alkyl (e.g., substituted or unsubstituted Me or substituted or unsubstituted Et)). In certain embodiments, R⁴ is optionally substituted $C_{1-6}$ alkyl. In certain embodiments, R⁴ is optionally substituted methyl. In certain embodiments, R⁴ is substituted methyl. In certain embodiments, R⁴ is of the formula —$CH_2(R^{4a})$, wherein $R^{4a}$ is substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, R⁴ is of the formula

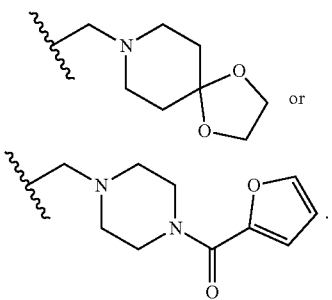

or

In certain embodiments, $R^{4a}$ is substituted or unsubstituted 6-membered heterocyclic ring, wherein one or two atoms in the heterocyclic ring are nitrogen.

In certain embodiments, R⁴ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, R⁴ is substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, R⁴ is substituted or unsubstituted aryl (e.g., substituted or unsubstituted, 6- to 10-membered aryl). In certain embodiments, R⁴ is optionally substituted phenyl. In certain embodiments, R⁴ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, R⁴ is optionally substituted 5-membered heteroaryl. In certain embodiments, R⁴ is —$N(R^{a2})_2$ (e.g., —$NH_2$, —NH(substituted or unsubstituted $C_{1-6}$ alkyl) (e.g., —NHMe), or —$NMe_2$). In certain embodiments, R⁴ is optionally substituted $C_{1-6}$ alkyl, optionally substituted 5-membered heteroaryl, or optionally substituted phenyl.

Formula (I) includes substituent X. In certain embodiments, X is O. In certain embodiments, X is S.

Formulae (I) and (III) include substituent R. In certain embodiments, R is hydrogen. In certain embodiments, R is optionally substituted alkyl (e.g., substituted or unsubstituted $C_{1-6}$ alkyl (e.g., substituted or unsubstituted Me or substituted or unsubstituted Et)). In certain embodiments, R is optionally substituted $C_{1-6}$ alkyl. In certain embodiments, R is optionally substituted methyl.

In certain embodiments, a compound of Formula (I) is of Formula (IA):

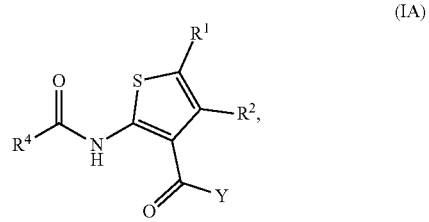

(IA)

and pharmaceutically acceptable salts, solvates, hydrates, polymorphs, co-crystals, tautomers, stereoisomers, isotopically labeled derivatives, and prodrugs thereof, wherein:

R¹ and R² are joined together with the intervening atoms to form a substituted or unsubstituted carbocyclic ring, substituted or unsubstituted heterocyclic ring, substituted or unsubstituted aryl ring, or substituted or unsubstituted heteroaryl ring;

Y is —$OR^{a1}$, or —$N(R^{a2})_2$, wherein $R^{a1}$ is optionally substituted $C_{1-6}$ alkyl; and each occurrence of $R^{a2}$ is independently hydrogen or optionally substituted $C_{1-6}$ alkyl. In certain embodiments, Y is —$OR^{a1}$. In certain embodiments, Y is —O (optionally substituted methyl) or —O (optionally substituted ethyl). In certain embodiments, Y is —O (unsubstituted methyl) or —O (unsubstituted ethyl). In certain embodiments, Y is —N(R$^{a2}$)$_2$. In certain embodiments, Y is-NH (optionally substituted C$_{1-6}$ alkyl). In certain embodiments, Y is —NH (unsubstituted methyl).

In certain embodiments, a compound of Formula (I) is of the formula:

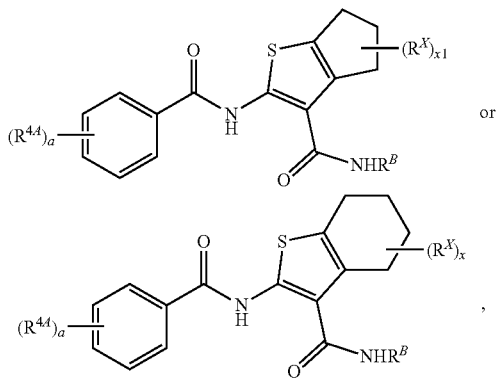

and pharmaceutically acceptable salts, solvates, hydrates, polymorphs, co-crystals, tautomers, stereoisomers, isotopically labeled derivatives, and prodrugs thereof, wherein:

R$^{4A}$ is halogen, optionally substituted alkyl, optionally substituted acyl, —SO$_2$N(R$^a$)$_2$, —OR$^b$, optionally substituted alkenyl, optionally substituted alkynyl, optionally substituted carbocyclyl, optionally substituted heterocyclyl, optionally substituted aryl, optionally substituted heteroaryl;

each instance of RX is independently hydrogen, halogen, or optionally substituted alkyl;

R$^B$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, or optionally substituted heteroaryl;

x is 0, 1, 2, 3, 4, 5, or 6;
x1 is 0, 1, 2, 3, 4, 5, or 6;
a is 0, 1, 2, 3, 4, or 5;

each instance of R$^a$ is independently hydrogen, optionally substituted alkyl, a nitrogen protecting group, or two instances of R$^a$ are joined together with the intervening atoms to form optionally substituted heterocyclyl; and R$^b$ is hydrogen, optionally substituted alkyl, or an oxygen protecting group.

In certain embodiments, a compound of Formula (I) includes one or more instances of R$^{4A}$. In certain embodiments, a is 0. In certain embodiments, a is 1. In certain embodiments, a is 2. In certain embodiments, a is 3. In certain embodiments, a is 4. In certain embodiments, a is 5.

In certain embodiments, at least one instance of R$^{4A}$ is halogen, optionally substituted alkyl, optionally substituted acyl, —SO$_2$N(R$^a$)$_2$, —OR$^b$, optionally substituted alkenyl, optionally substituted alkynyl, optionally substituted carbocyclyl, optionally substituted heterocyclyl, optionally substituted aryl, optionally substituted heteroaryl; wherein each instance of R$^a$ is independently hydrogen, optionally substituted alkyl, a nitrogen protecting group, or two instances of R$^a$ are joined together with the intervening atoms to form optionally substituted heterocyclyl; and R$^b$ is hydrogen, optionally substituted alkyl, or an oxygen protecting group.

In certain embodiments, at least one instance of R$^{4A}$ is Br, Cl, or I. In certain embodiments, at least one instance of R$^{4A}$ is Cl. In certain embodiments, at least one instance of R$^{4A}$ is —OR$^b$, wherein R$^b$ is hydrogen or optionally substituted C$_{1-6}$ alkyl. In certain embodiments, at least one instance of R$^{4A}$ is-OMe. In certain embodiments, at least one instance of R$^{4A}$ is —SO$_2$N(R$^a$)$_2$, wherein each instance of R$^a$ is independently optionally substituted C$_{1-6}$ alkyl. In certain embodiments, at least one instance of R$^{4A}$ is —SO$_2$NMe$_2$. In certain embodiments, at least one instance of R$^{4A}$ is —SO$_2$N(Et)$_2$. In certain embodiments, at least one instance of R$^{4A}$ is —SO$_2$N(R$^a$)$_2$, and two instances of R$^a$ are joined together with the intervening atoms to form optionally substituted, 5-membered heterocyclyl or optionally substituted, 6-membered heterocyclyl. In certain embodiments, at least one instance of R$^{4A}$ is —SO$_2$N(R$^a$)$_2$, and two instances of R$^a$ are joined together with the intervening atoms to form optionally substituted, 5-membered heterocyclyl. In certain embodiments, at least one instance of R$^{4A}$ is —SO$_2$N(R$^a$)$_2$, and two instances of R$^a$ are joined together with the intervening atoms to form optionally substituted pyrrolidinyl. In certain embodiments, at least one instance of R$^{4A}$ is

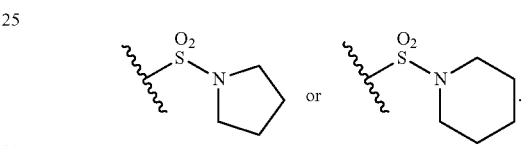

In certain embodiments, at least one instance of R$^{4A}$ is —SO$_2$N(R$^a$)$_2$, or —C(=O)R$^a$, wherein each instance of R$^a$ is independently hydrogen, optionally substituted alkyl, or a nitrogen protecting group. In certain embodiments, at least one instance of R$^{4A}$ is optionally substituted phenyl or

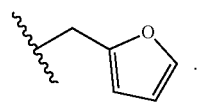

In certain embodiments, in a compound of Formula (IB), R$^{4A}$ is optionally substituted phenyl or

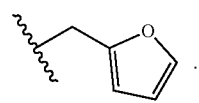

In certain embodiments, at least one instance of R$^{4A}$ is optionally substituted alkenyl (e.g., substituted or unsubstituted C$_{2-6}$ alkenyl). In certain embodiments, at least one instance of R$^{4A}$ is optionally substituted alkynyl (e.g., substituted or unsubstituted C$_{2-6}$ alkynyl). In certain embodiments, at least one instance of R$^{4A}$ is optionally substituted carbocyclyl (e.g., substituted or unsubstituted, 3- to 7-membered, monocyclic carbocyclyl comprising zero, one, or two double bonds in the carbocyclic ring system). In certain embodiments, at least one instance of R$^{4A}$ is optionally substituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, at least one instance of R$^{4A}$ is optionally substituted aryl (e.g., substituted or unsubstituted, 6- to 10-membered aryl). In certain embodiments, at least one instance of $R^{4A}$ is optionally substituted phenyl. In certain embodiments, at least one instance of $R^{4A}$ is optionally substituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur).

In certain embodiments, a compound of Formulae (I) or (III) includes one or more instances of $R^X$. In certain embodiments, x is 0. In certain embodiments, x is 1. In certain embodiments, x is 2. In certain embodiments, x is 3. In certain embodiments, x is 4. In certain embodiments, x is 5. In certain embodiments, x is 6. In certain embodiments, x1 is 0. In certain embodiments, x1 is 1. In certain embodiments, x1 is 2. In certain embodiments, x1 is 3. In certain embodiments, x1 is 4. In certain embodiments, x1 is 5. In certain embodiments, x1 is 6. In certain embodiments, at least one instance of $R^X$ is hydrogen. In certain embodiments, at least one instance of $R^X$ is halogen (e.g., Br, Cl, or I). In certain embodiments, at least one instance of $R^X$ is optionally substituted alkyl (e.g., optionally substituted $C_{1-6}$ alkyl).

In certain embodiments, a compound of Formula (I) is of the formula:

and pharmaceutically acceptable salts, solvates, hydrates, polymorphs, co-crystals, tautomers, stereoisomers, isotopically labeled derivatives, and prodrugs thereof, wherein:

$R^{4A}$ is optionally substituted alkyl, optionally substituted acyl, —SO$_2$N(R$^a$)$_2$, optionally substituted alkenyl, optionally substituted alkynyl, optionally substituted carbocyclyl, optionally substituted heterocyclyl, optionally substituted aryl, optionally substituted heteroaryl;

each instance of $R^X$ is independently hydrogen, halogen, or optionally substituted alkyl;

$R^B$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, or optionally substituted heteroaryl;

x1 is 0, 1, 2, 3, 4, 5, or 6;

a is 0, 1, 2, 3, 4, or 5; and each instance of $R^a$ is independently hydrogen, optionally substituted alkyl, or a nitrogen protecting group.

In certain embodiments, a compound of Formula (I) is of the formula:

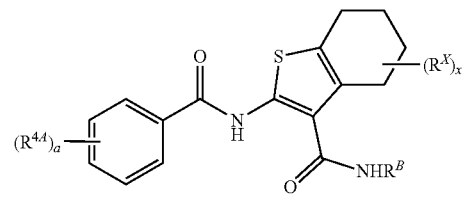

and pharmaceutically acceptable salts, solvates, hydrates, polymorphs, co-crystals, tautomers, stereoisomers, isotopically labeled derivatives, and prodrugs thereof, wherein:

$R^{4A}$ is optionally substituted alkyl, optionally substituted acyl, —SO$_2$N(R$^a$)$_2$, optionally substituted alkenyl, optionally substituted alkynyl, optionally substituted carbocyclyl, optionally substituted heterocyclyl, optionally substituted aryl, optionally substituted heteroaryl;

each instance of $R^X$ is independently hydrogen, halogen, or optionally substituted alkyl;

$R^B$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, or optionally substituted heteroaryl;

x is 0, 1, 2, 3, 4, 5, or 6;

a is 0, 1, 2, 3, 4, or 5; and each instance of $R^a$ is independently hydrogen, optionally substituted alkyl, a nitrogen protecting group, or two instances of $R^a$ are joined together with the intervening atoms to form optionally substituted heterocyclyl.

In certain embodiments, a compound of Formula (I) is of Formula (IB):

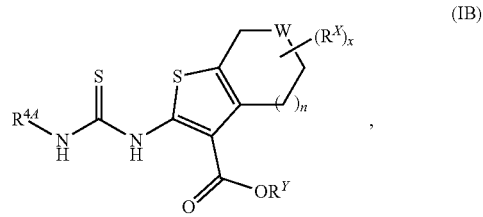
(IB)

and pharmaceutically acceptable salts, solvates, hydrates, polymorphs, co-crystals, tautomers, stereoisomers, isotopically labeled derivatives, and prodrugs thereof, wherein:

W is —C(R$^{a1}$)—, —N(R$^{a2}$)—, or —O—, wherein R$^{a1}$ is hydrogen, halogen, or optionally substituted alkyl;

each instance of $R^X$ is independently hydrogen, halogen, or optionally substituted alkyl;

x is 0, 1, 2, 3, 4, 5, or 6;

n is 0 or 1;

$R^Y$ is hydrogen or optionally substituted $C_{1-6}$ alkyl; and $R^{4A}$ is hydrogen, optionally substituted $C_{1-6}$ alkyl, optionally substituted carbocyclyl, optionally substituted heterocyclyl, or optionally substituted aryl.

Formula (IB) includes substituent W. In certain embodiments, W is —C(R$^{a1}$)—, —N(R$^{a2}$)—, or —O—, wherein R$^{a1}$ is hydrogen, halogen, or optionally substituted alkyl. In certain embodiments, W is —C(substituted or unsubstituted $C_{1-6}$ alkyl)-. In certain embodiments, W is —CH—. In certain embodiments, W is —N(R$^{a2}$)—, wherein each occurrence of R$^{a2}$ is independently hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group. In certain embodiments, W is —N(optionally substituted acyl)-. In certain embodiments, W is —N(optionally substituted alkyl)-. In certain embodiments, W is —N (optionally substituted $C_{1-6}$ alkyl)-. In certain embodiments, W is —CH— and n is 0. In certain embodiments, W is —CH— and n is 1. In certain embodiments, W is —O— and n is 1. In certain embodiments, W is —N(optionally substituted acyl)- and n is 1. In certain embodiments, W is —N(optionally substituted alkyl)- and n is 1.

In certain embodiments, n is 0. In certain embodiments, n is 1. In certain embodiments, $R^Y$ is hydrogen. In certain embodiments, $R^Y$ is optionally substituted $C_{1-6}$ alkyl. In certain embodiments, $R^Y$ is optionally substituted methyl. In certain embodiments, $R^Y$ is unsubstituted methyl. In certain embodiments, $R^Y$ is substituted methyl. In certain embodiments, $R^Y$ is optionally substituted ethyl. In certain embodiments, $R^Y$ is unsubstituted ethyl. In certain embodiments, $R^Y$ is substituted ethyl. In certain embodiments, $R^{4A}$ is hydrogen, optionally substituted $C_{1-6}$ alkyl, optionally substituted carbocyclyl, optionally substituted heterocyclyl, or optionally substituted aryl. In certain embodiments, the thiophene comprises a compound of Formula (I), and a pharmaceutically acceptable salt thereof.

In certain embodiments, a compound of Formula (I) is of the formula:

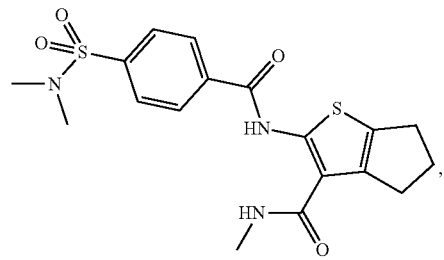
(80)

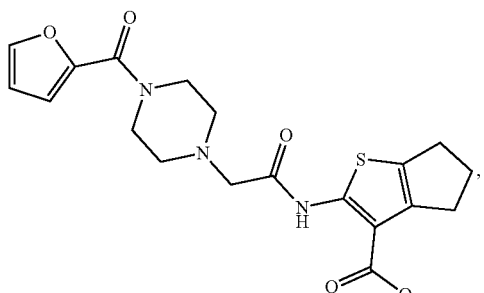
(3)

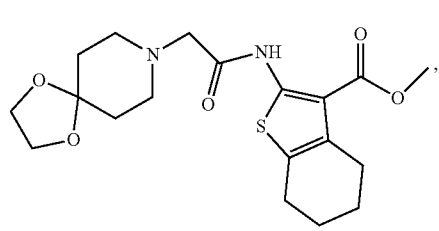
(4)

-continued

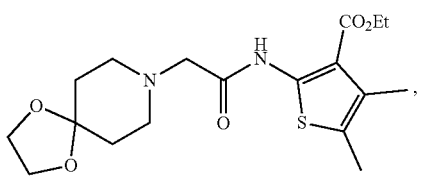
(5)

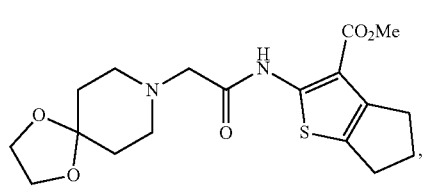
(004.19)

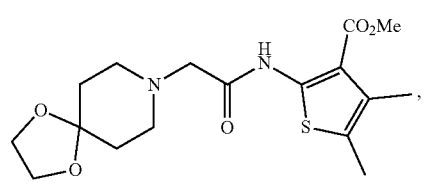
(004.20)

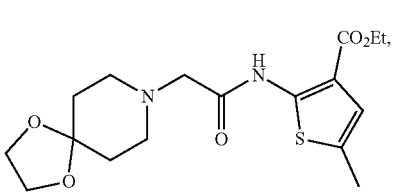
(004.18)

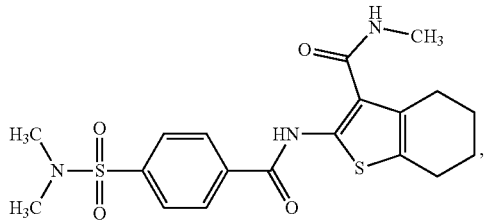
(80.3)

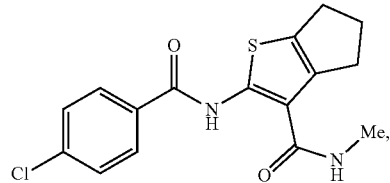
(80.5)

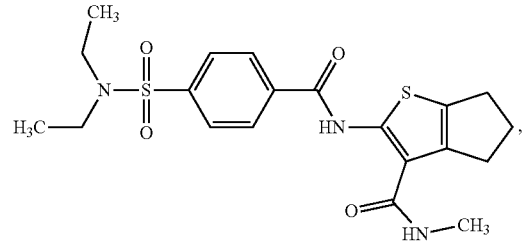
(80.6)

-continued (80.8)
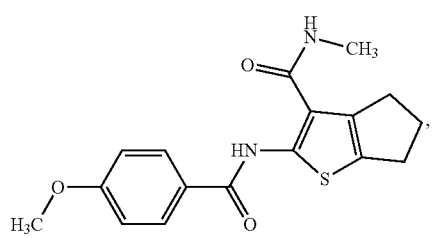

(80.10)
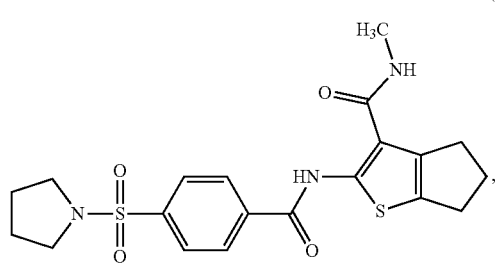

(80.11)
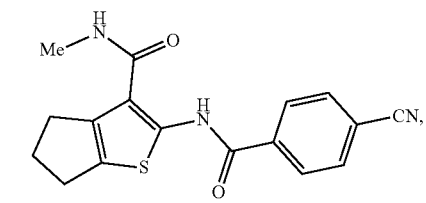

(80.13)
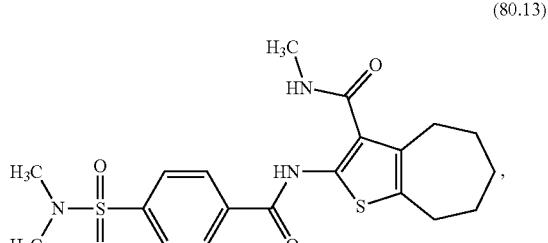

(80.14)
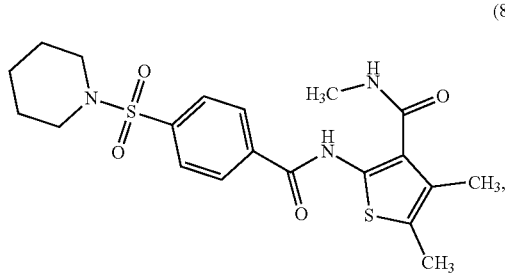

(80.15)
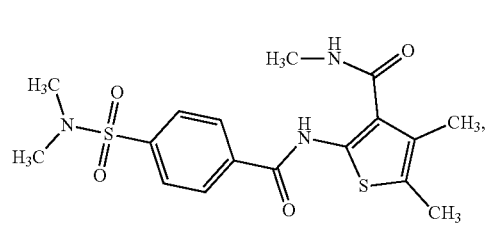

-continued

(70)
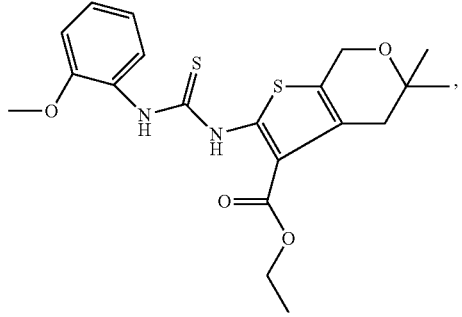

(137)
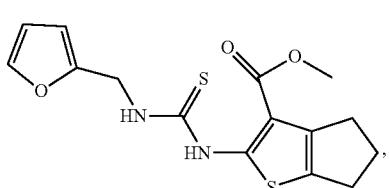

(TM-B)
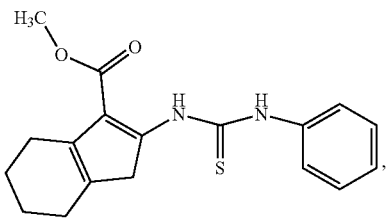

(TM-C)
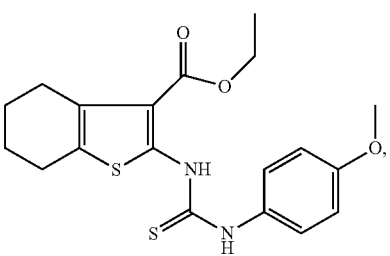

or a pharmaceutically acceptable salt, solvate, hydrate, polymorph, co-crystal, tautomer, stereoisomer, isotopically labeled derivative, or prodrug thereof.

In one aspect, the TLR2 agonist comprises a compound of Formula (II):

(II)
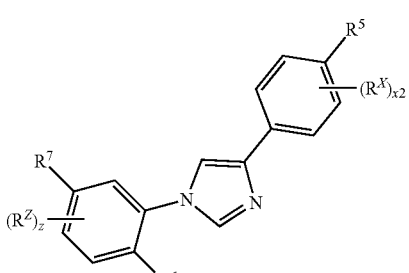

and pharmaceutically acceptable salts, solvates, hydrates, polymorphs, co-crystals, tautomers, stereoisomers, isotopically labeled derivatives, and prodrugs thereof, wherein:

$R^5$ is hydrogen, halogen, optionally substituted alkyl, —$NO_2$, —$OR^{a1}$, or —$N(R^{a2})_2$, wherein $R^{a1}$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group when attached to an oxygen atom;

wherein each occurrence of $R^{a2}$ is independently hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group;

each instance of $R^X$ is independently hydrogen, halogen, or optionally substituted alkyl;

x2 is 0, 1, 2, 3, or 4;

each instance of $R^6$ is independently hydrogen, optionally substituted acyl, optionally substituted alkyl, optionally substituted alkenyl, optionally substituted alkynyl, optionally substituted carbocyclyl, optionally substituted heterocyclyl, optionally substituted aryl, or —N($R^{6A}$)$_2$;

each instance of $R^{6A}$ is independently hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group;

$R^7$ is hydrogen, halogen, optionally substituted alkyl, —NO$_2$, —OR$^{a1}$, or —N($R^{a2}$)$_2$;

each instance of $R^7$ is independently hydrogen, halogen, or optionally substituted alkyl; and z is 0, 1, 2, or 3.

Formula (II) includes substituent $R^5$. In certain embodiments, $R^5$ is hydrogen. In certain embodiments, $R^5$ is optionally substituted alkyl (e.g., substituted or unsubstituted $C_{1-6}$ alkyl (e.g., substituted or unsubstituted Me or substituted or unsubstituted Et)). In certain embodiments, $R^5$ is optionally substituted $C_{1-6}$ alkyl. In certain embodiments, $R^5$ is halogen. In certain embodiments, $R^5$ is F. In certain embodiments, $R^5$ is Br. In certain embodiments, $R^5$ is Cl. In certain embodiments, $R^5$ is I. In certain embodiments, $R^5$ is-NO$_2$. In certain embodiments, $R^5$ is —OR$^{a1}$ (e.g., —OH, —O (substituted or unsubstituted $C_{1-6}$ alkyl) (e.g., —OMe, —OEt, —OPr, —OBu, or —OBn). In certain embodiments, $R^5$ is —N($R^{22}$)$_2$ (e.g., —NH$_2$, —NH (substituted or unsubstituted $C_{1-6}$ alkyl) (e.g., —NHMe), or —N(substituted or unsubstituted $C_{1-6}$ alkyl)-(substituted or unsubstituted $C_{1-6}$ alkyl) (e.g., —NMe$_2$)). In certain embodiments, $R^{a1}$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group when attached to an oxygen atom; and each occurrence of $R^{a2}$ is independently hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group.

In certain embodiments, Formulae (II) and (III) include one or more instances of substituent $R^X$. In certain embodiments, x2 is 0. In certain embodiments, x2 is 1. In certain embodiments, x2 is 2. In certain embodiments, x2 is 3. In certain embodiments, x2 is 4. In certain embodiments, at least one instance of $R^X$ is hydrogen. In certain embodiments, at least one instance of $R^X$ is optionally substituted alkyl (e.g., substituted or unsubstituted $C_{1-6}$ alkyl (e.g., substituted or unsubstituted Me or substituted or unsubstituted Et)). In certain embodiments, at least one instance of $R^X$ is optionally substituted $C_{1-6}$ alkyl. In certain embodiments, at least one instance of $R^X$ is halogen. In certain embodiments, at least one instance of $R^X$ is F. In certain embodiments, at least one instance of $R^X$ is Br. In certain embodiments, at least one instance of $R^X$ is Cl. In certain embodiments, at least one instance of $R^X$ is I.

Formula (II) includes substituent $R^6$. In certain embodiments, $R^6$ is hydrogen. In certain embodiments, $R^6$ is substituted or unsubstituted acyl (e.g., —C(═O) Me). In certain embodiments, $R^6$ is optionally substituted alkyl (e.g., substituted or unsubstituted $C_{1-6}$ alkyl (e.g., substituted or unsubstituted Me or substituted or unsubstituted Et)). In certain embodiments, $R^6$ is optionally substituted alkenyl (e.g., substituted or unsubstituted $C_{2-6}$ alkenyl). In certain embodiments, $R^6$ is substituted or unsubstituted alkynyl (e.g., substituted or unsubstituted $C_{2-6}$ alkynyl). In certain embodiments, $R^6$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, $R^6$ is substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, $R^6$ is substituted or unsubstituted aryl (e.g., substituted or unsubstituted, 6- to 10-membered aryl). In certain embodiments, $R^6$ is —N($R^{6A}$)$_2$, wherein each instance of $R^{6A}$ is independently hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group. In certain embodiments, $R^6$ is —NH (optionally substituted $C_{1-6}$ alkyl). In certain embodiments, $R^6$ is —NH(Me). In certain embodiments, $R^6$ is —NH(optionally substituted alkyl). In certain embodiments, $R^6$ is —N($R^{6A}$)$_2$, and one instance of $R^{6A}$ is hydrogen and the other instance of $R^{6A}$ is optionally substituted $C_{1-6}$ alkyl.

Formula (II) includes substituent $R^7$. In certain embodiments, $R^7$ is hydrogen. In certain embodiments, $R^7$ is optionally substituted alkyl (e.g., substituted or unsubstituted $C_{1-6}$ alkyl (e.g., substituted or unsubstituted Me or substituted or unsubstituted Et)). In certain embodiments, $R^7$ is optionally substituted $C_{1-6}$ alkyl. In certain embodiments, $R^7$ is halogen. In certain embodiments, $R^7$ is F. In certain embodiments, $R^7$ is Br. In certain embodiments, $R^7$ is Cl. In certain embodiments, $R^7$ is I. In certain embodiments, $R^7$ is —NO$_2$. In certain embodiments, $R^7$ is —OR$^{a1}$ (e.g., —OH, —O(substituted or unsubstituted $C_{1-6}$ alkyl) (e.g., —OMe, —OEt, —OPr, —OBu, or —OBn). In certain embodiments, $R^7$ is —N($R^{a2}$)$_2$ (e.g., —NH$_2$, —NH(substituted or unsubstituted $C_{1-6}$ alkyl) (e.g., —NHMe), or —N(substituted or unsubstituted $C_{1-6}$ alkyl)-(substituted or unsubstituted $C_{1-6}$ alkyl) (e.g., —NMe$_2$)).

Formulae (II) and (III) include one or more instances of substituent $R^7$. In certain embodiments, z is 0. In certain embodiments, z is 1. In certain embodiments, z is 2. In certain embodiments, z is 3. In certain embodiments, z1 is 0. In certain embodiments, z1 is 1. In certain embodiments, z1 is 2. In certain embodiments, x1 is 3. In certain embodiments, z1 is 4. In certain embodiments, z1 is 5. In certain embodiments, at least one instance of $R^Z$ is hydrogen. In certain embodiments, at least one instance of $R^Z$ is optionally substituted alkyl (e.g., substituted or unsubstituted $C_{1-6}$ alkyl (e.g., substituted or unsubstituted Me or substituted or unsubstituted Et)). In certain embodiments, at least one instance of $R^Z$ is optionally substituted $C_{1-6}$ alkyl. In certain embodiments, at least one instance of $R^Z$ is methyl. In certain embodiments, at least one instance of $R^Z$ is halogen. In certain embodiments, at least one instance of $R^Z$ is F. In certain embodiments, at least one instance of $R^Z$ is Br. In certain embodiments, at least one instance of $R^Z$ is Cl. In certain embodiments, at least one instance of $R^Z$ is I. In certain embodiments, in Formula (III), at least one instance of $R^Z$ is optionally substituted acyl (e.g., —C(=O)Me). In certain embodiments, in Formula (III), at least one instance of $R^Z$ is —$OR^{a1}$ (e.g., —OH, —O(substituted or unsubstituted $C_{1-6}$ alkyl) (e.g., —OMe, —OEt, —OPr, —OBu, or —OBn). In certain embodiments, in Formula (III), at least one instance of $R^Z$ is —$N(R^{a2})_2$ (e.g., —$NH_2$, —NH(substituted or unsubstituted $C_{1-6}$ alkyl) (e.g., —NHMe), or —N(substituted or unsubstituted $C_{1-6}$ alkyl)-(substituted or unsubstituted $C_{1-6}$ alkyl) (e.g., —$NMe_2$)). In certain embodiments, at least one instance of $R^Z$ is halogen or optionally substituted alkyl. In certain embodiments, at least one instance of $R^Z$ is halogen or optionally substituted $C_{1-6}$ alkyl).

In certain embodiments, the thiophene comprises a compound of Formula (II), and a pharmaceutically acceptable salt thereof.

In certain embodiments, a compound of Formula (II) is of the formula:

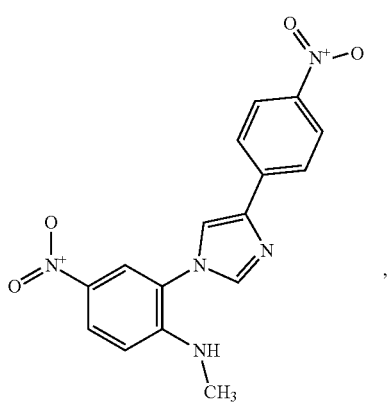

(TM-A)

or a pharmaceutically acceptable salt, solvate, hydrate, polymorph, co-crystal, tautomer, stereoisomer, isotopically labeled derivative, or prodrug thereof.

In one aspect, the TLR2 agonist comprises a compound of Formula (III):

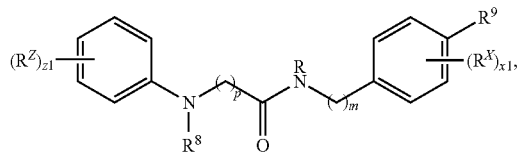

(III)

and pharmaceutically acceptable salts, solvates, hydrates, polymorphs, co-crystals, tautomers, stereoisomers, isotopically labeled derivatives, and prodrugs thereof, wherein:
each instance of $R^Z$ is independently hydrogen, halogen, optionally substituted acyl, optionally substituted alkyl, —$OR^{a1}$, or —$N(R^{a2})_2$, wherein $R^{a1}$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group when attached to an oxygen atom;
wherein each occurrence of $R^{a2}$ is independently hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group; and
m is 0 or 1;
p is 0 or 1;
z1 is 0, 1, 2, 3, 4, or 5;
each instance of $R^X$ is independently hydrogen, halogen, or optionally substituted alkyl;
x1 is 0, 1, 2, 3, or 4;
R is hydrogen or optionally substituted alkyl;
$R^8$ is hydrogen, optionally substituted alkyl, or —$SO_2$($R^{8A}$);
$R^{8A}$ is hydrogen, optionally substituted alkyl, optionally substituted carbocyclyl, optionally substituted heterocyclyl, or optionally substituted aryl; and
$R^9$ is hydrogen, halogen, optionally substituted alkyl, —$OR^{a1}$, —$N(R^{a2})_2$, or —$SO_2N(R^{a2})_2$.

In certain embodiments, m is 0. In certain embodiments, m is 1. In certain embodiments, p is 0. In certain embodiments, p is 1. In certain embodiments, m is 0 and p is 0. In certain embodiments, m is 1 and p is 1.

Formula (III) includes substituent $R^8$. In certain embodiments, $R^8$ is hydrogen. In certain embodiments, $R^8$ is optionally substituted alkyl (e.g., substituted or unsubstituted $C_{1-6}$ alkyl (e.g., substituted or unsubstituted Me or substituted or unsubstituted Et)). In certain embodiments, $R^8$ is —$SO_2$ ($R^{8A}$), and $R^{8A}$ is hydrogen, optionally substituted alkyl, optionally substituted carbocyclyl, optionally substituted heterocyclyl, or optionally substituted aryl. In certain embodiments, $R^8$ is —$SO_2$ ($R^{8A}$), and $R^{8A}$ is optionally substituted alkyl. In certain embodiments, $R^8$ is —$SO_2$ ($R^{8A}$), and $R^{8A}$ is optionally substituted $C_{1-6}$ alkyl or optionally substituted phenyl. In certain embodiments, $R^8$ is —$SO_2$ (Me). In certain embodiments, $R^8$ is -$SO_2$ ($R^{8A}$), and $R^{8A}$ is optionally substituted phenyl. In certain embodiments, $R^8$ is

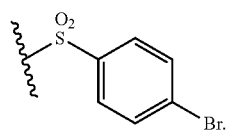 [SMILES: *S(=O)(=O)c1ccc(Br)cc1]

In certain embodiments, $R^8$ is

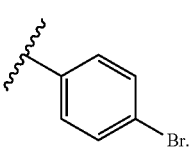 [SMILES: *c1ccc(Br)cc1]

Formula (III) includes substituent $R^9$. In certain embodiments, $R^9$ is hydrogen. In certain embodiments, $R^9$ is optionally substituted alkyl (e.g., substituted or unsubstituted $C_{1-6}$ alkyl (e.g., substituted or unsubstituted Me or substituted or unsubstituted Et)). In certain embodiments, $R^9$ is halogen. In certain embodiments, $R^9$ is F. In certain embodiments, $R^9$ is Br. In certain embodiments, $R^9$ is Cl. In certain embodiments, $R^9$ is I. In certain embodiments, $R^9$ is —$OR^{a1}$ (e.g., —OH, —O (substituted or unsubstituted $C_{1-6}$ alkyl) (e.g., —OMe, —OEt, —OPr, —OBu, or —OBn). In certain embodiments, $R^9$ is —O (substituted or unsubstituted $C_{1-6}$ alkyl). In certain embodiments, $R^9$ is —O(substituted or unsubstituted methyl). In certain embodiments, $R^9$ is -OMe. In certain embodiments, $R^9$ is —$N(R^{a2})_2$ (e.g., —$NH_2$, —NH (substituted or unsubstituted $C_{1-6}$ alkyl) (e.g., —NHMe), or —N(substituted or unsubstituted $C_{1-6}$ alkyl)-(substituted or unsubstituted $C_{1-6}$ alkyl) (e.g., —$NMe_2$)). In certain embodiments, $R^9$ is —$SO_2N(R^{a2})_2$. In certain embodiments, $R^9$ is —$SO_2NH(R^{a2})$. In certain embodiments, $R^9$ is —$SO_2N$ (substituted or unsubstituted $C_{1-6}$ alkyl)$_2$. In certain embodiments, $R^9$ is —$SO_2N$ $(Me)_2$. In certain embodiments, $R^9$ is halogen or —O (optionally substituted $C_{1-6}$ alkyl). In certain embodiments, $R^9$ is —OMe.

In certain embodiments, the thiophene comprises a compound of Formula (III), and a pharmaceutically acceptable salt thereof.

In certain embodiments, a compound of Formula (III) is of the formula

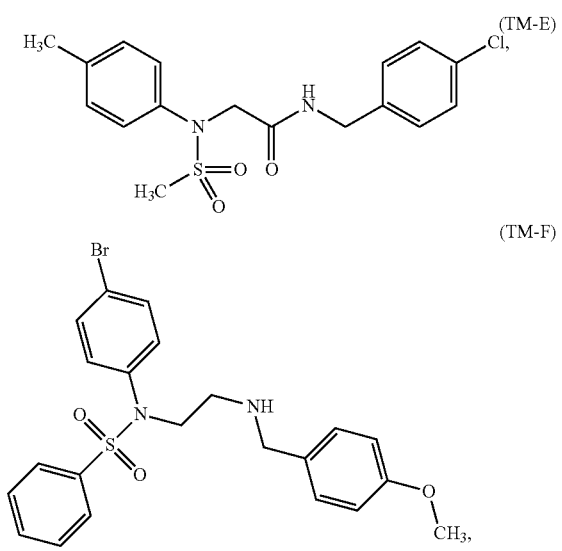

or a pharmaceutically acceptable salt, solvate, hydrate, polymorph, co-crystal, tautomer, stereoisomer, isotopically labeled derivative, or prodrug thereof.

Antigens

The composition described herein comprises an antigen and a TLR2 agonist (e.g., a thiophene compound). An "antigen" refers to an entity that is bound by an antibody or receptor, or an entity that induces the production of the antibody. In some embodiments, an antigen increases the production of antibodies that specifically bind the antigen. In some embodiments, an antigen comprises a protein or polypeptide. Such a protein or peptide is referred to herein as an "immunogenic polypeptide." In some embodiments, the term "antigen" encompasses nucleic acids (e.g., DNA or RNA molecules) that encode immunogenic polypeptides. In some embodiments, the antigen is from a microbial pathogen. For example, the antigen may comprise parts (coats, capsules, cell walls, flagella, fimbriae, and toxins) of bacteria, viruses, fungi, and other microorganisms. In some embodiments, the antigen is a cancer-specific antigen.

In some embodiments, a protein or polypeptide antigen is a wild type protein or polypeptide. In some embodiments, a protein or polypeptide antigen is a polypeptide variant to a wild type protein or polypeptide. The term "polypeptide variant" refers to molecules which differ in their amino acid sequence from a native or reference sequence. The amino acid sequence variants may possess substitutions, deletions, and/or insertions at certain positions within the amino acid sequence, as compared to a native or reference sequence. In some embodiments, polypeptide variants possess at least 50% identity to a native or reference sequence. In some embodiments, variants share at least 70%, at least 80%, at least 90%, at least 95%, or at least 99% identity with a native or reference sequence.

In some embodiments, a polypeptide variant comprises substitutions, insertions, deletions. In some embodiments, a polypeptide variant encompasses covalent variants and derivatives. The term "derivative" is used synonymously with the term "variant" but generally refers to a molecule that has been modified and/or changed in any way relative to a reference molecule or starting molecule.

In some embodiments, sequence tags or amino acids, such as one or more lysines, can be added to peptide sequences (e.g., at the N-terminal or C-terminal ends). Sequence tags can be used for peptide detection, purification or localization. Lysines can be used to increase peptide solubility or to allow for biotinylation. Alternatively, amino acid residues located at the carboxy and amino terminal regions of the amino acid sequence of a peptide or protein may optionally be deleted providing for truncated sequences. Certain amino acids (e.g., C-terminal or N-terminal residues) may alternatively be deleted depending on the use of the sequence, as for example, expression of the sequence as part of a larger sequence which is soluble, or linked to a solid support.

In some embodiments, the polypeptide variants comprises at least one amino acid residue in a native or starting sequence removed and a different amino acid inserted in its place at the same position. Substitutions may be single, where only one amino acid in the molecule has been substituted, or they may be multiple, where two or more amino acids have been substituted in the same molecule. In some embodiments, the antigen is a polypeptide that includes 2, 3, 4, 5, 6, 7, 8, 9, 10, or more substitutions compared to a reference protein.

In some embodiments, the substitution is a conservative amino acids substitution. The term "conservative amino acid substitution" refers to the substitution of an amino acid that is normally present in the sequence with a different amino acid of similar size, charge, or polarity. Examples of conservative substitutions include the substitution of a non-polar (hydrophobic) residue such as isoleucine, valine and leucine for another non-polar residue. Likewise, examples of conservative substitutions include the substitution of one polar (hydrophilic) residue for another such as between arginine and lysine, between glutamine and asparagine, and between glycine and serine. Additionally, the substitution of a basic residue such as lysine, arginine or histidine for another, or the substitution of one acidic residue such as aspartic acid or glutamic acid for another acidic residue are additional examples of conservative substitutions. Examples of non-conservative substitutions include the substitution of a non-polar (hydrophobic) amino acid residue such as isoleucine, valine, leucine, alanine, methionine for a polar (hydrophilic) residue such as cysteine, glutamine, glutamic acid or lysine and/or a polar residue for a non-polar residue.

In some embodiments, protein fragments, functional protein domains, and homologous proteins are used as antigens in accordance with the present disclosure. For example, an antigen may comprise any protein fragment (meaning a polypeptide sequence at least one amino acid residue shorter than a reference polypeptide sequence but otherwise identical) of a reference protein 10, 20, 30, 40, 50, 60, 70, 80, 90, 100 or greater than 100 amino acids in length. In another example, any protein that includes a stretch of 20, 30, 40, 50, or 100 amino acids which are 40%, 50%, 60%, 70%, 80%, 90%, 95%, or 100% identical to a reference protein (e.g., a protein from a microbial pathogen) herein can be utilized in accordance with the disclosure.

In some embodiments, the antigen comprises more than one (e.g., 2, 3, 4, 5, 6, 7, 8, 9, 10, or more) immunogenic proteins or polypeptides. In some embodiments, the more than one immunogenic proteins or polypeptides are derived from one protein (e.g., different fragments or one protein). In some embodiments, the more than one (e.g., from 2, 3, 4, 5, 6, 7, 8, 9, 10, or more proteins) immunogenic proteins or polypeptides are derived from multiple proteins.

In some embodiments, the antigen comprises a nucleic acid encoding an immunogenic protein or polypeptide. In some embodiments, the antigen comprises an immunogenic protein or polypeptide and a nucleic acid encoding the immunogenic protein or polypeptide. The term "nucleic acid" or "polynucleotide," in its broadest sense, includes any compound and/or substance that comprises a polymer of nucleotides. Nucleic acids encoding immunogenic proteins or polypeptides typically comprise an open reading frame (ORF), and one or more regulatory sequences. Nucleic acids (also referred to as polynucleotides) may be or may include, for example, ribonucleic acids (RNAs), deoxyribonucleic acids (DNAs), threose nucleic acids (TNAs), glycol nucleic acids (GNAs), peptide nucleic acids (PNAs), locked nucleic acids (LNAs, including LNA having a β-D-ribo configuration, α-LNA having an a-L-ribo configuration (a diastereomer of LNA), 2'-amino-LNA having a 2'-amino functionalization, and 2'-amino-α-LNA having a 2'-amino functionalization), ethylene nucleic acids (ENA), cyclohexenyl nucleic acids (CeNA) or chimeras or combinations thereof.

In some embodiments, the nucleic acid encoding the immunogenic polypeptide is a DNA (e.g., an expression vector for an immunogenic protein or polypeptide). In some embodiments, the nucleic acid encoding the immunogenic polypeptide is a RNA (e.g., a messenger RNA). A "messenger RNA" (mRNA) refers to any polynucleotide that encodes a (at least one) polypeptide (a naturally-occurring, non-naturally-occurring, or modified polymer of amino acids) and can be translated to produce the encoded polypeptide in vitro, in vivo, in situ, or ex vivo. The basic components of an mRNA molecule typically include at least one coding region, a 5' untranslated region (UTR), a 3' UTR, a 5' cap and a poly-A tail.

In some embodiments, the coding region of the nucleic acid (e.g., DNA or RNA) encoding an immunogenic polypeptide is codon optimized. Codon optimization methods are known in the art and may be used as provided herein. Codon optimization, in some embodiments, may be used to match codon frequencies in target and host organisms to ensure proper folding; bias GC content to increase mRNA stability or reduce secondary structures; minimize tandem repeat codons or base runs that may impair gene construction or expression; customize transcriptional and translational control regions; insert or remove protein trafficking sequences; remove/add post translation modification sites in encoded protein (e.g. glycosylation sites); add, remove or shuffle protein domains; insert or delete restriction sites; modify ribosome binding sites and mRNA degradation sites; adjust translational rates to allow the various domains of the protein to fold properly; or to reduce or eliminate problem secondary structures within the polynucleotide. Codon optimization tools, algorithms and services are known in the art—non-limiting examples include services from GeneArt (Life Technologies), DNA2.0 (Menlo Park CA) and/or proprietary methods. In some embodiments, the open reading frame (ORF) sequence is optimized using optimization algorithms.

In some embodiments, a codon optimized sequence shares less than 95% sequence identity to a naturally-occurring or wild-type sequence (e.g., a naturally-occurring or wild-type mRNA sequence encoding an immunogenic protein or polypeptide). In some embodiments, a codon optimized sequence shares less than 90% sequence identity to a naturally-occurring or wild-type sequence (e.g., a naturally-occurring or wild-type mRNA sequence encoding an immunogenic protein or polypeptide). In some embodiments, a codon optimized sequence shares less than 85% sequence identity to a naturally-occurring or wild-type sequence (e.g., a naturally-occurring or wild-type mRNA sequence encoding an immunogenic protein or polypeptide). In some embodiments, a codon optimized sequence shares less than 80% sequence identity to a naturally-occurring or wild-type sequence (e.g., a naturally-occurring or wild-type mRNA sequence encoding an immunogenic protein or polypeptide). In some embodiments, a codon optimized sequence shares less than 75% sequence identity to a naturally-occurring or wild-type sequence (e.g., a naturally-occurring or wild-type mRNA sequence encoding an immunogenic protein or polypeptide).

In some embodiments, the nucleic acid encoding an immunogenic protein or polypeptide comprises one or more chemical modifications. The terms "chemical modification" and "chemically modified" refer to modification with respect to adenosine (A), guanosine (G), uridine (U), thymidine (T) or cytidine (C) ribonucleosides or deoxyribonucleosides in at least one of their position, pattern, percent or population.

In some embodiments, the nucleic acid (e.g., DNA or RNA) encoding an immunogenic polypeptide comprises various (more than one) different modifications. In some embodiments, a particular region of a nucleic acid (e.g., DNA or RNA) contains one, two or more (optionally different) nucleoside or nucleotide modifications. In some embodiments, a modified nucleic acid (e.g., DNA or RNA), introduced to a cell or organism, exhibits reduced degradation in the cell or organism, respectively, relative to an unmodified nucleic acid. In some embodiments, a modified nucleic acid (e.g., DNA or RNA), introduced into a cell or organism, may exhibit reduced immunogenicity in the cell or organism, respectively (e.g., a reduced innate response).

Modified nucleic acid (e.g., DNA or RNA) may comprise modifications that are naturally-occurring, non-naturally-occurring or the polynucleotide may comprise a combination of naturally-occurring and non-naturally-occurring modifications. The nucleic acid encoding an immunogenic polypeptide described herein may include any useful modification, for example, of a sugar, a nucleobase, or an internucleoside linkage (e.g., to a linking phosphate, to a phosphodiester linkage or to the phosphodiester backbone).

Modified nucleic acid (e.g., DNA or RNA), in some embodiments, comprise non-natural modified nucleotides that are introduced during synthesis or post-synthesis of the polynucleotides to achieve desired functions or properties. The modifications may be present on an internucleotide linkages, purine or pyrimidine bases, or sugars. The modification may be introduced with chemical synthesis or with a polymerase enzyme at the terminal of a chain or anywhere else in the chain. Any of the regions of a nucleic acid may be chemically modified.

In some embodiments, a chemically modified nucleic acid comprises one or more modified nucleosides. A "nucleoside" refers to a compound containing a sugar molecule (e.g., a pentose or ribose) or a derivative thereof in combination with an organic base (e.g., a purine or pyrimidine) or a derivative thereof (also referred to herein as "nucleobase"). A nucleotide" refers to a nucleoside, including a phosphate group. Modified nucleotides may by synthesized by any useful method, such as, for example, chemically, enzymatically, or recombinantly, to include one or more modified or non-natural nucleosides. Polynucleotides may comprise a region or regions of linked nucleosides. Such regions may have variable backbone linkages. The linkages may be standard phosphodiester linkages, in which case the polynucleotides would comprise regions of nucleotides.

In some embodiments, a modified nucleobase is a modified uridine. Exemplary nucleobases and nucleosides having a modified cytosine include N4-acetyl-cytidine (ac4C), 5-methyl-cytidine (m5C), 5-halo-cytidine (e.g., 5-iodo-cytidine), 5-hydroxymethyl-cytidine (hm5C), 1-methyl-pseudoisocytidine, 2-thio-cytidine (s2C), and 2-thio-5-methyl-cytidine.

In some embodiments, a modified nucleobase is a modified uridine. Exemplary nucleobases and In some embodiments, a modified nucleobase is a modified cytosine. nucleosides having a modified uridine include 5-cyano uridine, and 4'-thio uridine.

In some embodiments, a modified nucleobase is a modified adenine. Exemplary nucleobases and nucleosides having a modified adenine include 7-deaza-adenine, 1-methyl-adenosine (m1A), 2-methyl-adenine (m2A), and N6-methyl-adenosine (m6A).

In some embodiments, a modified nucleobase is a modified guanine. Exemplary nucleobases and nucleosides having a modified guanine include inosine (I), 1-methyl-inosine (m1I), wyosine (imG), methylwyosine (mimG), 7-deaza-guanosine, 7-cyano-7-deaza-guanosine (preQ0), 7-aminomethyl-7-deaza-guanosine (preQ1), 7-methyl-guanosine (m7G), 1-methyl-guanosine (m1G), 8-oxo-guanosine, 7-methyl-8-oxo-guanosine.

In some embodiments, the antigen of the present disclosure is from a microbial pathogen, e.g., from a bacterium, mycobacterium, fungus, a virus, parasite, or prion. For example, the antigen may comprise a protein or polypeptide, or a nucleic acid encoding the protein or polypeptide from the microbial pathogen. In some embodiments, the antigen may comprise a microbial pathogen (e.g., a bacterial cell, a viral particle, or a fungus cell). In some embodiments, the microbial pathogen cell is live or killed. In some embodiments, the microbial pathogen is attenuated its pathogenicity. An attenuated microbial pathogen may elicit immune response but does not cause the disease that a wild-type microbial pathogen would cause.

Exemplary, non-limiting bacterial taxa, species, and strains, suitable for use in some embodiments of this disclosure include: *Escherichia* spp., *Enterobacter* spp. (e.g., *Enterobacter cloacae*), *Salmonella* spp. (e.g., *Salmonella enteritidis, Salmonella typhi*), *Shigella* spp., *Pseudomonas* spp. (e.g., *Pseudomonas aeruginosa, Pseudomonas pachastrellae, Pseudomonas stutzeri*), *Moraxella* spp. (e.g., *Moraxella catarrhalis*), *Neisseria* spp. (e.g., *Neisseria gonorrhoeae, Neisseria meningitidis*), *Helicobacter* spp., (e.g., *Helicobacter pylori*) *Stenotrophomonas* spp., *Vibrio* spp. (e.g., *Vibrio cholerae*), *Legionella* spp. (*Legionella pneumophila*), *Hemophilus* spp. (e.g., *Hemophilus influenzae*), *Klebsiella* spp. (e.g., *Klebsiella pneumoniae*), *Proteus* spp. (e.g., *Proteus mirabilis*), *Serratia* spp. (*Serratia marcescens*), *Streptococcus* spp., *Staphylococcus* spp., *Corynebacterium* spp., *Listeria* spp., and *Clostridium* spp., *Bacillus* spp. (e.g., *Bacillus anthracis*) *Bordetella* spp. (e.g., *Bordetella pertussis*); *Borrelia* spp. (e.g., *Borrelia burgdorferi*); *Brucella* spp. (e.g., *Brucella abortus, Brucella canis, Brucella melitensis, Brucella suis*); *Campylobacter* spp. (e.g., *Campylobacter jejuni*); *Chlamydia* spp. and *Chlamydophila* spp. (e.g., *Chlamydia pneumoniae, Chlamydia trachomatis, Chlamydophila psittaci*); *Clostridium* spp. (e.g., *Clostridium botulinum, Clostridium difficile, Clostridium perfringens, Clostridium tetani*); *Corynebacterium* spp. (e.g., *Corynebacterium diphtheriae*); *Enterococcus* spp. (e.g., *Enterococcus faecalis, Enterococcus faecium*); *Escherichia* spp. (e.g., *Escherichia coli*, Enterotoxic *E. coli*, enteropathogenic *E. coli; E. coli* O157:H7); *Francisella* spp. (e.g., *Francisella tularensis*); *Haemophilus* spp. (e.g., *Haemophilus influenzae*); *Helicobacter* spp. (e.g., *Helicobacter pylori*); *Legionella* spp. (e.g., *Legionella pneumophila*); *Leptospira* spp. (e.g., *Leptospira interrogans*); *Listeria* spp. (e.g., *Listeria monocytogenes*); *Mycobacterium* spp. (e.g., *Mycobacterium leprae, Mycobacterium tuberculosis, Mycobacterium ulcerans*); *Mycoplasma* spp. (e.g., *Mycoplasma pneumoniae*); *Neisseria* spp. (e.g., *Neisseria gonorrhoeae, Neisseria meningitidis*); *Pseudomonas* spp. (e.g., *Pseudomonas aeruginosa*); *Rickettsia* spp. (e.g., *Rickettsia rickettsii*); *Salmonella* spp. (e.g., *Salmonella typhi, Salmonella typhimurium*); *Shigella* spp. (e.g., *Shigella sonnei*); *Staphylococcus* spp. (e.g., *Staphylococcus aureus, Staphylococcus epidermidis, Staphylococcus saprophyticus*); *Streptococcus* spp. (e.g., *Streptococcus agalactiae, Streptococcus pneumoniae, Streptococcus pyogenes*); *Treponema* spp. (e.g., *Treponema pallidum*); *Pseudodiomarina* spp. (e.g., *P. maritima*); *Marinobacter* spp. (e.g., *Marinobacter hydrocarbonoclasticus, Marinobacter vinifirmus*) *Alcanivorax* spp. (e.g., *alcanivorax dieselolei*); *Acetinobacter* spp. (e.g., *A. venetianus*); *Halomonas* spp. (e.g., *H. shengliensis*); *Labrenzia* spp.; *Microbulifer* spp. (e.g., *M. schleiferi*); *Shewanella* spp. (e.g., *S. algae*); *Vibrio* spp. (e.g., *Vibrio cholerae, Vibrio alginolyticus, Vibrio hepatarius*); and *Yersinia* spp. (e.g., *Yersinia pestis*).

In some embodiments, the bacterium is *Bacillus anthracis* (causing anthrax), *Bordetella pertussis* (causing whooping cough), *Corynebacterium diphtheriae* (causing diphtheria), *Clostridium tetani* (causing tetanus), *Haemophilus influenzae* type b, pneumococcus (causing pneumococcal infections), Staphylococci spp. (including Group A or B streptococci), *Mycobacterium tuberculosis, Neiserria meningitidis* (causing meningococcal disease), *Salmonella typhi* (causing typhoid), *Vibrio cholerae* (causing Cholera), or *Yersinia pestis* (causing plague).

In some embodiments, the antigen is derived from a Gram-negative bacterium. In some embodiments, the antigen comprises a lipopolysaccharide endotoxin (LPS) from a Gram-negative bacterium. A "lipopolysaccharide endotoxin (LPS)" refers to a large molecule consisting of a lipid and a polysaccharide composed of O-antigen, outer core and inner core joined by a covalent bond. LPS is found in the outer membrane of Gram-negative bacteria. Non-limiting examples of gram-negative bacterial species include: *Neisseria* species including *Neisseria gonorrhoeae* and *Neisseria meningitidis*, *Branhamella* species including *Branhamella catarrhalis*, *Escherichia* species including *Escherichia coli*, *Enterobacter species*, *Proteus* species including *Proteus mirabilis*, *Pseudomonas* species including *Pseudomonas aeruginosa*, *Pseudomonas mallei*, and *Pseudomonas pseudomallei*, *Klebsiella* species including *Klebsiella pneumoniae*, *Salmonella species*, *Shigella species*, *Serratia species*, *Acinetobacter* species; *Haemophilus* species including *Haemophilus influenzae* and *Haemophilus ducreyi*; *Brucella* species, *Yersinia* species including *Yersinia pestis* and *Yersinia enterocolitica*, *Francisella* species including *Francisella tularensis*, *Pasteurella* species including *Pasteurella multocida*, *Vibrio cholerae*, *Flavobacterium species*, *meningosepticum*, *Campylobacter* species including *Campylobacter jejuni*, *Bacteroides* species (oral, pharyngeal) including *Bacteroides fragilis*, *Fusobacterium* species including *Fusobacterium nucleatum*, *Calymmatobacterium granulomatis*, *Streptobacillus* species including *Streptobacillus moniliformis*, *Legionella* species including *Legionella pneumophila*.

In some embodiments, the antigen is derived from a Gram-positive bacterium. Exemplary Gram-positive bacteria include, but are not limited to, *Staphylococcus* spp., *Streptococcus* spp., *Micrococcus* spp., *Peptococcus* spp., *Peptostreptococcus* spp., *Enterococcus* spp., *Bacillus* spp., *Clostridium* spp., *Lactobacillus* spp., *Listeria* spp., *Erysipelothrix* spp., *Propionibacterium* spp., *Eubacterium* spp., *Corynebacterium* spp., *Capnocytophaga* spp., *Bifidobacterium* spp., and *Gardnerella* spp. In some embodiments, the Gram-positive bacteria is a bacteria of the phylum Firmicutes. In some embodiments, the Gram-positive bacteria is *Streptococcus*.

Other types of bacteria include acid-fast bacilli, spirochetes, and actinomycetes. Examples of acid-fast bacilli include *Mycobacterium* species including *Mycobacterium tuberculosis* and *Mycobacterium leprae*. Examples of spirochetes include *Treponema* species including *Treponema pallidum*, *Treponema pertenue*, *Borrelia* species including *Borrelia burgdorferi* (Lyme disease), and *Borrelia recurrentis*, and *Leptospira* species. Examples of actinomycetes include: *Actinomyces* species including *Actinomyces israelii*, and *Nocardia* species including *Nocardia asteroides*.

Examples of viruses include but are not limited to: Retroviruses, human immunodeficiency viruses including HIV-1, HDTV-III, LAVE, HTLV-III/LAV, HIV-III, HIV-LP, Cytomegaloviruses (CMV), Picornaviruses, polio viruses, hepatitis A virus, enteroviruses, human Coxsackie viruses, rhinoviruses, echoviruses, Calciviruses, Togaviruses, equine encephalitis viruses, rubella viruses, Flaviruses, dengue viruses, encephalitis viruses, yellow fever viruses, Coronaviruses, Rhabdoviruses, vesicular stomatitis viruses, rabies viruses, Filoviruses, ebola virus, Paramyxoviruses, parainfluenza viruses, mumps virus, measles virus, respiratory syncytial virus (RSV), Orthomyxoviruses, influenza viruses, Bungaviruses, Hantaan viruses, phleboviruses and Nairo viruses, Arena viruses, hemorrhagic fever viruses, reoviruses, orbiviruses, rotaviruses, Birnaviruses, Hepadnaviruses, Hepatitis B virus, parvoviruses, Papovaviridae, papilloma viruses, polyoma viruses, Adenoviruses, Herpesviruses including herpes simplex virus 1 and 2, varicella zoster virus, Poxviruses, variola viruses, vaccinia viruses, Irido viruses, African swine fever virus, delta hepatitis virus, non-A, non-B hepatitis virus, Hepatitis C, Norwalk viruses, astroviruses, and unclassified viruses. In some embodiments, the virus is adenovirus, enterovirus such as poliomyelitis (polio), Ebola virus, herpes viruses such as herpes simplex virus, cytomegalovirus and varicella-zoster (chickenpox and shingles), measles, mumps, rubella, hepatitis-A, -B, or -C, human papilloma virus, Influenza virus, rabies, Japanese encephalitis, rotavirus, human immunodeficiency virus (HIV), respiratory syncytial virus (RSV), smallpox, yellow fever, or Zika Virus.

In some embodiments, the antigen comprises a viral protein and/or a nucleic acid encoding a viral protein (e.g., a viral structural or non-structural protein). In some embodiments, the antigen comprises a nucleic acid encoding the viral genome. In some embodiments, the viral genome is modified to produce a modified virus that is attenuated.

Examples of fungus include, but are not limited to: *Cryptococcus* species including *Crytococcus neoformans*, *Histoplasma* species including *Histoplasma capsulatum*, *Coccidioides* species including *Coccidiodes immitis*, *Paracoccidioides* species including *Paracoccidioides brasiliensis*, *Blastomyces* species including *Blastomyces dermatitidis*, *Chlamydia* species including *Chlamydia trachomatis*, *Candida* species including *Candida albicans*, *Sporothrix* species including *Sporothrix schenckii*, *Aspergillus* species, and fungi of mucormycosis. In some embodiments, the fungus is *Candida* spp., *Aspergillus* spp., *Cryptococcus* spp., *Mucormycete*, *Blastomyces dermatitidis* (causing blastomycosis), or endemic mycosis causing fungus such as *Histoplasma capsulatum* (causing histoplasmosis), or *Sporothrix schenckii* (causing sporotrichosis).

Other infectious organisms include, without limitation: parasites. Parasites include *Plasmodium* species, such as *Plasmodium* species including *Plasmodium falciparum*, *Plasmodium malariae*, *Plasmodium ovale*, and *Plasmodium vivax* and *Toxoplasma gondii*. Blood-borne and/or tissues parasites include *Plasmodium* species, *Babesia* species including *Babesia microti* and *Babesia divergens*, *Leishmania* species including *Leishmania tropica*, *Leishmania species*, *Leishmania braziliensis*, *Leishmania donovani*, *Trypanosoma* species including *Trypanosoma gambiense*, *Trypanosoma* rhodesiense (African sleeping sickness), and *Trypanosoma cruzi* (Chagas' disease). In some embodiments, the parasite is *Plasmodium* spp., *Leishmania*, or a helminth.

Other medically relevant microorganisms have been described extensively in the literature, e.g., see C. G. A Thomas, *Medical Microbiology*, Bailliere Tindall, Great Britain 1983, incorporated herein by reference.

In some embodiments, the antigen of the present disclosure comprises a cancer-specific antigen and/or a nucleic acid encoding such. A "cancer-specific antigen" refers to a protein that is specifically expressed or upregulated in a cancer cell, as compared to non-cancerous cells of the same origin. A cancer-specific antigen, or epitopes derived therefrom, can be recognized by the immune system to induce a immune response against the cancer. Classes of proteins that may be cancer-specific antigen include, without limitation: enzymes, receptors, and transcription factors.

A large number of proteins that specifically express in cancer cells or are upregulated in cancer cells have been identified (Hassane et al., Holland-Frei Cancer Medicine. 6th edition, incorporated herein by reference). The known tumor specific antigens are classified into different classes: cancer-testis antigens (e.g., MAGE family members or NY-ESO-1), differentiation antigens (e.g., tyrosinase and Melan-A/MART-1 for melanoma, and PSA for prostate cancer), overexpressed cancer-specific antigens (e.g., Her-2/neu, Survivin, Telomerase and WT1), cancer-specific antigens arising from mutations of normal genes (e.g., mutated β-catenin or CDK4), cancer-specific antigens arising from abnormal post-translational modifications (e.g., altered glycosylation patterns) that lead to novel epitopes in tumors (e.g., MUC1), and oncoviral proteins (e.g., human papilloma type 16 virus proteins, E6 and E7). In some embodiments, the tumor-specific antigen is expressed in a broad range of different types of cancers. In some embodiments, the tumor-specific antigen is expressed only in one or a few types of cancers.

In some embodiments, the antigen comprises a fragment or an epitope derived from a cancer-specific antigen and/or a nucleic acid encoding such. For example, the fragment or an epitope derived from a cancer-specific antigen may be 5-40 amino acids long. In some embodiments, the fragment or an epitope derived from a cancer-specific antigen is 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 amino acids long.

In some embodiments, the fragment or epitope derived from a cancer-specific antigen is a heteroclitic epitope. A "heteroclitic epitope" refers to an altered version of an endogenous peptide sequence (i.e., an analog) from a cancer-specific antigen engineered to elicit potent immune reactions. Heteroclitic epitopes have increased stimulatory capacity or potency for a specific T cell, as measured by increased responses to a given dose, or by a requirement of lesser amounts to achieve the same response and therefore provide benefit as vaccine components since these epitopes induce T cell responses stronger than those induced by the native epitope.

In some embodiments, the heteroclitic epitope comprises modifications, e.g., amino acid substitutions, as compared to the native sequence in the cancer-specific antigen. In some embodiments, the heteroclitic epitope comprises more than one amino acid substitutions (e.g., 2, 3, 4, 5, or more) compared to the native sequence of the cancer-specific antigen it is derived from. In some embodiments, a heteroclitic epitope is at least 60%, at least 70%, at least 80%, at least 90%, at least 98%, or at least 99% identical to the native sequence that it is derived from. In some embodiments, a heteroclitic epitope is 60%, 65%, 70%, 75%, 80%, 85%, 90%, 95%, 98%, or 99% identical to the native sequence that it is derived from.

In some embodiments, a heteroclitic epitope is more immunogenic than a peptide of its native sequence. For example, a heteroclitic epitope may be at least 30% more immunogenic (i.e., induces a stronger immune response) than its corresponding native peptide. In some embodiments, a heteroclitic epitope may be at least 30%, at least 40%, at least 50%, at least 60%, at least 70%, at least 80%, at least 90%, at least 100%, at least 2-fold, at least 3-fold, at least 4-fold, at least 5-fold, at least 6-fold, at least 7-fold, at least 8-fold, at least 9-fold, at least 10-fold, at least 20-fold, at least 30-fold, at least 40-fold, at least 50-fold, at least 60-fold, at least 70-fold, at least 80-fold, at least 90-fold, at least 100-fold, or more immunogenic than its corresponding native peptide.

In some embodiments, the fragment or epitope derived from a cancer-specific antigen is a cryptic epitope. A "cryptic epitope" refers to an epitope derived from a cancer-specific antigen that does not necessarily undergo antigen processing/presentation and are 'hidden' from immune recognition. Cryptic epitopes usually appear in very low concentration on APC and do not delete auto-reactive T cells. Cryptic epitopes are not presented for recognition by T cells unless they are produced in unusually large concentrations or unless they are freed from the configuration of their native antigen. Cryptic epitopes derived from cancer-specific antigens may be used to break the tolerance of T cells to the tumor and induce potent immune response against the tumor. Such principles have been described in Pardoll, et al., PNAS, Vol. 96, pp. 5340-5342 (1999), the entire contents of which are incorporated herein by reference.

In some embodiments, the cryptic epitope is generated from translation of a non-coding region of the cancer-specific antigen gene or translation of a different reading frame of a coding region of the cancer-specific antigen. A cryptic epitope may be more immunogenic (i.e., induces a stronger immune response) than any native peptide derived from the cancer-specific antigen. For example, a cryptic epitope may be at least 30% more immunogenic than any native peptide derived from the cancer-specific antigen. In some embodiments, a cryptic epitope is at least 30%, at least 40%, at least 50%, at least 60%, at least 70%, at least 80%, at least 90%, at least 100%, at least 2-fold, at least 3-fold, at least 4-fold, at least 5-fold, at least 6-fold, at least 7-fold, at least 8-fold, at least 9-fold, at least 10-fold, at least 20-fold, at least 30-fold, at least 40-fold, at least 50-fold, at least 60-fold, at least 70-fold, at least 80-fold, at least 90-fold, at least 100-fold, or more immunogenic than any native peptide derived from the cancer-specific antigen. One skilled in the art is familiar with how to assess the immune response induced by an antigen, e.g., measuring antibody titers.

In some embodiments, the cancer-specific antigen is a neoantigen. A "neoantigen" refers to an antigen generated via random somatic mutations occurring in cancer cells and are thus specific to the lineage of cancer cells it is derived from. Neoantigens are regarded in the art to be responsible for the immunogenicity of tumors (Srivastava et al., 1993, Duan et al., 2009; van der Bruggen et al., 2013, incorporated herein by reference), and mathematic modeling has predicted the existence of tens to hundreds of neoepitopes (epitopes derived from neoantigens) in individual human tumors (Srivastava 2009, incorporated herein by reference). The recent revolution in high-throughput DNA sequencing and accompanying bioinformatics approaches has finally made it possible to actually identify the individually specific neoepitopes in individual cancers.

In some embodiments, the antigen described herein is an antigen designed to provide broad heterologous protection against a range of pathogens. Heterologous immunity refers to the phenomenon whereby a history of an immune response against a stimulus or pathogen can provide a level of immunity to a second unrelated stimulus or pathogen (e.g., as described in Chen et al., Virology 2015 482:89-97, incorporated herein by reference). For example, an antigen that induces cross-reactive memory CD8+ T cells against multiple unrelated viruses such as influenza A and Epstein-Barr Virus (EBV), as described in Watkin et al., J Allerg Clin Immunol 2017 October; 140 (4) 1206-1210, incorporated herein by reference. In some embodiments, the TLR2 agonists (e.g., thiophene compounds) described herein induce and/or enhance the heterologous protection.

Polypeptide or polynucleotide molecules of the present disclosure may share a certain degree of sequence similarity or identity with reference molecules (e.g., reference polypeptides or reference polynucleotides), for example, wild-type molecules. The term "identity" as known in the art, refers to a relationship between the sequences of two or more polypeptides or polynucleotides, as determined by comparing the sequences. In the art, identity also means the degree of sequence relatedness between them as determined by the number of matches between strings of two or more amino acid residues or nucleic acid residues. Identity measures the percent of identical matches between the smaller of two or more sequences with gap alignments (if any) addressed by a particular mathematical model or computer program (e.g., "algorithms"). Identity of related peptides can be readily calculated by known methods. "% identity" as it applies to polypeptide or polynucleotide sequences is defined as the percentage of residues (amino acid residues or nucleic acid residues) in the candidate amino acid or nucleic acid sequence that are identical with the residues in the amino acid sequence or nucleic acid sequence of a second sequence after aligning the sequences and introducing gaps, if necessary, to achieve the maximum percent identity. Methods and computer programs for the alignment are well known in the art. It is understood that identity depends on a calculation of percent identity but may differ in value due to gaps and penalties introduced in the calculation. Generally, variants of a particular polynucleotide or polypeptide have at least 40%, 45%, 50%, 55%, 60%, 65%, 70%, 75%, 80%, 85%, 90%, 91%, 92%, 93%, 94%, 95%, 96%, 97%, 98%, 99% but less than 100% sequence identity to that particular reference polynucleotide or polypeptide as determined by sequence alignment programs and parameters described herein and known to those skilled in the art. Such tools for alignment include those of the BLAST suite (Stephen F. Altschul, et al (1997), "Gapped BLAST and PSI-BLAST: a new generation of protein database search programs", Nucleic Acids Res. 25:3389-3402). Another popular local alignment technique is based on the Smith-Waterman algorithm (Smith, T. F. & Waterman, M. S. (1981) "Identification of common molecular subsequences." J. Mol. Biol. 147: 195-197.) A general global alignment technique based on dynamic programming is the Needleman-Wunsch algorithm (Needleman, S. B. & Wunsch, C. D. (1970) "A general method applicable to the search for similarities in the amino acid sequences of two proteins." J. Mol. Biol. 48:443-453.). More recently a Fast Optimal Global Sequence Alignment Algorithm (FOGSAA) has been developed that purportedly produces global alignment of nucleotide and protein sequences faster than other optimal global alignment methods, including the Needleman-Wunsch algorithm. Other tools are described herein, specifically in the definition of "identity" below.

As used herein, the term "homology" refers to the overall relatedness between polymeric molecules, e.g. between nucleic acid molecules (e.g. DNA molecules and/or RNA molecules) and/or between polypeptide molecules. Polymeric molecules (e.g. nucleic acid molecules (e.g. DNA molecules and/or RNA molecules) and/or polypeptide molecules) that share a threshold level of similarity or identity determined by alignment of matching residues are termed homologous. Homology is a qualitative term that describes a relationship between molecules and can be based upon the quantitative similarity or identity. Similarity or identity is a quantitative term that defines the degree of sequence match between two compared sequences. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% identical or similar. The term "homologous" necessarily refers to a comparison between at least two sequences (polynucleotide or polypeptide sequences). Two polynucleotide sequences are considered homologous if the polypeptides they encode are at least 50%, 60%, 70%, 80%, 90%, 95%, or even 99% for at least one stretch of at least 20 amino acids. In some embodiments, homologous polynucleotide sequences are characterized by the ability to encode a stretch of at least 4-5 uniquely specified amino acids. For polynucleotide sequences less than 60 nucleotides in length, homology is determined by the ability to encode a stretch of at least 4-5 uniquely specified amino acids. Two protein sequences are considered homologous if the proteins are at least 50%, 60%, 70%, 80%, or 90% identical for at least one stretch of at least 20 amino acids.

Homology implies that the compared sequences diverged in evolution from a common origin. The term "homolog" refers to a first amino acid sequence or nucleic acid sequence (e.g., gene (DNA or RNA) or protein sequence) that is related to a second amino acid sequence or nucleic acid sequence by descent from a common ancestral sequence. The term "homolog" may apply to the relationship between genes and/or proteins separated by the event of speciation or to the relationship between genes and/or proteins separated by the event of genetic duplication. "Orthologs" are genes (or proteins) in different species that evolved from a common ancestral gene (or protein) by speciation. Typically, orthologs retain the same function in the course of evolution. "Paralogs" are genes (or proteins) related by duplication within a genome. Orthologs retain the same function in the course of evolution, whereas paralogs evolve new functions, even if these are related to the original one.

The term "identity" refers to the overall relatedness between polymeric molecules, for example, between polynucleotide molecules (e.g. DNA molecules and/or RNA molecules) and/or between polypeptide molecules. Calculation of the percent identity of two polynucleic acid sequences, for example, can be performed by aligning the two sequences for optimal comparison purposes (e.g., gaps can be introduced in one or both of a first and a second nucleic acid sequences for optimal alignment and non-identical sequences can be disregarded for comparison purposes). In some embodiments, the length of a sequence aligned for comparison purposes is at least 30%, at least 40%, at least 50%, at least 60%, at least 70%, at least 80%, at least 90%, at least 95%, or 100% of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. For example, the percent identity between two nucleic acid sequences can be determined using methods such as those described in Computational Molecular Biology, Lesk, A. M., ed., Oxford University Press, New York, 1988; Biocomputing: Informatics and Genome Projects, Smith, D. W., ed., Academic Press, New York, 1993; Sequence Analysis in Molecular Biology, von Heinje, G., Academic Press, 1987; Computer Analysis of Sequence Data, Part I, Griffin, A. M., and Griffin, H. G., eds., Humana Press, New Jersey, 1994; and Sequence Analysis Primer, Gribskov, M. and Devereux, J., eds., M Stockton Press, New York, 1991; each of which is incorporated herein by reference. For example, the percent identity between two nucleic acid sequences can be determined using the algorithm of Meyers and Miller (CABIOS, 1989, 4:11-17), which has been incorporated into the ALIGN program (version 2.0) using a PAM120 weight residue table, a gap length penalty of 12 and a gap penalty of 4. The percent identity between two nucleic acid sequences can, alternatively, be determined using the GAP program in the GCG software package using an NWSgapdna.CMP matrix. Methods commonly employed to determine percent identity between sequences include, but are not limited to those disclosed in Carillo, H., and Lipman, D., SIAM J Applied Math., 48:1073 (1988); incorporated herein by reference. Techniques for determining identity are codified in publicly available computer programs. Exemplary computer software to determine homology between two sequences include, but are not limited to, GCG program package, Devereux, J., et al., Nucleic Acids Research, 12 (1), 387 (1984)), BLASTP, BLASTN, and FASTA Altschul, S. F. et al., J. Molec. Biol., 215, 403 (1990)).

Compositions and Vaccines

The composition of the present disclosure comprises an antigen and a TLR2 agonist (e.g., a thiophene compound). In some embodiments, the composition comprises an antigen and a TLR2 agonist of Formulae (I), (II), or (III). In some embodiments, the composition comprises an antigen and compound 80, or a compound of Formulae (I), (II), or (III) described herein.

In some embodiments, the TLR2 agonist (e.g., a thiophene compound) is conjugated to the antigen. In some embodiments, the TLR2 agonist (e.g., a thiophene compound) is not conjugated to the antigen. In some embodiments, the TLR2 agonist (e.g., a thiophene compound) is lipidated.

Methods of conjugating a compound to another molecule (e.g., a protein or a nucleic acid) is known to those skilled in the art. For example, in some embodiments, conjugation may be achieved via reactive chemical groups by incorporating one of a pair of reactive chemical groups that react with each other to each of the two molecules to be conjugated. A "reactive chemical group" or "functional chemical group" refers to specific groups (moieties) of atoms or bonds within molecules that are responsible for the characteristic chemical reactions of those molecules. These terms are used interchangeably herein. One example of such reactive group is a "click chemistry handle." Click chemistry is a chemical approach introduced by Sharpless in 2001 and describes chemistry tailored to generate substances quickly and reliably by joining small units together. See, e.g., Kolb, Finn and Sharpless Angewandte Chemie International Edition (2001) 40:2004-2021; Evans, Australian Journal of Chemistry (2007) 60:384-395). Exemplary coupling reactions (some of which may be classified as "Click chemistry") include, but are not limited to, formation of esters, thioesters, amides (e.g., such as peptide coupling) from activated acids or acyl halides; nucleophilic displacement reactions (e.g., such as nucleophilic displacement of a halide or ring opening of strained ring systems); azide-alkyne Huisgon cycloaddition; thiol-yne addition; imine formation; and Michael additions (e.g., maleimide addition). Non-limiting examples of a click chemistry handle include an azide handle, an alkyne handle, or an aziridine handle. Azide is the anion with the formula N3-. It is the conjugate base of hydrazoic acid (HN3). N3- is a linear anion that is isoelectronic with CO2, NCO—, N2O, NO2+ and NCF. Azide can be described by several resonance structures, an important one being —N=N+=N—. An alkyne is an unsaturated hydrocarbon containing at least one carbon-carbon triple bond. The simplest acyclic alkynes with only one triple bond and no other functional groups form a homologous series with the general chemical formula CnH2n-2. Alkynes are traditionally known as acetylenes, although the name acetylene also refers specifically to C2H2, known formally as ethyne using IUPAC nomenclature. Like other hydrocarbons, alkynes are generally hydrophobic but tend to be more reactive. Aziridines are organic compounds containing the aziridine functional group, a three-membered heterocycle with one amine group (—NH—) and two methylene bridges (—CH2-). The parent compound is aziridine (or ethylene imine), with molecular formula C2H5N.

Other non-limiting, exemplary reactive groups include: acetals, ketals, hemiacetals, and hemiketals, carboxylic acids, strong non-oxidizing acids, strong oxidizing acids, weak acids, acrylates and acrylic acids, acyl halides, sulfonyl halides, chloroformates, alcohols and polyols, aldehydes, alkynes with or without acetylenic hydrogen amides and imides, amines, aromatic, amines, phosphines, pyridines, anhydrides, aryl halides, azo, diazo, azido, hydrazine, and azide compounds, strong bases, weak bases, carbamates, carbonate salts, chlorosilanes, conjugated dienes, cyanides, inorganic, diazonium salts, epoxides, esters, sulfate esters, phosphate esters, thiophosphate esters borate esters, ethers, soluble fluoride salts, fluorinated organic compounds, halogenated organic compounds, halogenating agents, aliphatic saturated hydrocarbons, aliphatic unsaturated hydrocarbons, hydrocarbons, aromatic, insufficient information for classification, isocyanates and isothiocyanates, ketones, metal hydrides, metal alkyls, metal aryls, and silanes, alkali metals, nitrate and nitrite compounds, inorganic, nitrides, phosphides, carbides, and silicides, nitriles, nitro, nitroso, nitrate, nitrite compounds, organic, non-redox-active inorganic compounds, organometallics, oximes, peroxides, organic, phenolic salts, phenols and cresols, polymerizable compounds, quaternary ammonium and phosphonium salts, strong reducing agents, weak reducing agents, acidic salts, basic salts, siloxanes, inorganic sulfides, organic sulfides, sulfite and thiosulfate salts, sulfonates, phosphonates, organic thiophosphonates, thiocarbamate esters and salts, and dithiocarbamate esters and salts. In some embodiments, the reactive group is a carboxylic acid group.

The composition comprising an antigen and a TLR2 agonist (e.g., a thiophene compound) described herein are immunogenic. Being "immunogenic" means that the composition elicits immune response when administered to a subject (e.g., a mammalian subject such as a human). As used herein, an "immune response" refers to a response by a cell of the immune system, such as an antigen-presenting cell, dendritic cell, monocyte, macrophage, NKT cell, NK cell, basophil, eosinophil, or neutrophil, B cell, T cell (CD4 or CD8), regulatory T cell, antigen-presenting cell, dendritic cell, monocyte, macrophage, NKT cell, NK cell, basophil, eosinophil, or neutrophil, to a stimulus (e.g., to an antigen or an adjuvant).

In some embodiments, the immune response elicited by the composition described herein is specific for a particular antigen (an "antigen-specific response" or "adaptive immune response"), and refers to a response by a CD4 T cell, CD8 T cell, or B cell via their antigen-specific receptor. In some embodiments, an immune response is a T cell response, such as a CD4+ response or a CD8+ response. Such responses by these cells can include, for example, cytotoxicity, proliferation, cytokine or chemokine production, trafficking, or phagocytosis, and can be dependent on the nature of the immune cell undergoing the response.

In some embodiments, an antigen-specific immune response includes both a humoral and/or a cell-mediated immune response to the antigen. A "humoral immune response" is an antibody-mediated immune response and involves the induction and generation of antibodies that recognize and bind with some affinity for the antigen in the immunogenic composition of the invention, while a "cell-mediated immune response" is one mediated by T-cells and/or other white blood cells. A "cell-mediated immune response" is elicited by the presentation of antigenic epitopes in association with Class I or Class II molecules of the major histocompatibility complex (MHC), CD1 or other non-classical MHC-like molecules. This activates antigen-specific CD4+T helper cells or CD8+ cytotoxic lymphocyte cells ("CTLs"). CTLs have specificity for peptide antigens that are presented in association with proteins encoded by classical or non-classical MHCs and expressed on the surfaces of cells. CTLs help induce and promote the intracellular destruction of intracellular microbes, or the lysis of cells infected with such microbes. Another aspect of cellular immunity involves an antigen-specific response by helper T-cells. Helper T-cells act to help stimulate the function, and focus the activity of, nonspecific effector cells against cells displaying peptide or other antigens in association with classical or non-classical MHC molecules on their surface. A "cell-mediated immune response" also refers to the production of cytokines, chemokines and other such molecules produced by activated T-cells and/or other white blood cells, including those derived from CD4+ and CD8+ T-cells. The ability of a particular antigen or composition to stimulate a cell-mediated immunological response may be determined by a number of assays, such as by lymphoproliferation (lymphocyte activation) assays, CTL cytotoxic cell assays, by assaying for T-lymphocytes specific for the antigen in a sensitized subject, or by measurement of cytokine production by T cells in response to re-stimulation with antigen. Such assays are well known in the art. See, e.g., Erickson et al. (1993) J. Immunol. 151:4189-4199; and Doe et al. (1994) Eur. J. Immunol. 24:2369-2376.

In some embodiments, the immune response elicited by the composition described herein is an innate immune response. An "innate immune response" refers to the response by the innate immune system. The innate immune system uses a set of germline-encoded receptors ("pattern recognition receptor" or "PRR") for the recognition of conserved molecular patterns present in microorganisms. These molecular patterns occur in certain constituents of microorganisms including: lipopolysaccharides, peptidoglycans, lipoteichoic acids, phosphatidyl cholines, bacteria-specific proteins, including lipoproteins, bacterial DNAs, viral single and double-stranded RNAs, unmethylated CpG-DNAs, mannans and a variety of other bacterial and fungal cell wall components. Such molecular patterns can also occur in other molecules such as plant alkaloids. These targets of innate immune recognition are called Pathogen Associated Molecular Patterns (PAMPs) since they are produced by microorganisms and not by the infected host organism. In some embodiments, the innate immune response elicited by the composition described herein confers heterologous ("non-specific") immunity to a broad range of pathogenic microbes by enhancing innate immune responses to subsequent stimuli, a phenomenon known as "trained immunity", a form of innate memory, e.g., as described in Netea et al. (Trained Immunity: An Ancient Way of Remembering. Cell Host Microbe. 2017 Mar. 8; 21 (3): 297-300, incorporated herein by reference).

The receptors of the innate immune system that recognize PAMPs are called Pattern Recognition Receptors (PRRs). (Janeway et al. (1989) Cold Spring Harb. Symp. Quant. Biol. 54:1-13; Medzhitov et al. (1997) Curr. Opin. Immunol. 94:4-9, incorporated herein by reference). PRRs vary in structure and belong to several different protein families. Some of these receptors recognize PAMPs directly (e.g., CD14, DEC205, collectins), while others (e.g., complement receptors) recognize the products generated by PAMP recognition. Members of these receptor families can, generally, be divided into three types: 1) humoral receptors circulating in the plasma; 2) endocytic receptors expressed on immune-cell surfaces, and 3) signaling receptors that can be expressed either on the cell surface or intracellularly. (Medzhitov et al. (1997) Curr. Opin. Immunol. 94:4-9; Fearon et al. (1996) Science 272:50-3, incorporated herein by reference). Non-limiting examples of PRRs include: toll-like receptors (e.g., TLR2), NOD1/2, RIG-1/MDA-5, C-type lectins, and STING.

Cellular PRRs are expressed on effector cells of the innate immune system, including cells that function as professional antigen-presenting cells (APC) in adaptive immunity. Such effector cells include, but are not limited to, macrophages, dendritic cells, B lymphocytes and surface epithelia. This expression profile allows PRRs to directly induce innate effector mechanisms, and also to alert the host organism to the presence of infectious agents by inducing the expression of a set of endogenous signals, such as inflammatory cytokines and chemokines, including, without limitation: chemokines, interferons, interleukins, lymphokines, and tumour necrosis factors. This latter function allows efficient mobilization of effector forces to combat the invaders.

In some embodiments, the composition comprising an antigen and a TLR2 agonist (e.g., a thiophene compound) is a vaccine composition. A "vaccine composition" is a composition that activates or enhances a subject's immune response to an antigen after the vaccine is administered to the subject. In some embodiments, a vaccine stimulates the subject's immune system to recognize the antigen as foreign, and enhances the subject's immune response if the subject is later exposed to the pathogen, whether attenuated, inactivated, killed, or not. Vaccines may be prophylactic, for example, preventing or ameliorating a detrimental effect of a future exposure to a pathogen, or therapeutic, for example, activating the subject's immune response to a pathogen after the subject has been exposed to the pathogen. In some embodiments, a vaccine composition is used to protect or treat an organism against a disease (e.g., an infectious disease or cancer). In some embodiments, the vaccine is a subunit vaccine (e.g., a recombinant subunit vaccine), an attenuated vaccine (e.g., containing an attenuated pathogen such as a bacterial cell or a viral genome), a live vaccine (e.g., containing a live attenuated pathogen such as a bacterium or virus), or a conjugated vaccine (e.g., a vaccine containing an antigen that is not very immunogenic covalently attached to an antigen that is more immunogenic). One non-limiting example of a conjugated vaccine comprises a LPS attached to a strong protein antigen.

The terms "vaccine composition" and "vaccine" are used interchangeably herein. Vaccines that contain cancer-specific antigens are termed herein as "cancer vaccine." Cancer vaccines induce cancer-specific immune response against a cancer or a cancer-specific antigen. Such immunoresponse is effective in inhibiting cancer growth and/or preventing reoccurrence of tumor. Cancer vaccines may be used for cancer immunotherapy, which is a type of cancer treatment designed to boost the body's natural defenses to fight the cancer. It uses substances either made by the body or in a laboratory to improve or restore immune system function.

In some embodiments, the TLR2 agonist (e.g., a thiophene compound) described herein is used as an adjuvant in a vaccine composition (e.g., to enhance an immune response in a subject). It is demonstrated herein that TLR2 agonist (e.g., a thiophene compound) alone induced cytokine (e.g., proinflammatory cytokines such as TNF, IL-12, IL-6, IL1-β) and/or chemokine (e.g., CCL3) production by human peripheral blood mononuclear cells (PBMC) in vitro and enhanced antigen-specific immune response against influenza hemagglutinin antigen in vivo. The TLR2 agonist (e.g., a thiophene compound) described herein also induced expression of NF-κB.

An "adjuvant" refers to a pharmacological or immunological agent that modifies the effect of other agents, for example, of an antigen in a vaccine. Adjuvants are typically included in vaccines to enhance the recipient subject's immune response to an antigen. The use of adjuvants allows the induction of a greater immune response in a subject with the same dose of antigen, or the induction of a similar level of immune response with a lower dose of injected antigen. Adjuvants are thought to function in several ways, including by increasing the surface area of antigen, prolonging the retention of the antigen in the body thus allowing time for the lymphoid system to have access to the antigen, slowing the release of antigen, targeting antigen to macrophages, activating macrophages, activating leukocytes such as antigen-presenting cells (e.g., monocytes, macrophages, and/or dendritic cells), or otherwise eliciting broad activation of the cells of the immune system see, e.g., H. S. Warren et al, Annu. Rev. immunol., 4:369 (1986), incorporated herein by reference. The ability of an adjuvant to induce and increase a specific type of immune response and the identification of that ability is thus a key factor in the selection of particular adjuvants for vaccine use against a particular pathogen. Adjuvants that are known to those of skill in the art, include, without limitation: aluminum salts (referred to herein as "alum"), liposomes, lipopolysaccharide (LPS) or derivatives such as monophosphoryl lipid A (MPLA) and glycopyranosyl lipid A (GLA), molecular cages for antigen, components of bacterial cell walls, endocytosed nucleic acids such as double-stranded RNA (dsRNA), single-stranded DNA (ssDNA), and unmethylated CpG dinucleotide-containing DNA. Typical adjuvants include water and oil emulsions, e.g., Freund's adjuvant and MF59, and chemical compounds such as aluminum hydroxide or alum. At present, currently licensed vaccines in the United states contain only a limited number of adjuvants, such as alum that enhances production of TH 2 cells are and MPLA which activates innte immunity via Toll-like receptor 4 (TLR4). Many of the most effective adjuvants include bacteria or their products, e.g., microorganisms such as the attenuated strain of *Mycobacterium bovis*, Bacille Calmette-Guérin (BCG); microorganism components, e.g., alum-precipitated diphtheria toxoid, bacterial lipopolysaccharides ("endotoxins") and their derivatives such as MPLA and GLA.

In some embodiments, the vaccine composition described herein further comprises a second adjuvant, in addition to the TLR2 agonist (e.g., a thiophene compound) (as the first adjuvant). Any adjuvants known in the art or described herein may be used as the second adjuvant in the composition. In some embodiments, the second adjuvant is an agonist of Pattern Recognition Receptors (PRRs) such as Toll-like receptors (TLRs), NOD-like receptors (NLRs), RIG-I-like receptor (RLR), C-type Lectin receptors (CLRs), and a stimulator of interferon genes (STING). An "agonist" is a chemical that binds to a receptor and activates the receptor to produce a biological response. Agonists of the PPRs enhance immune responses (e.g., innate or adaptive immune response). Agonists of PPRs are known to those skilled in the art. For example, various TLR and NLR agonists are described in Kaczanowska et al, J Leukoc Biol. 2013 June; 93 (6): 847-863; Higgins et al., Curr Infect Dis Rep. 2010 January; 12 (1): 4-12; and Maisonneuve et al., Proc Natl Acad Sci USA. 2014 Aug. 26; 111 (34): 12294-12299, incorporated herein by reference. RIG-I-like receptor agonists are described in Ranjith-Kumar et al., J Biol Chem. 2009 Jan. 9; 284 (2): 1155-1165; and Goulet et al., PLOS Pathogens 9 (8): 10, incorporated herein by reference. CLR agonists are described in Lamb et al., Biochemistry. 2002 Dec. 3; 41 (48): 14340-7; and Yan et al., Front Immunol. 2015; 6:408, incorporated herein by reference. STING agonists are described in Fu et al., Sci Transl Med. 2015 Apr. 15; 7 (283): 283ra52; and Foote et al., Cancer Immunology Research, DOI: 10.1158/2326-6066.CIR-16-0284, incorporated herein by reference. The PPR agonists described herein are also commercially available, e.g., from InvivoGen (California, USA). In some embodiments, the second adjuvant is alum.

In some embodiments, the vaccine composition described herein are formulated for administration to a subject. In some embodiments, the vaccine composition is formulated or administered in combination with one or more pharmaceutically-acceptable excipients. In some embodiments, vaccine compositions comprise at least one additional active substances, such as, for example, a therapeutically-active substance, a prophylactically-active substance, or a combination of both. Vaccine compositions may be sterile, pyrogen-free or both sterile and pyrogen-free. General considerations in the formulation and/or manufacture of pharmaceutical agents, such as vaccine compositions, may be found, for example, in Remington: The Science and Practice of Pharmacy 21st ed., Lippincott Williams & Wilkins, 2005 (incorporated herein by reference in its entirety).

Formulations of the vaccine compositions described herein may be prepared by any method known or hereafter developed in the art of pharmacology. In general, such preparatory methods include the step of bringing the antigen and/or the adjuvant (e.g., TLR2 agonists) into association with an excipient and/or one or more other accessory ingredients, and then, if necessary and/or desirable, dividing, shaping and/or packaging the product into a desired single- or multi-dose unit.

Relative amounts of the antigen, the adjuvant, the pharmaceutically acceptable excipient, and/or any additional ingredients in a pharmaceutical composition in accordance with the disclosure will vary, depending upon the identity, size, and/or condition of the subject treated and further depending upon the route by which the composition is to be administered. By way of example, the composition may comprise between 0.1% and 100%, e.g., between 0.5 and 50%, between 1-30%, between 5-80%, at least 80% (w/w) active ingredient.

In some embodiments, the vaccine composition described herein are formulated using one or more excipients to: (1) increase stability; (2) increase cell transfection; (3) permit the sustained or delayed release (e.g., from a depot formulation); (4) alter the biodistribution (e.g., target to specific tissues or cell types); (5) increase the translation of encoded protein in vivo; and/or (6) alter the release profile of encoded protein (antigen) in vivo. In addition to traditional excipients such as any and all solvents, dispersion media, diluents, or other liquid vehicles, dispersion or suspension aids, surface active agents, isotonic agents, thickening or emulsifying agents, preservatives, excipients can include, without limitation, lipidoids, liposomes, lipid nanoparticles, polymers, lipoplexes, core-shell nanoparticles, peptides, proteins, cells transfected with DNA or RNA vaccines (e.g., for transplantation into a subject), hyaluronidase, nanoparticle mimics and combinations thereof.

In some embodiments, the vaccine composition is formulated in an aqueous solution. In some embodiments, the vaccine composition is formulated in a nanoparticle. In some embodiments, the vaccine composition is formulated in a lipid nanoparticle. In some embodiments, the vaccine composition is formulated in a lipid-polycation complex, referred to as a lipid nanoparticle. The formation of the lipid nanoparticle may be accomplished by methods known in the art and/or as described in U.S. Pub. No. 20120178702, incorporated herein by reference. As a non-limiting example, the polycation may include a cationic peptide or a polypeptide such as, but not limited to, polylysine, polyornithine and/or polyarginine and the cationic peptides described in International Pub. No. WO2012013326 or US Patent Pub. No. US20130142818; each of which is incorporated herein by reference. In some embodiments, the vaccine composition is formulated in a lipid nanoparticle that includes a non-cationic lipid such as, but not limited to, cholesterol or dioleoyl phosphatidylethanolamine (DOPE).

A lipid nanoparticle formulation may be influenced by, but not limited to, the selection of the ionizable lipid component, the degree of ionizable lipid saturation, the nature of the PEGylation, ratio of all components and biophysical parameters such as size. In one example by Semple et al. (Nature Biotech. 2010 28:172-176; incorporated herein by reference), the lipid nanoparticle formulation is composed of 57.1% cationic lipid, 7.1% dipalmitoylphosphatidylcholine, 34.3% cholesterol, and 1.4% PEG-c-DMA. As another example, changing the composition of the cationic lipid can more effectively deliver siRNA to various antigen presenting cells (Basha et al. Mol Ther. 2011 19:2186-2200; incorporated herein by reference).

In some embodiments, lipid nanoparticle formulations may comprise 35 to 45% ionizable cationic lipid, 40% to 50% ionizable cationic lipid, 50% to 60% ionizable cationic lipid and/or 55% to 65% ionizable cationic lipid. In some embodiments, the ratio of lipid to RNA (e.g., mRNA) in lipid nanoparticles may be 5:1 to 20:1, 10:1 to 25:1, 15:1 to 30:1 and/or at least 30:1.

In some embodiments, the ratio of PEG in the lipid nanoparticle formulations may be increased or decreased and/or the carbon chain length of the PEG lipid may be modified from C14 to C18 to alter the pharmacokinetics and/or biodistribution of the lipid nanoparticle formulations. As a non-limiting example, lipid nanoparticle formulations may contain 0.5% to 3.0%, 1.0% to 3.5%, 1.5% to 4.0%, 2.0% to 4.5%, 2.5% to 5.0% and/or 3.0% to 6.0% of the lipid molar ratio of PEG-c-DOMG (R-3-[(ω-methoxy-poly (ethyleneglycol)2000) carbamoyl)]-1,2-dimyristyloxypropyl-3-amine) (also referred to herein as PEG-DOMG) as compared to the cationic lipid, DSPC and cholesterol. In some embodiments, the PEG-c-DOMG may be replaced with a PEG lipid such as, but not limited to, PEG-DSG (1,2-Distearoyl-sn-glycerol, methoxypolyethylene glycol), PEG-DMG (1,2-Dimyristoyl-sn-glycerol) and/or PEG-DPG (1,2-Dipalmitoyl-sn-glycerol, methoxypolyethylene glycol). The cationic lipid may be selected from any lipid known in the art such as, but not limited to, DLin-MC3-DMA, DLin-DMA, C12-200 and DLin-KC2-DMA.

In some embodiments, a vaccine formulation described herein is a nanoparticle that comprises at least one lipid (termed a "lipid nanoparticle" or "LNP"). The lipid may be selected from, but is not limited to, DLin-DMA, DLin-K-DMA, 98N12-5, C12-200, DLin-MC3-DMA, DLin-KC2-DMA, DODMA, PLGA, PEG, PEG-DMG, PEGylated lipids and amino alcohol lipids. In some embodiments, the lipid may be a cationic lipid such as, but not limited to, DLin-DMA, DLin-D-DMA, DLin-MC3-DMA, DLin-KC2-DMA, DODMA and amino alcohol lipids. The amino alcohol cationic lipid may be the lipids described in and/or made by the methods described in US Patent Publication No. US20130150625, incorporated herein by reference. As a non-limiting example, the cationic lipid may be 2-amino-3-[(9Z,12Z)-octadeca-9,12-dien-1-yloxy]-2-{[(9Z,2Z)-octadeca-9,12-dien-1-yloxy]methyl}propan-1-ol (Compound 1 in US20130150625); 2-amino-3-[(9Z)-octadec-9-en-1-yloxy]-2-{[(9Z)-octadec-9-en-1-yloxy]methyl}propan-1-ol (Compound 2 in US20130150625); 2-amino-3-[(9Z,12Z)-octadeca-9,12-dien-1-yloxy]-2-[(octyloxy)methyl]propan-1-ol (Compound 3 in US20130150625); and 2-(dimethylamino)-3-[(9Z,12Z)-octadeca-9,12-dien-1-yloxy]-2-{[(9Z,12Z)-octadeca-9,12-dien-1-yloxy]methyl}propan-1-ol (Compound 4 in US20130150625); or any pharmaceutically acceptable salt or stereoisomer thereof.

Lipid nanoparticle formulations typically comprise a lipid, in particular, an ionizable cationic lipid, for example, 2,2-dilinoleyl-4-dimethylaminoethyl-[1,3]-dioxolane (DLin-KC2-DMA), dilinoleyl-methyl-4-dimethylaminobutyrate (DLin-MC3-DMA), or di((Z)-non-2-en-1-yl) 9-((4-(dimethylamino) butanoyl)oxy) heptadecanedioate (L319), and further comprise a neutral lipid, a sterol and a molecule capable of reducing particle aggregation, for example a PEG or PEG-modified lipid.

In some embodiments, a lipid nanoparticle formulation consists essentially of (i) at least one lipid selected from the group consisting of 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino) butanoyl)oxy) heptadecanedioate (L319); (ii) a neutral lipid selected from DSPC, DPPC, POPC, DOPE and SM; (iii) a sterol, e.g., cholesterol; and (iv) a PEG-lipid, e.g., PEG-DMG or PEG-CDMA, in a molar ratio of 20-60% ionizable cationic lipid:5-25% neutral lipid:25-55% sterol:0.5-15% PEG-lipid.

Non-limiting examples of lipid nanoparticle compositions and methods of making them are described, for example, in Semple et al. (2010) Nat. Biotechnol. 28:172-176; Jayarama et al. (2012), Angew. Chem. Int. Ed., 51:8529-8533; and Maier et al. (2013) Molecular Therapy 21, 1570-1578 (the contents of each of which are incorporated herein by reference in their entirety).

The lipid nanoparticles described herein may be made in a sterile environment by the system and/or methods described in US Patent Publication No. US20130164400, incorporated herein by reference.

In some embodiments, the lipid nanoparticle formulation may be formulated in a nanoparticle such as a nucleic acid-lipid particle described in U.S. Pat. No. 8,492,359, the contents of which are incorporated herein by reference. As a non-limiting example, the lipid nanoparticle may comprise one or more active agents or therapeutic agents; one or more cationic lipids comprising from about 50 mol % to about 85 mol % of the total lipid present in the particle; one or more non-cationic lipids comprising from about 13 mol % to about 49.5 mol % of the total lipid present in the particle; and one or more conjugated lipids that inhibit aggregation of particles comprising from about 0.5 mol % to about 2 mol % of the total lipid present in the particle. The nucleic acid in the nanoparticle may be the polynucleotides described herein and/or are known in the art.

In some embodiments, the lipid nanoparticle formulation may be formulated by the methods described in International Publication Nos. WO2011127255 or WO2008103276, the contents of each of which are herein incorporated by reference in their entirety. As a non-limiting example, the antigen and the TLR2 agonist (e.g., a thiopnene compound) described herein may be encapsulated in LNP formulations as described in WO2011127255 and/or WO2008103276; the contents of each of which are herein incorporated by reference in their entirety.

In some embodiments, lipid nanoparticle formulations described herein may comprise a polycationic composition. As a non-limiting example, the polycationic composition may be selected from formula 1-60 of US Patent Publication No. US20050222064; the content of which is incorporated herein by reference. In another embodiment, the LNP formulations comprising a polycationic composition may be used for the delivery of the modified RNA described herein in vivo and/or in vitro.

In some embodiments, the lipid nanoparticle formulations described herein may additionally comprise a permeability enhancer molecule. Non-limiting permeability enhancer molecules are described in US Patent Publication No. US20050222064; the content of which is incorporated herein by reference.

In some embodiments, the vaccine compositions may be formulated in liposomes such as, but not limited to, DiLa2 liposomes (Marina Biotech, Bothell, WA), SMARTICLES® (Marina Biotech, Bothell, WA), neutral DOPC (1,2-dioleoyl-sn-glycero-3-phosphocholine) based liposomes (e.g., siRNA delivery for ovarian cancer (Landen et al. Cancer Biology & Therapy 2006 5 (12) 1708-1713); incorporated herein by reference) and hyaluronan-coated liposomes (Quiet Therapeutics, Israel).

In some embodiments, the vaccine compositions may be formulated in a lyophilized gel-phase liposomal composition as described in US Publication No. US2012060293, incorporated herein by reference.

In some embodiments, the vaccine compositions described herein may be formulated in lipid nanoparticles having a diameter from about 10 to about 100 nm such as, but not limited to, about 10 to about 20 nm, about 10 to about 30 nm, about 10 to about 40 nm, about 10 to about 50 nm, about 10 to about 60 nm, about 10 to about 70 nm, about 10 to about 80 nm, about 10 to about 90 nm, about 20 to about 30 nm, about 20 to about 40 nm, about 20 to about 50 nm, about 20 to about 60 nm, about 20 to about 70 nm, about 20 to about 80 nm, about 20 to about 90 nm, about 20 to about 100 nm, about 30 to about 40 nm, about 30 to about 50 nm, about 30 to about 60 nm, about 30 to about 70 nm, about 30 to about 80 nm, about 30 to about 90 nm, about 30 to about 100 nm, about 40 to about 50 nm, about 40 to about 60 nm, about 40 to about 70 nm, about 40 to about 80 nm, about 40 to about 90 nm, about 40 to about 100 nm, about 50 to about 60 nm, about 50 to about 70 nm about 50 to about 80 nm, about 50 to about 90 nm, about 50 to about 100 nm, about 60 to about 70 nm, about 60 to about 80 nm, about 60 to about 90 nm, about 60 to about 100 nm, about 70 to about 80 nm, about 70 to about 90 nm, about 70 to about 100 nm, about 80 to about 90 nm, about 80 to about 100 nm and/or about 90 to about 100 nm.

In some embodiments, the lipid nanoparticles may have a diameter from about 10 to 500 nm. In some embodiments, the lipid nanoparticle may have a diameter greater than 100 nm, greater than 150 nm, greater than 200 nm, greater than 250 nm, greater than 300 nm, greater than 350 nm, greater than 400 nm, greater than 450 nm, greater than 500 nm, greater than 550 nm, greater than 600 nm, greater than 650 nm, greater than 700 nm, greater than 750 nm, greater than 800 nm, greater than 850 nm, greater than 900 nm, greater than 950 nm or greater than 1000 nm.

In some embodiments, the vaccine composition is formulated in a liposome. Liposomes are artificially-prepared vesicles which may primarily be composed of a lipid bilayer and may be used as a delivery vehicle for the administration of nutrients and pharmaceutical formulations. Liposomes can be of different sizes such as, but not limited to, a multilamellar vesicle (MLV) which may be hundreds of nanometers in diameter and may contain a series of concentric bilayers separated by narrow aqueous compartments, a small unicellular vesicle (SUV) which may be smaller than 50 nm in diameter, and a large unilamellar vesicle (LUV) which may be between 50 and 500 nm in diameter. Liposome design may include, but is not limited to, opsonins or ligands in order to improve the attachment of liposomes to unhealthy tissue or to activate events such as, but not limited to, endocytosis. Liposomes may contain a low or a high pH in order to improve the delivery of the pharmaceutical formulations.

The formation of liposomes may depend on the physicochemical characteristics such as, but not limited to, the pharmaceutical formulation entrapped and the liposomal ingredients, the nature of the medium in which the lipid vesicles are dispersed, the effective concentration of the entrapped substance and its potential toxicity, any additional processes involved during the application and/or delivery of the vesicles, the optimization size, polydispersity and the shelf-life of the vesicles for the intended application, and the batch-to-batch reproducibility and possibility of large-scale production of safe and efficient liposomal products.

As a non-limiting example, liposomes such as synthetic membrane vesicles may be prepared by the methods, apparatus and devices described in US Patent Publication No. US20130177638, US20130177637, US20130177636, US20130177635, US20130177634, US20130177633, US20130183375, US20130183373 and US20130183372, the contents of each of which are incorporated herein by reference.

In some embodiments, the vaccine compositions described herein may include, without limitation, liposomes such as those formed from 1,2-dioleyloxy-N,N-dimethylaminopropane (DODMA) liposomes, DiLa2 liposomes from Marina Biotech (Bothell, WA), 1,2-dilinoleyloxy-3-dimethylaminopropane (DLin-DMA), 2,2-dilinoleyl-4-(2-dimethylaminoethyl)-[1,3]-dioxolane (DLin-KC2-DMA), and MC3 (US20100324120; incorporated herein by reference) and liposomes which may deliver small molecule drugs such as, but not limited to, DOXIL® from Janssen Biotech, Inc. (Horsham, PA).

In some embodiments, pharmaceutical compositions described herein may include, without limitation, liposomes such as those formed from the synthesis of stabilized plasmid-lipid particles (SPLP) or stabilized nucleic acid lipid particle (SNALP) that have been previously described and shown to be suitable for oligonucleotide delivery in vitro and in vivo (see Wheeler et al. Gene Therapy. 1999 6:271-281; Zhang et al. Gene Therapy. 1999 6:1438-1447; Jeffs et al. Pharm Res. 2005 22:362-372; Morrissey et al., Nat Biotechnol. 2005 2:1002-1007; Zimmermann et al., Nature. 2006 441:111-114; Heyes et al. J Contr Rel. 2005 107:276-287; Semple et al. Nature Biotech. 2010 28:172-176; Judge et al. J Clin Invest. 2009 119:661-673; deFougerolles Hum Gene Ther. 2008 19:125-132; U.S. Patent Publication No US20130122104; all of which are incorporated herein in their entireties). The original manufacture method by Wheeler et al. was a detergent dialysis method, which was later improved by Jeffs et al. and is referred to as the spontaneous vesicle formation method. The liposome formulations are composed of 3 to 4 lipid components in addition to the polynucleotide. As an example a liposome can contain, but is not limited to, 55% cholesterol, 20% disteroylphosphatidyl choline (DSPC), 10% PEG-S-DSG, and 15% 1,2-dioleyloxy-N,N-dimethylaminopropane (DODMA), as described by Jeffs et al. As another example, certain liposome formulations may contain, but are not limited to, 48% cholesterol, 20% DSPC, 2% PEG-c-DMA, and 30% cationic lipid, where the cationic lipid can be 1,2-distearloxy-N,N-dimethylaminopropane (DSDMA), DODMA, DLin-DMA, or 1,2-dilinolenyloxy-3-dimethyl-aminopropane (DLenDMA), as described by Heyes et al.

In some embodiments, liposomes may be formulated for targeted delivery. As a non-limiting example, the liposome may be formulated for targeted delivery to the liver. The liposome used for targeted delivery may include, but is not limited to, the liposomes described in and methods of making liposomes described in US Patent Publication No. US20130195967, the contents of which are incorporated herein by reference.

In some embodiments, the antigen and/or the TLR2 agonist (e.g., thiophnene compound) may be formulated in a cationic oil-in-water emulsion where the emulsion particle comprises an oil core and a cationic lipid which can interact with the polynucleotide anchoring the molecule to the emulsion particle (see International Pub. No. WO2012006380; incorporated herein by reference).

In some embodiments, the antigen and/or the TLR2 agonist (e.g., thiophnene compound) may be formulated in a water-in-oil emulsion comprising a continuous hydrophobic phase in which the hydrophilic phase is dispersed. As a non-limiting example, the emulsion may be made by the methods described in International Publication No. WO201087791, the contents of which are incorporated herein by reference.

The antigen, the TLR2 agonist (e.g., thiophnene compound), and/or optionally the second adjuvant may be formulated using any of the methods described herein or known in the art separately or together. For example, the antigen and the TLR2 agonist (e.g., thiophnene compound) may be formulated in one lipid nanoparticle or two separately lipid nanoparticles. In some embodiments, the antigen, the TLR2 agonist (e.g., thiophnene compound) are formulated in the same aqueous solution or two separate aqueous solutions. In some embodiments, the antigen, the TLR2 agonist (e.g., thiophnene compound), and/or optionally the second adjuvant is adsorbed onto alum (e.g., as described in Jones et al., Journal of Biological Chemistry 280, 13406-13414, 2005, incorporated herein by reference).

In some embodiments, the vaccine composition described herein comprises two or more adjuvants (also referred to as an "adjuvant system"). The adjuvant system comprises the TLR2 agonist (e.g., thiophnene compound) and one or more other adjuvants described herein.

Methods

Other aspects of the present disclosure provide methods of enhancing an immune response in a subject. In some embodiments, the methods comprise administering to the subject an effective amount of an TLR2 agonist (e.g., thiophnene compound) described herein (e.g., for enhancing an innate immune response, including induction of heterologous or "trained" immunity or innate memory). In some embodiments, the methods comprising administering to the subject an effective amount of an TLR2 agonist (e.g., thiophnene compound) and an effective amount of an antigen (e.g., for enhancing an antigen-specific immune response). In some embodiments, the TLR2 agonist (e.g., thiophnene compound) are administered separately from the antigen. In some embodiments, the TLR2 agonist (e.g., thiophnene compound) is administered prior to administering the antigen. In some embodiments, the TLR2 agonist (e.g., thiophnene compound) is administered after administering the antigen. In some embodiments, the TLR2 agonist (e.g., thiophnene compound) and the antigen are administered simultaneously. In some embodiment, TLR2 agonist (e.g., thiophnene compound) and the antigen as an admixture.

The antigen and/or the TLR2 agonist (e.g., thiophene compound) (e.g., the antigen alone, the TLR2 agonist (e.g., thiophnene compound) alone, or the antigen and the TLR2 agonist (e.g., thiophnene compound) together) described herein elicits an immune response in the subject. In some embodiments, the antigen and/or the TLR2 agonist (e.g., thiophnene compound) activates cytokine and/or chemokine (e.g., IL1β, IL-6, IL-12, TNF, and/or CCL3) production. In some embodiments, the immune response is an innate immune response. In some embodiments, the immune response is an adaptive immune response specific to the antigen in the composition or vaccine. In some embodiments, the antigen and/or the TLR2 agonist (e.g., thiophnene compound) activates B cell immunity. In some embodiments, the antigen and/or the TLR2 agonist (e.g., thiophnene compound) elicits antibody production. In some embodiments, the composition or the vaccine activates cytotoxic T cells specific to the antigen.

In some embodiments, the TLR2 agonist (e.g., thiophene compound), whether administered alone or in an admixture with an antigen, enhance the innate immune response, compared to without the TLR2 agonist (e.g., thiophene compound) or when the antigen is administered alone. In some embodiments, the TLR2 agonist (e.g., thiophene compound) activates peripheral blood mononuclear cells (PBMCs). In some embodiments, the number of PBMCs that are activated is increased by at least 20% in the presence of an TLR2 agonist (e.g., thiophene compound), compared to without the TLR2 agonist (e.g., thiophene compound) or when the antigen is administered alone. For example, the number of PBMCs that are activated may be increased by at least 20%, at least 30%, at least 40%, at least 50%, at least 60%, at least 70%, at least 80%, at least 90%, at least 100%, at least 2-fold, at least 5-fold, at least 10-fold, at least 100-fold, at least 1000-fold or more, in the presence of an TLR2 agonist (e.g., thiophene compound), compared to without the TLR2 agonist (e.g., thiophene compound) or when the antigen is administered alone. In some embodiments, the number of PBMCs that are activated is increased by 20%, 30%, 40%, 50%, 60%, 70%, 80%, 90%, 100%, 2-fold, 5-fold, 10-fold, 100-fold, 1000-fold or more, in the presence of an TLR2 agonist (e.g., thiophene compound), compared to without the TLR2 agonist (e.g., thiophene compound) or when the antigen is administered alone.

In some embodiments, the TLR2 agonist (e.g., thiophene compound) activates an pattern recognition receptor (PRR). In some embodiments, the PRR is selected from the group consisting of Toll-like receptors (e.g., TLR2), NOD1/2, RIG-1/MDA-5, C-type lectins, and STING. In some embodiments, the Toll-like receptor is Toll-like receptor-1, -2, -3, -4, -5, -6, -9, -10. In some embodiments, the Toll-like receptor is Toll-like receptor-7 or -8. In some embodiments, the number of PRRs that are activated is increased by at least 20% in the presence of a TLR2 agonist (e.g., thiophene compound), compared to without the TLR2 agonist (e.g., thiophene compound) or when the antigen is administered alone. For example, the number of PRRs that are activated may be increased by at least 20%, at least 30%, at least 40%, at least 50%, at least 60%, at least 70%, at least 80%, at least 90%, at least 100%, at least 2-fold, at least 5-fold, at least 10-fold, at least 100-fold, at least 1000-fold or more, in the presence of an TLR2 agonist (e.g., thiophene compound), compared to without the TLR2 agonist (e.g., thiophene compound) or when the antigen is administered alone. In some embodiments, the number of PRRs that are activated is increased by 20%, 30%, 40%, 50%, 60%, 70%, 80%, 90%, 100%, 2-fold, 5-fold, 10-fold, 100-fold, 1000-fold or more, in the presence of an TLR2 agonist (e.g., thiophene compound), compared to without the TLR2 agonist (e.g., thiophene compound) or when the antigen is administered alone.

In some embodiments, the TLR2 agonist (e.g., thiophene compound) induces the production of a proinflammatory cytokine (e.g., TNF, IL-12, IL-6, or IL1-β) and/or chemokines (e.g., CCL3) in the subject. In some embodiments, the level of proinflammatory cytokines and/or chemokines (e.g., CCL3) is increased by at least 20% in the presence of an TLR2 agonist (e.g., thiophene compound), compared to without the TLR2 agonist (e.g., thiophene compound) or when the antigen is administered alone. For example, the level of proinflammatory cytokines (e.g., TNF, IL-12, IL-6, or IL1-β) and/or chemokines (e.g., CCL3) may be increased by at least 20%, at least 30%, at least 40%, at least 50%, at least 60%, at least 70%, at least 80%, at least 90%, at least 100%, at least 2-fold, at least 5-fold, at least 10-fold, at least 100-fold, at least 1000-fold or more, in the presence of an TLR2 agonist (e.g., thiophene compound), compared to without the TLR2 agonist (e.g., thiophene compound) or when the antigen is administered alone. In some embodiments, the level of proinflammatory cytokines (e.g., TNF, IL-12, IL-6, or IL1-B) and/or chemokines (e.g., CCL3) is increased by 20%, 30%, 40%, 50%, 60%, 70%, 80%, 90%, 100%, 2-fold, 5-fold, 10-fold, 100-fold, 1000-fold or more, in the presence of an TLR2 agonist (e.g., thiophene compound), compared to without the TLR2 agonist (e.g., thiophene compound) or when the antigen is administered alone.

In some embodiments, the TLR2 agonist (e.g., thiophene compound) enhances innate immune memory (also referred to as trained immunity). "Innate immune memory" confers heterologous immunity that provides broad protection against a range of pathogens. In some embodiments, the innate immune memory is increased by at least 20% in the presence of an TLR2 agonist (e.g., thiophene compound), compared to without the TLR2 agonist (e.g., thiophene compound) or when the antigen is administered alone. For example, the innate immune memory may be increased by at least 20%, at least 30%, at least 40%, at least 50%, at least 60%, at least 70%, at least 80%, at least 90%, at least 100%, at least 2-fold, at least 5-fold, at least 10-fold, at least 100-fold, at least 1000-fold or more, in the presence of an TLR2 agonist (e.g., thiophene compound), compared to without the TLR2 agonist (e.g., thiophene compound) or when the antigen is administered alone. In some embodiments, the innate immune memory is increased by 20%, 30%, 40%, 50%, 60%, 70%, 80%, 90%, 100%, 2-fold, 5-fold, 10-fold, 100-fold, 1000-fold or more, in the presence of an TLR2 agonist (e.g., thiophene compound), compared to without the TLR2 agonist (e.g., thiophene compound) or when the antigen is administered alone.

In some embodiments, the TLR2 agonist (e.g., thiophene compound), when administered as an admixture with an antigen (e.g., the vaccine composition described herein), enhances the anti-specific immune response against the antigen or against the invading agent where the antigen is derived from (e.g., a microbial pathogen or cancer), compared to without the TLR2 agonist (e.g., thiophene compound, i.e., when the antigen is administered alone. In some embodiments, the TLR2 agonist (e.g., thiophene compound) enhances the production of antigen-specific antibody titer (e.g., by at least 20%) in the subject, compared to without the TLR2 agonist (e.g., thiophene compound), i.e., when the antigen is administered alone. For example, the TLR2 agonist (e.g., thiophene compound) may enhance the production of antigen-specific antibody titer by at least 20%, at least 30%, at least 40%, at least 50%, at least 60%, at least 70%, at least 80%, at least 90%, at least 100%, at least 2-fold, at least 5-fold, at least 10-fold, at least 100-fold, at least 1000-fold or more. in the subject, compared to without the TLR2 agonist (e.g., thiophene compound, i.e., when the antigen is administered alone. In some embodiments, the TLR2 agonist (e.g., thiophene compound) enhances the production of antigen-specific antibody titer by 20%, 30%, 40%, 50%, 60%, 70%, 80%, 90%, 100%, 2-fold, 5-fold, 10-fold, 100-fold, 1000-fold or more, in the presence of an TLR2 agonist (e.g., thiophene compound), compared to without the TLR2 agonist (e.g., thiophene compound), i.e., when the antigen is administered alone. One skilled in the art is familiar with how to evaluate the level of an antibody titer, e.g., by ELISA.

In some embodiments, the TLR2 agonist (e.g., thiophene compound) enhances the activation of cytotoxic T-cells (e.g., by at least 20%) in the subject, compared to without the TLR2 agonist (e.g., thiophene compound), i.e., when the antigen is administered alone. For example, the TLR2 agonist (e.g., thiophene compound) may enhance activation of cytotoxic T-cells by at least 20%, at least 30%, at least 40%, at least 50%, at least 60%, at least 70%, at least 80%, at least 90%, at least 100%, at least 2-fold, at least 5-fold, at least 10-fold, at least 100-fold, at least 1000-fold or more, in the subject, compared to without the TLR2 agonist (e.g., thiophene compound), i.e., when the antigen is administered alone. In some embodiments, the TLR2 agonist (e.g., thiophene compound) enhances the activation of cytotoxic T-cells by 20%, 30%, 40%, 50%, 60%, 70%, 80%, 90%, 100%, 2-fold, 5-fold, 10-fold, 100-fold, 1000-fold or more, in the presence of an TLR2 agonist (e.g., thiophene compound), compared to without the TLR2 agonist (e.g., thiophene compound), i.e., when the antigen is administered alone.

It has been demonstrated that the innate immune system plays a crucial role in the control of initiation of the adaptive immune response and in the induction of appropriate cell effector responses. (Fearon et al. (1996) Science 272:50-3; Medzhitov et al. (1997) Cell 91:295-8, incorporated herein by reference). As such, in some embodiments, the TLR2 agonist (e.g., thiophene compound) enhances the innate immune response in a subject (e.g., when administered alone or in an admixture with an antigen), which in turn enhances the adaptive immune response against the antigen in the subject. This is particular useful in subjects that have a undeveloped (e.g., in an neonatal infant), weak (e.g., in an elderly), or compromised immune systems (e.g., in a patient with primary immunodeficiency or acquired immunodeficiency secondary to HIV patient infection or a cancer patient undergoing with or without chemotherapy and/or radiation therapy).

In some embodiments, the TLR2 agonist (e.g., thiophene compound) prolongs the effect of a vaccine (e.g., by at least 20%) in the subject, compared to without the TLR2 agonist (e.g., thiophene compound) (i.e., when the antigen is administered alone). For example, the TLR2 agonist (e.g., thiophene compound) may prolong the effect of a vaccine by at least 20%, at least 30%, at least 40%, at least 50%, at least 60%, at least 70%, at least 80%, at least 90%, at least 100%, at least 2-fold, at least 5-fold, at least 10-fold, at least 100-fold, at least 1000-fold or more. in the subject, compared to without the TLR2 agonist (e.g., thiophene compound), i.e., when the antigen is administered alone. In some embodiments, the TLR2 agonist (e.g., thiophene compound) prolongs the effect of a vaccine by 20%, 30%, 40%, 50%, 60%, 70%, 80%, 90%, 100%, 2-fold, 5-fold, 10-fold, 100-fold, 1000-fold or more, in the presence of an TLR2 agonist (e.g., thiophene compound), compared to without the TLR2 agonist (e.g., thiophene compound), i.e., when the antigen is administered alone.

In some embodiments, the TLR2 agonist (e.g., thiophene compound) increases rate of (accelerates) an immune response, compared to without the TLR2 agonist (e.g., thiophene compound), i.e., when the antigen is administered alone. For example, the TLR2 agonist (e.g., thiophene compound) may increase the rate of an immune response by at least 20%, at least 30%, at least 40%, at least 50%, at least 60%, at least 70%, at least 80%, at least 90%, at least 100%, at least 2-fold, at least 5-fold, at least 10-fold, at least 100-fold, at least 1000-fold or more. in the subject, compared to without the TLR2 agonist (e.g., thiophene compound), i.e., when the antigen is administered alone. In some embodiments, the TLR2 agonist (e.g., thiophene compound) increases the rate of an immune response by 20%, 30%, 40%, 50%, 60%, 70%, 80%, 90%, 100%, 2-fold, 5-fold, 10-fold, 100-fold, 1000-fold or more, in the presence of an TLR2 agonist (e.g., thiophene compound), compared to without the TLR2 agonist (e.g., thiophene compound), i.e., when the antigen is administered alone. "Increase the rate of immune response" mean it takes less time for the immune system of a subject to react to an invading agent (e.g., a microbial pathogen).

In some embodiments, the antigen produces a same level of immune response against the antigen at a lower dose in the presence of the TLR2 agonist (e.g., thiophene compound), compared to without the TLR2 agonist (e.g., thiophene compound), i.e., when the antigen is administered alone. In some embodiments, the amount of antigen needed to produce the same level of immune response is reduced by at least 20% in the presence of the TLR2 agonist (e.g., thiophene compound), compared to without the TLR2 agonist (e.g., thiophene compound), i.e., when the antigen is administered alone. For example, the amount of antigen needed to produce the same level of immune response may be reduced by at least 20%, at least 30%, at least 40%, at least 50%, at least 60%, at least 70%, at least 80%, at least 90%, at least 95%, at least 99% or more, in the presence of the TLR2 agonist (e.g., thiophene compound), compared to without the TLR2 agonist (e.g., thiophene compound), i.e., when the antigen is administered alone. In some embodiments, the amount of antigen needed to produce the same level of immune response is reduced by at 20%, 30%, 40%, 50%, 60%, 70%, 80%, 90%, 95%, 99% or more, in the presence of the TLR2 agonist (e.g., thiophene compound), compared to without the TLR2 agonist (e.g., thiophene compound), i.e., when the antigen is administered alone.

The prophylactic or therapeutic use of the TLR2 agonist (e.g., thiophene compound), or the composition or vaccine composition described herein is also within the scope of the present disclosure. In some embodiments, the composition or vaccine composition described herein are used in methods of vaccinating a subject by prophylactically administering to the subject an effective amount of the composition or vaccine composition described herein. "Vaccinating a subject" refer to a process of administering an immunogen, typically an antigen formulated into a vaccine, to the subject in an amount effective to increase or activate an immune response against the antigen and, thus, against a pathogen displaying the antigen. In some embodiments, the terms do not require the creation of complete immunity against the pathogen. In some embodiments, the terms encompass a clinically favorable enhancement of an immune response toward the antigen or pathogen. Methods for immunization, including formulation of a vaccine composition and selection of doses, routes of administration and the schedule of administration (e.g. primary dose and one or more booster doses), are well known in the art. In some embodiments, vaccinating a subject reduces the risk of developing a disease (e.g., an infectious disease or cancer) in a subject.

In some embodiments, the TLR2 agonist (e.g., thiophene compound) alone, or composition or vaccine composition comprising an antigen and an TLR2 agonist (e.g., thiophene compound) described herein are used in methods of treating a disease (e.g., an infectious disease, allergy, or cancer) by administering to the subject an effective amount of the composition or vaccine composition described herein.

In some embodiments, the disease is an infectious disease. An "infectious disease" refers to an illness caused by a pathogenic biological agent that results from transmission from an infected person, animal, or reservoir to a susceptible host, either directly or indirectly, through an intermediate plant or animal host, vector, or inanimate environment. See Last J M. ed. A dictionary of epidemiology. 4th ed., New York: Oxford University Press, 1988. Infectious disease is also known as transmissible disease or communicable disease. In some embodiments, infectious diseases may be asymptomatic for much or even all of their course in a given host. Infectious pathogens include some viruses, bacteria, fungi, protozoa, multicellular parasites, and aberrant proteins known as prions. In some embodiments, the infectious disease is caused by any of the microbial pathogens (e.g., a bacterium, a *mycobacterium*, a fungus, a virus, a parasite or a prion) described herein or known to one skilled in the art. In some embodiments, the infectious disease is caused by *Plasmodium* spp. (malaria), *Bacillus anthracis* (anthrax), *Bordetella pertussis* (whooping cough), *Corynebacterium diphtheriae* (diphtheria), *Clostridium tetani* (tetanus), *Haemophilus influenzae* type b, pneumococcus (pneumococcal infections), Staphylococci spp., Group A or B streptococci, *Mycobacterium tuberculosis, Neiserria meningitidis* (meningococcal disease), *Salmonella typhi* (typhoid), *Vibrio cholerae* (Cholera), or *Yersinia pestis* (plague). In some embodiments, the infectious disease is caused by adenovirus, enterovirus such as poliomyelitis (polio), dengue virus, Ebola virus, herpes viruses such as herpes simplex virus, cytomegalovirus and varicella-zoster (chickenpox and shingles), measles, mumps, rubella, hepatitis-A, —B, or —C, human papilloma virus, Influenza virus, rabies, Japanese encephalitis, rotavirus, human immunodeficiency virus (HIV), respiratory syncytial virus (RSV), smallpox, yellow fever, dengue virus, or Zika Virus. In some embodiments, the infectious disease is caused by malaria, *Leishmania*, or a helminth. In some embodiments, the infectious disease is caused by *Candida* spp., *Aspergillus* spp., *Cryptococcus* spp., *Mucormycete, Blastomyces dermatitidis, Histoplasma*

*capsulatum*, or *Sporothrix schenckii*. In some embodiments, the infectious disease is caused by prion. In some embodiments, the infectious disease is sepsis.

In some embodiments, the composition or vaccine composition may be administered in combination with another therapeutic agent for the infectious diseases. Such other therapeutic agents may be, without limitation: antibiotics, anti-viral agents, anti-fungal agents, or anti-parasitic agents. One skilled in the art is familiar with how to select or administer the additional therapeutic agent based on the disease to be treated.

In some embodiments, the disease is allergy (e.g., allergic rhinitis) or asthma. It has been demonstrated that Th1/Th2 imbalance results in the clinical manifestation of allergy or asthma (e.g., as described in Ngoc et al., Curr Opin Allergy Clin Immunol. 2005 April; 5 (2): 161-6, incorporated herein by reference). The TLR2 agonist (e.g., thiophene compound) described herein may be able to restore Th1/Th2 balance and possess therapeutic potential to allergy or asthma.

In some embodiments, the disease is cancer. Vaccine compositions comprising cancer-specific antigens and the TLR2 agonists may be used in cancer immunotherapy by eliciting cancer-specific immune response against the cancer. The term "cancer" refers to a class of diseases characterized by the development of abnormal cells that proliferate uncontrollably and have the ability to infiltrate and destroy normal body tissues. See, e.g., *Stedman's Medical Dictionary*, 25th ed.; Hensyl ed.; Williams & Wilkins: Philadelphia, 1990. Exemplary cancers include, but are not limited to, hematological malignancies. Additional exemplary cancers include, but are not limited to, lung cancer (e.g., bronchogenic carcinoma, small cell lung cancer (SCLC), non-small cell lung cancer (NSCLC), adenocarcinoma of the lung); kidney cancer (e.g., nephroblastoma, a.k.a. Wilms' tumor, renal cell carcinoma); acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma); choriocarcinoma; chordoma; craniopharyngioma; colorectal cancer (e.g., colon cancer, rectal cancer, colorectal adenocarcinoma); connective tissue cancer; epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarcinoma); Ewing's sarcoma; ocular cancer (e.g., intraocular melanoma, retinoblastoma); familiar hypereosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); heavy chain disease (e.g., alpha chain disease, gamma chain disease, mu chain disease; hemangioblastoma; hypopharynx cancer; inflammatory myofibroblastic tumors; immunocytic amyloidosis; liver cancer (e.g., hepatocellular cancer (HCC), malignant hepatoma); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendoctrine tumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic andenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva). In some embodiments, the cancer treated using the composition and methods of the present disclosure is melanoma.

In some embodiments, additional anti-cancer agents may be administered in combination with the composition or vaccine composition described herein. In some embodiments, the anti-cancer agent is selected from the group consisting of: small molecules, oligonucleotides, polypeptides, and combinations thereof. In some embodiments, the anti-cancer agent is a chemotherapeutic agent. In some embodiments, the chemotherapeutic agent is selected from the group consisting of: Actinomycin, All-trans retinoic acid, Azacitidine, Azathioprine, Bleomycin, Bortezomib, Carboplatin, Capecitabine, Cisplatin, Chlorambucil, Cyclophosphamide, Cytarabine, Daunorubicin, Docetaxel, Doxifluridine, Doxorubicin, Epirubicin, Epothilone, Etoposide, Fluorouracil, Gemcitabine, Hydroxyurea, Idarubicin, Imatinib, Irinotecan, Mechlorethamine, Mercaptopurine, Methotrexate, Mitoxantrone, Oxaliplatin, Paclitaxel, Pemetrexed, Teniposide, Tioguanine, Topotecan, Valrubicin, Vinblastine, Vincristine, Vindesine, and Vinorelbine. In some embodiments, the chemotherapeutic agent is Doxorubicin.

In some embodiments, the anti-cancer agent is an immune checkpoint inhibitor. An "immune checkpoint" is a protein in the immune system that either enhances an immune response signal (co-stimulatory molecules) or reduces an immune response signal. Many cancers protect themselves from the immune system by exploiting the inhibitory immune checkpoint proteins to inhibit the T cell signal. Exemplary inhibitory checkpoint proteins include, without limitation, Cytotoxic T-Lymphocyte-Associated protein 4 (CTLA-4), Programmed Death 1 receptor (PD-1), T-cell Immunoglobulin domain and Mucin domain 3 (TIM3), Lymphocyte Activation Gene-3 (LAG3), V-set domain-containing T-cell activation inhibitor 1 (VTVN1 or B7-H4), Cluster of Differentiation 276 (CD276 or B7-H3), B and T Lymphocyte Attenuator (BTLA), Galectin-9 (GAL9), Checkpoint kinase 1 (Chk1), Adenosine A2A receptor (A2aR), Indoleamine 2,3-dioxygenase (IDO), Killer-cell Immunoglobulin-like Receptor (KIR), Lymphocyte Activation Gene-3 (LAG3), and V-domain Ig suppressor of T cell activation (VISTA).

Some of these immune checkpoint proteins need their cognate binding partners, or ligands, for their immune inhibitory activity. For example, A2AR is the receptor of adenosine A2A and binding of A2A to A2AR activates a negative immune feedback loop. As another example, PD-1 associates with its two ligands, PD-L1 and PD-L2, to down regulate the immune system by preventing the activation of T-cells. PD-1 promotes the programmed cell death of antigen specific T-cells in lymph nodes and simultaneously reduces programmed cell death of suppressor T cells, thus achieving its immune inhibitory function. As yet another example, CTLA4 is present on the surface of T cells, and when bound to its binding partner CD80 or CD86 on the surface of antigen-present cells (APCs), it transmits an inhibitory signal to T cells, thereby reducing the immune response.

An "immune checkpoint inhibitor" is a molecule that prevents or weakens the activity of an immune checkpoint protein, For example, an immune checkpoint inhibitor may inhibit the binding of the immune checkpoint protein to its cognate binding partner, e.g., PD-1, CTLA-4, or A2aR. In some embodiments, the immune checkpoint inhibitor is a small molecule. In some embodiments, the immune checkpoint inhibitors is a nucleic acid aptamer (e.g., a siRNA targeting any one of the immune checkpoint proteins). In some embodiments, the immune checkpoint inhibitor is a recombinant protein. In some embodiments, the immune checkpoint inhibitor is an antibody. In some embodiments, the antibody comprises an anti-CTLA-4, anti-PD-1, anti-PD-L1, anti-TIM3, anti-LAG3, anti-B7-H3, anti-B7-H4, anti-BTLA, anti-GAL9, anti-Chk, anti-A2aR, anti-IDO, anti-KIR, anti-LAG3, anti-VISTA antibody, or a combination of any two or more of the foregoing antibodies. In some embodiments, the immune checkpoint inhibitor is a monoclonal antibody. In some embodiments, the immune checkpoint inhibitor comprises anti-PD1, anti-PD-L1, anti-CTLA-4, or a combination of any two or more of the foregoing antibodies. For example, the anti-PD-1 antibody is pembrolizumab (Keytruda®) or nivolumab (Opdivo®) and the anti-CTLA-4 antibody is ipilimumab (Yervoy®). Thus, in some embodiments, the immune checkpoint inhibitor comprises pembrolizumab, nivolumab, ipilimumab, or any combination of two or more of the foregoing antibodies. The examples described herein are not meant to be limiting and that any immune checkpoint inhibitors known in the art and any combinations thereof may be used in accordance with the present disclosure.

Additional exemplary agents that may be used in combination with the compositions described herein include, but are not limited to, anti-proliferative agents, anti-cancer agents, anti-angiogenesis agents, anti-inflammatory agents, immunosuppressants, anti-bacterial agents, anti-viral agents, cardiovascular agents, cholesterol-lowering agents, anti-diabetic agents, anti-allergic agents, contraceptive agents, pain-relieving agents, and a combination thereof. In some embodiments, the additional agent is an anti-proliferative agent (e.g., anti-cancer agent). In some embodiments, the additional pharmaceutical agent is an anti-leukemia agent. In some embodiments, the additional pharmaceutical agent is ABITREXATE (methotrexate), ADE, Adriamycin RDF (doxorubicin hydrochloride), Ambochlorin (chlorambucil), ARRANON (nelarabine), ARZERRA (ofatumumab), BOSULIF (bosutinib), BUSULFEX (busulfan), CAMPATH (alemtuzumab), CERUBIDINE (daunorubicin hydrochloride), CLAFEN (cyclophosphamide), CLOFAREX (clofarabine), CLOLAR (clofarabine), CVP, CYTOSAR-U (cytarabine), CYTOXAN (cyclophosphamide), ERWINAZE (Asparaginase *Erwinia Chrysanthemi*), FLUDARA (fludarabine phosphate), FOLEX (methotrexate), FOLEX PFS (methotrexate), GAZYVA (obinutuzumab), GLEEVEC (imatinib mesylate), Hyper-CVAD, ICLUSIG (ponatinib hydrochloride), IMBRUVICA (ibrutinib), LEUKERAN (chlorambucil), LINFOLIZIN (chlorambucil), MARQIBO (vincristine sulfate liposome), METHOTREXATE LPF (methorexate), MEXATE (methotrexate), MEXATE-AQ (methotrexate), mitoxantrone hydrochloride, MUSTARGEN (mechlorethamine hydrochloride), MYLERAN (busulfan), NEOSAR (cyclophosphamide), ONCASPAR (Pegaspargase), PURINETHOL (mercaptopurine), PURIXAN (mercaptopurine), Rubidomycin (daunorubicin hydrochloride), SPRYCEL (dasatinib), SYNRIBO (omacetaxine mepesuccinate), TARABINE PFS (cytarabine), TASIGNA (nilotinib), TREANDA (bendamustine hydrochloride), TRISENOX (arsenic trioxide), VINCASAR PFS (vincristine sulfate), ZYDELIG (idelalisib), or a combination thereof. In some embodiments, the additional pharmaceutical agent is an anti-lymphoma agent. In some embodiments, the additional pharmaceutical agent is ABITREXATE (methotrexate), ABVD, ABVE, ABVE-PC, ADCETRIS (brentuximab vedotin), ADRIAMYCIN PFS (doxorubicin hydrochloride), ADRIAMYCIN RDF (doxorubicin hydrochloride), AMBOCHLORIN (chlorambucil), AMBOCLORIN (chlorambucil), ARRANON (nelarabine), BEACOPP, BECENUM (carmustine), BELEODAQ (belinostat), BEXXAR (tositumomab and iodine I 131 tositumomab), BICNU (carmustine), BLENOXANE (bleomycin), CARMUBRIS (carmustinc), CHOP, CLAFEN (cyclophosphamide), COPP, COPP-ABV, CVP, CYTOXAN (cyclophosphamide), DEPOCYT (liposomal cytarabine), DTIC-DOME (dacarbazine), EPOCH, FOLEX (methotrexate), FOLEX PFS (methotrexate), FOLOTYN (pralatrexate), HYPER-CVAD, ICE, IMBRUVICA (ibrutinib), INTRON A (recombinant interferon alfa-2b), ISTODAX (romidepsin), LEUKERAN (chlorambucil), LINFOLIZIN (chlorambucil), Lomustine, MATULANE (procarbazine hydrochloride), METHOTREXATE LPF (methotrexate), MEXATE (methotrexate), MEXATE-AQ (methotrexate), MOPP, MOZOBIL (plerixafor), MUSTARGEN (mechlorethamine hydrochloride), NEOSAR (cyclophosphamide), OEPA, ONTAK (denileukin diftitox), OPPA, R—CHOP, REVLIMID (lenalidomide), RITUXAN (rituximab), STANFORD V, TREANDA (bendamustine hydrochloride), VAMP, VELBAN (vinblastine sulfate), VELCADE (bortezomib), VELSAR (vinblastine sulfate), VINCASAR PFS (vincristine sulfate), ZEVALIN (ibritumomab tiuxetan), ZOLINZA (vorinostat), ZYDELIG (idelalisib), or a combination thereof. In some embodiments, the additional pharmaceutical agent is REVLIMID (lenalidomide), DACOGEN (decitabine), VIDAZA (azacitidine), CYTOSAR-U (cytarabine), IDAMYCIN (idarubicin), CERUBIDINE (daunorubicin), LEUKERAN (chlorambucil), NEOSAR (cyclophosphamide), FLUDARA (fludarabine), LEUSTATIN (cladribine), or a combination thereof. In some embodiments, the additional pharmaceutical agent is ABITREXATE (methotrexate), ABRAXANE (paclitaxel albumin-stabilized nanoparticle formulation), AC, AC-T, ADE, ADRIAMYCIN PFS (doxorubicin hydrochloride), ADRUCIL (fluorouracil), AFINITOR (everolimus), AFINITOR DISPERZ, (everolimus), ALDARA (imiquimod), ALIMTA (pemetrexed disodium), AREDIA (pamidronate disodium), ARIMIDEX (anastrozole), AROMASIN (exemestane), AVASTIN (bevacizumab), BECENUM (carmustine), BEP, BICNU (carmustine), BLENOXANE (bleomycin), CAF, CAMPTOSAR (irinotecan hydrochloride), CAPOX, CAPRELSA (vandetanib), CARBOPLATIN-TAXOL, CARMUBRIS (carmustine), CASODEX (bicalutamide), CEENU (lomustine), CERUBIDINE (daunorubicin hydrochloride), CERVARIX (recombinant HPV bivalent vaccine), CLAFEN (cyclophosphamide), CMF, COMETRIQ (cabozantinib-s-malate), COSMEGEN (dactinomycin), CYFOS (ifosfamide), CYRAMZA (ramucirumab), CYTOSAR-U (cytarabine), CYTOXAN (cyclophosphamide), DACOGEN (decitabine), DEGARELIX, DOXIL (doxorubicin hydrochloride liposome), DOXORUBICIN HYDROCHLORIDE, DOX-SL (doxorubicin hydrochloride liposome), DTIC-DOME (dacarbazine), EFUDEX (fluorouracil), ELLENCE (epirubicin hydrochloride), ELOXATIN (oxaliplatin), ERBITUX (cetuximab), ERIVEDGE (vismodegib), ETOPOPHOS (etoposide phosphate), EVACET (doxorubicin hydrochloride liposome), FARESTON (toremifene), FASLODEX (fulvestrant), FEC, FEMARA (letrozole), FLUOROPLEX (fluorouracil), FOLEX (methotrexate), FOLEX PFS (methotrexate), FOLFIRI, FOLFIRI-BEVACIZUMAB, FOLFIRI-CETUXIMAB, FOLFIRINOX, FOLFOX, FU-LV, GARDASIL (recombinant human papillomavirus (HPV) quadrivalent vaccine), GEMCITABINE-CISPLATIN, GEMCITABINE-OXALIPLATIN, GEMZAR (gemcitabine hydrochloride), GILOTRIF (afatinib dimaleate), GLEEVEC (imatinib mesylate), GLIADEL (carmustine implant), GLIADEL WAFER (carmustine implant), HERCEPTIN (trastuzumab), HYCAMTIN (topotecan hydrochloride), IFEX (ifosfamide), IFOSFAMIDUM (ifosfamide), INLYTA (axitinib), INTRON A (recombinant interferon alfa-2b), IRESSA (gefitinib), IXEMPRA (ixabepilone), JAKAFI (ruxolitinib phosphate), JEVTANA (cabazitaxel), KADCYLA (ado-trastuzumab emtansine), KEYTRUDA (pembrolizumab), KYPROLIS (carfilzomib), LIPODOX (doxorubicin hydrochloride liposome), LUPRON (leuprolide acetate), LUPRON DEPOT (leuprolide acetate), LUPRON DEPOT-3 MONTH (leuprolide acetate), LUPRON DEPOT-4 MONTH (leuprolide acetate), LUPRON DEPOT-PED (leuprolide acetate), MEGACE (megestrol acetate), MEKINIST (trametinib), METHAZOLASTONE (temozolomide), METHOTREXATE LPF (methotrexate), MEXATE (methotrexate), MEXATE-AQ (methotrexate), MITOXANTRONE HYDROCHLORIDE, MITOZYTREX (mitomycin c), MOZOBIL (plerixafor), MUSTARGEN (mechlorethamine hydrochloride), MUTAMYCIN (mitomycin c), MYLOSAR (azacitidine), NAVELBINE (vinorelbine tartrate), NEOSAR (cyclophosphamide), NEXAVAR (sorafenib tosylate), NOLVADEX (tamoxifen citrate), NOVALDEX (tamoxifen citrate), OFF, PAD, PARAPLAT (carboplatin), PARAPLATIN (carboplatin), PEG-INTRON (peginterferon alfa-2b), PEMETREXED DISODIUM, PERJETA (pertuzumab), PLATINOL (cisplatin), PLATINOL-AQ (cisplatin), POMALYST (pomalidomide), prednisone, PROLEUKIN (aldesleukin), PROLIA (denosumab), PROVENGE (sipuleucel-t), REVLIMID (lenalidomide), RUBIDOMYCIN (daunorubicin hydrochloride), SPRYCEL (dasatinib), STIVARGA (regorafenib), SUTENT (sunitinib malate), SYLATRON (peginterferon alfa-2b), SYLVANT (siltuximab), SYNOVIR (thalidomide), TAC, TAFINLAR (dabrafenib), TARABINE PFS (cytarabine), TARCEVA (erlotinib hydrochloride), TASIGNA (nilotinib), TAXOL (paclitaxel), TAXOTERE (docetaxel), TEMODAR (temozolomide), THALOMID (thalidomide), TOPOSAR (etoposide), TORISEL (temsirolimus), TPF, TRISENOX (arsenic trioxide), TYKERB (lapatinib ditosylate), VECTIBIX (panitumumab), VEIP, VELBAN (vinblastine sulfate), VELCADE (bortezomib), VELSAR (vinblastine sulfate), VEPESID (etoposide), VIADUR (leuprolide acetate), VIDAZA (azacitidine), VINCASAR PFS (vincristine sulfate), VOTRIENT (pazopanib hydrochloride), WELLCOVORIN (leucovorin calcium), XALKORI (crizotinib), XELODA (capecitabine), XELOX, XGEVA (denosumab), XOFIGO (radium 223 dichloride), XTANDI (enzalutamide), YERVOY (ipilimumab), ZALTRAP (ziv-aflibercept), ZELBORAF (vemurafenib), ZOLADEX (goserelin acetate), ZOMETA (zoledronic acid), ZYKADIA (ceritinib), ZYTIGA (abiraterone acetate), ENMD-2076, PCI-32765, AC220, dovitinib lactate (TKI258, CHIR-258), BIBW 2992 (TOVOK™), SGX523, PF-04217903, PF-02341066, PF-299804, BMS-777607, ABT-869, MP470, BIBF 1120 (VARGATEF®), AP24534, JNJ-26483327, MGCD265, DCC-2036, BMS-690154, CEP-11981, tivozanib (AV-951), OSI-930, MM-121, XL-184, XL-647, and/or XL228), proteasome inhibitors (e.g., bortezomib (Velcade)), mTOR inhibitors (e.g., rapamycin, temsirolimus (CCI-779), everolimus (RAD-001), ridaforolimus, AP23573 (Ariad), AZD8055 (AstraZeneca), BEZ235 (Novartis), BGT226 (Norvartis), XL765 (Sanofi Aventis), PF-4691502 (Pfizer), GDC0980 (Genetech), SF1126 (Semafoe) and OSI-027 (OSI)), oblimersen, gemcitabine, carminomycin, leucovorin, pemetrexed, cyclophosphamide, dacarbazine, procarbizine, prednisolone, dexamethasone, campathecin, plicamycin, asparaginase, aminopterin, methopterin, porfiromycin, melphalan, leurosidine, leurosine, chlorambucil, trabectedin, procarbazine, discodermolide, carminomycin, aminopterin, and hexamethyl melamine, or a combination thereof. In some embodiments, the additional agent is a protein kinase inhibitor (e.g., tyrosine protein kinase inhibitor). In some embodiments, the additional agent is selected from the group consisting of epigenetic or transcriptional modulators (e.g., DNA methyltransferase inhibitors, histone deacetylase inhibitors (HDAC inhibitors), lysine methyltransferase inhibitors), antimitotic drugs (e.g., taxanes and *vinca* alkaloids), hormone receptor modulators (e.g., estrogen receptor modulators and androgen receptor modulators), cell signaling pathway inhibitors (e.g., tyrosine protein kinase inhibitors), modulators of protein stability (e.g., proteasome inhibitors), Hsp90 inhibitors, glucocorticoids, all-trans retinoic acids, and other agents that promote differentiation.

In some embodiments, the composition or vaccine composition described herein are formulated for administration to a subject. In some embodiments, the composition or vaccine composition further comprises a pharmaceutically acceptable carrier. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. The phrase "pharmaceutically acceptable carrier" means a pharmaceutically acceptable material, composition or vehicle, such as a liquid or solid filler, diluent, excipient, solvent or encapsulating material, involved in carrying or transporting the subject agents from one organ, or portion of the body, to another organ, or portion of the body. Each carrier must be "acceptable" in the sense of being compatible with the other ingredients of the formulation and not injurious to the tissue of the patient (e.g., physiologically compatible, sterile, physiologic pH, etc.). The term "carrier" denotes an organic or inorganic ingredient, natural or synthetic, with which the active ingredient is combined to facilitate the application. The components of the composition or vaccine composition described herein also are capable of being co-mingled with the molecules of the present disclosure, and with each other, in a manner such that there is no interaction which would substantially impair the desired pharmaceutical efficacy. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) C2-C12 alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation.

The composition or vaccine composition described herein may conveniently be presented in unit dosage form and may be prepared by any of the methods well-known in the art of pharmacy. The term "unit dose" when used in reference to a composition or vaccine composition described herein of the present disclosure refers to physically discrete units suitable as unitary dosage for the subject, each unit containing a predetermined quantity of active material calculated to produce the desired therapeutic effect in association with the required diluent; i.e., carrier, or vehicle. Relative amounts of the active ingredient, the pharmaceutically acceptable excipient, and/or any additional ingredients in a pharmaceutical composition described herein will vary, depending upon the identity, size, and/or condition of the subject treated and further depending upon the route by which the composition is to be administered. The composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly (vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite (aluminum silicate) and Veegum (magnesium aluminum silicate)), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate (Tween® 20), polyoxyethylene sorbitan (Tween® 60), polyoxyethylene sorbitan monooleate (Tween® 80), sorbitan monopalmitate (Span® 40), sorbitan monostearate (Span® 60), sorbitan tristearate (Span® 65), glyceryl monooleate, sorbitan monooleate (Span® 80), polyoxyethylene esters (e.g., polyoxyethylene monostearate (Myrj® 45), polyoxyethylene hydrogenated castor oil, polyethoxylated castor oil, polyoxymethylene stearate, and Solutol®), sucrose fatty acid esters, polyethylene glycol fatty acid esters (e.g., Cremophor®), polyoxyethylene ethers, (e.g., polyoxyethylene lauryl ether (Brij® 30)), poly (vinyl-pyrrolidone), diethylene glycol monolaurate, triethanolamine oleate, sodium oleate, potassium oleate, ethyl oleate, oleic acid, ethyl laurate, sodium lauryl sulfate, Pluronic® F-68, poloxamer P-188, cetrimonium bromide, cetylpyridinium chloride, benzalkonium chloride, docusate sodium, and/or mixtures thereof.

Exemplary binding agents include starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum®), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, antiprotozoan preservatives, alcohol preservatives, acidic preservatives, and other preservatives. In certain embodiments, the preservative is an antioxidant. In other embodiments, the preservative is a chelating agent.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant® Plus, Phenonip®, methylparaben, Germall® 115, Germaben® II, Neolone®, Kathon®, and Euxyl®.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, *eucalyptus*, evening primrose, fish, flaxseed, geraniol, gourd, grape seed, hazel nut, hyssop, isopropyl myristate, jojoba, kukui nut, lavandin, lavender, lemon, *Litsea cubeba*, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates described herein are mixed with solubilizing agents such as Cremophor®, alcohols, oils, modified oils, glycols, polysorbates, cyclodextrins, polymers, and mixtures thereof. The formulation of the composition or vaccine composition described herein may dependent upon the route of administration. Injectable preparations suitable for parenteral administration or intratumoral, peritumoral, intralesional or perilesional administration include, for example, sterile injectable aqueous or oleaginous suspensions and may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3 propanediol or 1,3 butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid find use in the preparation of injectables. The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use. Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may include a buffering agent.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the art of pharmacology. They may optionally comprise opacifying agents and can be of a composition that they release the active ingredient(s) only, or preferentially, in a certain part of the intestinal tract, optionally, in a delayed manner. Examples of encapsulating compositions which can be used include polymeric substances and waxes. Solid compositions of a similar type can be employed as fillers in soft and hard-filled gelatin capsules using such excipients as lactose or milk sugar as well as high molecular weight polethylene glycols and the like.

The active ingredient can be in a micro-encapsulated form with one or more excipients as noted above. The solid dosage forms of tablets, dragees, capsules, pills, and granules can be prepared with coatings and shells such as enteric coatings, release controlling coatings, and other coatings well known in the pharmaceutical formulating art. In such solid dosage forms the active ingredient can be admixed with at least one inert diluent such as sucrose, lactose, or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of encapsulating agents which can be used include polymeric substances and waxes.

Suitable devices for use in delivering intradermal pharmaceutical compositions described herein include short needle devices. Intradermal compositions can be administered by devices which limit the effective penetration length of a needle into the skin. Alternatively or additionally, conventional syringes can be used in the classical mantoux method of intradermal administration. Jet injection devices which deliver liquid formulations to the dermis via a liquid jet injector and/or via a needle which pierces the stratum corneum and produces a jet which reaches the dermis are suitable. Ballistic powder/particle delivery devices which use compressed gas to accelerate the compound in powder form through the outer layers of the skin to the dermis are suitable.

For topical administration, the composition or vaccine composition described herein can be formulated into ointments, salves, gels, or creams, as is generally known in the art. Topical administration can utilize transdermal delivery systems well known in the art. An example is a dermal patch.

Compositions suitable for oral administration may be presented as discrete units, such as capsules, tablets, lozenges, each containing a predetermined amount of the anti-inflammatory agent. Other compositions include suspensions in aqueous liquids or non-aqueous liquids such as a syrup, elixir or an emulsion.

Other delivery systems can include time-release, delayed release or sustained release delivery systems. Such systems can avoid repeated administrations of the anti-inflammatory agent, increasing convenience to the subject and the physician. Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. U.S. Pat. No. 5,075,109. Delivery systems also include non-polymer systems that are: lipids including sterols such as cholesterol, cholesterol esters and fatty acids or neutral fats such as mono-di- and triglycerides; hydrogel release systems; sylastic systems; peptide based systems; wax coatings; compressed tablets using conventional binders and excipients; partially fused implants; and the like. Specific examples include, but are not limited to: (a) erosional systems in which the anti-inflammatory agent is contained in a form within a matrix such as those described in U.S. Pat. Nos. 4,452,775, 4,667,014, 4,748,034 and 5,239,660 and (b) diffusional systems in which an active component permeates at a controlled rate from a polymer such as described in U.S. Pat. Nos. 3,832, 253, and 3,854,480. In addition, pump-based hardware delivery systems can be used, some of which are adapted for implantation.

Use of a long-term sustained release implant may be particularly suitable for treatment of chronic conditions. Long-term release, are used herein, means that the implant is constructed and arranged to delivery therapeutic levels of the active ingredient for at least 30 days, and preferably 60 days. Long-term sustained release implants are well-known to those of ordinary skill in the art and include some of the release systems described above.

In some embodiments, the composition or vaccine composition described herein used for therapeutic administration must be sterile. Sterility is readily accomplished by filtration through sterile filtration membranes (e.g., 0.2 micron membranes). Alternatively, preservatives can be used to prevent the growth or action of microorganisms. Various preservatives are well known and include, for example, phenol and ascorbic acid. The cyclic Psap peptide and/or the composition or vaccine composition described herein ordinarily will be stored in lyophilized form or as an aqueous solution if it is highly stable to thermal and oxidative denaturation. The pH of the preparations typically will be about from 6 to 8, although higher or lower pH values can also be appropriate in certain instances. The chimeric constructs of the present disclosure can be used as vaccines by conjugating to soluble immunogenic carrier molecules. Suitable carrier molecules include protein, including keyhole limpet hemocyanin, which is a preferred carrier protein. The chimeric construct can be conjugated to the carrier molecule using standard methods. (Hancock et al., "Synthesis of Peptides for Use as Immunogens," in Methods in Molecular Biology: Immunochemical Protocols, Manson (ed.), pages 23-32 (Humana Press 1992)).

In some embodiments, the present disclosure contemplates a vaccine composition comprising a pharmaceutically acceptable injectable vehicle. The vaccines of the present disclosure may be administered in conventional vehicles with or without other standard carriers, in the form of injectable solutions or suspensions. The added carriers might be selected from agents that elevate total immune response in the course of the immunization procedure.

Liposomes have been suggested as suitable carriers. The insoluble salts of aluminum, that is aluminum phosphate or aluminum hydroxide, have been utilized as carriers in routine clinical applications in humans. Polynucleotides and polyelectrolytes and water soluble carriers such as muramyl dipeptides have been used.

Preparation of injectable vaccines of the present disclosure, includes mixing the antigen and/or the TLR2 agonists with muramyl dipeptides or other carriers. The resultant mixture may be emulsified in a mannide monooleate/squalene or squalane vehicle. Four parts by volume of squalene and/or squalane are used per part by volume of mannide monooleate. Methods of formulating vaccine compositions are well-known to those of ordinary skill in the art. (Rola, Immunizing Agents and Diagnostic Skin Antigens. In: Remington's Pharmaceutical Sciences, 18th Edition, Gennaro (ed.), (Mack Publishing Company 1990) pages 1389-1404).

Additional pharmaceutical carriers may be employed to control the duration of action of a vaccine in a therapeutic application. Control release preparations can be prepared through the use of polymers to complex or adsorb chimeric construct. For example, biocompatible polymers include matrices of poly(ethylene-co-vinyl acetate) and matrices of a polyanhydride copolymer of a stearic acid dimer and sebacic acid. (Sherwood et al. (1992) Bio/Technology 10:1446). The rate of release of the chimeric construct from such a matrix depends upon the molecular weight of the construct, the amount of the construct within the matrix, and the size of dispersed particles. (Saltzman et al. (1989) Biophys. J. 55:163; Sherwood et al, supra.; Ansel et al. Pharmaceutical Dosage Forms and Drug Delivery Systems, 5th Edition (Lea & Febiger 1990); and Gennaro (ed.), Remington's Pharmaceutical Sciences, 18th Edition (Mack Publishing Company 1990)). The chimeric construct can also be conjugated to polyethylene glycol (PEG) to improve stability and extend bioavailability times (e.g., Katre et al.; U.S. Pat. No. 4,766,106).

Also encompassed by the disclosure are kits (e.g., pharmaceutical packs). The kits provided may comprise a pharmaceutical composition or compound described herein and a container (e.g., a vial, ampule, bottle, syringe, and/or dispenser package, or other suitable container). In some embodiments, provided kits may optionally further include a second container comprising a pharmaceutical excipient for dilution or suspension of a pharmaceutical composition or compound described herein. In some embodiments, the pharmaceutical composition or compound described herein provided in the first container and the second container are combined to form one unit dosage form.

Thus, in one aspect, provided are kits including a first container comprising a compound or pharmaceutical composition described herein. In certain embodiments, the kits are useful for treating a disease (e.g., proliferative disease, inflammatory disease, autoimmune disease, infectious disease, or chronic disease) in a subject in need thereof. In certain embodiments, the kits are useful for preventing a disease (e.g., proliferative disease, inflammatory disease, autoimmune disease, infectious disease, or chronic disease) in a subject in need thereof. In certain embodiments, the kits are useful as enhancers of an immune response (e.g., innate and/or adaptive immune response), and/or adjuvants in a vaccine for a disease, (e.g., proliferative disease, inflammatory disease, autoimmune disease, infectious disease, or chronic disease) in a subject, biological sample, tissue, or cell.

In certain embodiments, a kit described herein further includes instructions for using the compound or pharmaceutical composition included in the kit. A kit described herein may also include information as required by a regulatory agency such as the U.S. Food and Drug Administration (FDA). In certain embodiments, the information included in the kits is prescribing information. In certain embodiments, the kits and instructions provide for treating a disease (e.g., proliferative disease, inflammatory disease, autoimmune disease, infectious disease, or chronic disease) in a subject in need thereof. In certain embodiments, the kits and instructions provide for preventing a disease (e.g., proliferative disease, inflammatory disease, autoimmune disease, infectious disease, or chronic disease) in a subject in need thereof. In certain embodiments, the kits and instructions provide for enhancing of an immune response (e.g., innate and/or adaptive immune response) in a subject, biological sample, tissue, or cell. In certain embodiments, the kits and instructions provide for use of the compounds as adjuvants in a vaccine for a disease, (e.g., proliferative disease, inflammatory disease, autoimmune disease, infectious disease, or chronic disease) in a subject, biological sample, tissue, or cell. A kit described herein may include one or more additional pharmaceutical agents described herein as a separate composition.

The terms "treatment," "treat," and "treating" refer to reversing, alleviating, delaying the onset of, or inhibiting the progress of a disease described herein. In some embodiments, treatment may be administered after one or more signs or symptoms of the disease have developed or have been observed. In other embodiments, treatment may be administered in the absence of signs or symptoms of the disease. For example, treatment may be administered to a susceptible subject prior to the onset of symptoms (e.g., in light of a history of symptoms and/or in light of exposure to a pathogen). Treatment may also be continued after symptoms have resolved, for example, to delay or prevent recurrence. Prophylactic treatment refers to the treatment of a subject who is not and was not with a disease but is at risk of developing the disease or who was with a disease, is not with the disease, but is at risk of regression of the disease. In some embodiments, the subject is at a higher risk of developing the disease or at a higher risk of regression of the disease than an average healthy member of a population.

An "effective amount" of a composition described herein refers to an amount sufficient to elicit the desired biological response. An effective amount of a composition described herein may vary depending on such factors as the desired biological endpoint, the pharmacokinetics of the compound, the condition being treated, the mode of administration, and the age and health of the subject. In some embodiments, an effective amount is a therapeutically effective amount. In some embodiments, an effective amount is a prophylactic treatment. In some embodiments, an effective amount is the amount of a compound described herein in a single dose. In some embodiments, an effective amount is the combined amounts of a compound described herein in multiple doses. When an effective amount of a composition is referred herein, it means the amount is prophylactically and/or therapeutically effective, depending on the subject and/or the disease to be treated. Determining the effective amount or dosage is within the abilities of one skilled in the art.

The terms "administer," "administering," or "administration" refers to implanting, absorbing, ingesting, injecting, inhaling, or otherwise introducing a compound described herein, or a composition thereof, in or on a subject. The composition of the vaccine composition described herein may be administered systemically (e.g., via intravenous injection) or locally (e.g., via local injection). In some embodiments, the composition of the vaccine composition described herein is administered orally, intravenously, topically, intranasally, or sublingually. Parenteral administerating is also contemplated. The term "parenteral" as used herein includes subcutaneous, intracutaneous, intravenous, intramuscular, intraarticular, intraarterial, intrasynovial, intrasternal, intrathecal, intralesional, intradermally, and intracranial injection or infusion techniques. In some embodiments, the administering is done intramuscularly, intradermally, orally, intravenously, topically, intranasally, intravaginally, or sublingually. In some embodiments, the composition is administered prophylactically.

In some embodiments, the composition or vaccine composition is administered once or administered repeatedly (e.g., 2, 3, 4, 5, or more times). For multiple administrations, the administrations may be done over a period of time (e.g., 6 months, a year, 2 years, 5 years, 10 years, or longer). In some embodiments, the composition or vaccine composition is administered twice (e.g., Day 0 and Day 7, Day 0 and Day 14, Day 0 and Day 21, Day 0 and Day 28, Day 0 and Day 60, Day 0 and Day 90, Day 0 and Day 120, Day 0 and Day 150, Day 0 and Day 180, Day 0 and 3 months later, Day 0 and 6 months later, Day 0 and 9 months later, Day 0 and 12 months later, Day 0 and 18 months later, Day 0 and 2 years later, Day 0 and 5 years later, or Day 0 and 10 years later).

A "subject" to which administration is contemplated refers to a human (i.e., male or female of any age group, e.g., pediatric subject (e.g., infant, child, or adolescent) or adult subject (e.g., young adult, middle-aged adult, or senior adult)) or non-human animal. In some embodiments, the non-human animal is a mammal (e.g., primate (e.g., cynomolgus monkey or rhesus monkey), commercially relevant mammal (e.g., cattle, pig, horse, sheep, goat, cat, or dog), or bird (e.g., commercially relevant bird, such as chicken, duck, goose, or turkey)). In some embodiments, the non-human animal is a fish, reptile, or amphibian. The non-human animal may be a male or female at any stage of development. The non-human animal may be a transgenic animal or genetically engineered animal. A "subject in need thereof" refers to a human subject in need of treatment of a disease or in need of reducing the risk of developing a disease. In some embodiments, the subject has any of the diseases described herein (e.g., infectious disease, cancer, or allergy). In some embodiments, the subject is at risk of developing any of the diseases described herein (e.g., infectious disease, cancer, or allergy). In some embodiments, administering the antigen and the TLR2 agonist (e.g., thiophene compound) described herein to a subject having a disease treats the disease (therapeutic use). In some embodiments, administering the antigen and the TLR2 agonist (e.g., thiophene compound) described herein to a subject at risk of developing a disease reduces the likelihood (e.g., by 20%, 30%, 40%, 50%, 60%, 70%, 80%, 90%, 95%, 99% or more) of the subject developing the disease (prophylactic use).

In some aspects, the present disclosure contemplates the vaccination of human infants or neonates. In some embodiments, the subject is a human infant. In some embodiments, the human infant is a neonate that is less than 28 days of age. In some embodiments, the human infant is 0-28 days, 0-27 days, 0-26 days, 0-25 days, 0-24 days, 0-23 days, 0-22 days, 0-21 days, 0-20 days, 0-19 days, 0-18 days, 0-17 days, 0-16 days, 0-15 days, 0-14 days, 0-13 days, 0-12 days, 0-11 days, 0-10 days, 0-9 days, 0-8 days, 0-7 days, 0-6 days, 0-5 days, 0-4 days, 0-3 days, 0-2 days, 0-1 days, 0-12 hours, 0-6 hours, 0-2 hours, 0-1 hour, 1-28 days, 1-27 days, 1-26 days, 1-25 days, 1-24 days, 1-23 days, 1-22 days, 1-21 days, 1-20 days, 1-19 days, 1-18 days, 1-17 days, 1-16 days, 1-15 days, 1-14 days, 1-13 days, 1-12 days, 1-11 days, 1-10 days, 1-9 days, 1-8 days, 1-7 days, 1-6 days, 1-5 days, 1-4 days, 1-3 days, 1-2 days, 2-28 days, 2-27 days, 2-26 days, 2-25 days, 2-24 days, 2-23 days, 2-22 days, 2-21 days, 2-20 days, 2-19 days, 2-18 days, 2-17 days, 2-16 days, 2-15 days, 2-14 days, 2-13 days, 2-12 days, 2-11 days, 2-10 days, 2-9 days, 2-8 days, 2-7 days, 2-6 days, 2-5 days, 2-4 days, 2-3 days, 3-28 days, 3-27 days, 3-26 days, 3-25 days, 3-24 days, 3-23 days, 3-22 days, 3-21 days, 3-20 days, 3-19 days, 3-18 days, 3-17 days, 3-16 days, 3-15 days, 3-14 days, 3-13 days, 3-12 days, 3-11 days, 3-10 days, 3-9 days, 3-8 days, 3-7 days, 3-6 days, 3-5 days, 3-4 days, 4-28 days, 4-27 days, 4-26 days, 4-25 days, 4-24 days, 4-23 days, 4-22 days, 4-21 days, 4-20 days, 4-19 days, 4-18 days, 4-17 days, 4-16 days, 4-15 days, 4-14 days, 4-13 days, 4-12 days, 4-11 days, 4-10 days, 4-9 days, 4-8 days, 4-7 days, 4-6 days, 4-5 days, 5-28 days, 5-27 days, 5-26 days, 5-25 days, 5-24 days, 5-23 days, 5-22 days, 5-21 days, 5-20 days, 5-19 days, 5-18 days, 5-17 days, 5-16 days, 5-15 days, 5-14 days, 5-13 days, 5-12 days, 5-11 days, 5-10 days, 5-9 days, 5-8 days, 5-7 days, 5-6 days, 6-28 days, 6-27 days, 6-26 days, 6-25 days, 6-24 days, 6-23 days, 6-22 days, 6-21 days, 6-20 days, 6-19 days, 6-18 days, 6-17 days, 6-16 days, 6-15 days, 6-14 days, 6-13 days, 6-12 days, 6-11 days, 6-10 days, 6-9 days, 6-8 days, 6-7 days, 7-28 days, 7-27 days, 7-26 days, 7-25 days, 7-24 days, 7-23 days, 7-22 days, 7-21 days, 7-20 days, 7-19 days, 7-18 days, 7-17 days, 7-16 days, 7-15 days, 7-14 days, 7-13 days, 7-12 days, 7-11 days, 7-10 days, 7-9 days, 7-8 days, 9-28 days, 9-27 days, 9-26 days, 9-25 days, 9-24 days, 9-23 days, 9-22 days, 9-21 days, 9-20 days, 9-19 days, 9-18 days, 9-17 days, 9-16 days, 9-15 days, 9-14 days, 9-13 days, 9-12 days, 9-11 days, 9-10 days, 10-28 days, 10-27 days, 10-26 days, 10-25 days, 10-24 days, 10-23 days, 10-22 days, 10-21 days, 10-20 days, 10-19 days, 10-18 days, 10-17 days, 10-16 days, 10-15 days, 10-14 days, 10-13 days, 10-12 days, 10-11 days, 11-28 days, 11-27 days, 11-26 days, 11-25 days, 11-24 days, 11-23 days, 11-22 days, 11-21 days, 11-20 days, 11-19 days, 11-18 days, 11-17 days, 11-16 days, 11-15 days, 11-14 days, 11-13 days, 11-12 days, 12-28 days, 12-27 days, 12-26 days, 12-25 days, 12-24 days, 12-23 days, 12-22 days, 12-21 days, 12-20 days, 12-19 days, 12-18 days, 12-17 days, 12-16 days, 12-15 days, 12-14 days, 12-13 days, 13-28 days, 13-27 days, 13-26 days, 13-25 days, 13-24 days, 13-23 days, 13-22 days, 13-21 days, 13-20 days, 13-19 days, 13-18 days, 13-17 days, 13-16 days, 13-15 days, 13-14 days, 14-28 days, 14-27 days, 14-26 days, 14-25 days, 14-24 days, 14-23 days, 14-22 days, 14-21 days, 14-20 days, 14-19 days, 14-18 days, 14-17 days, 14-16 days, 14-15 days, 15-28 days, 15-27 days, 15-26 days, 15-25 days, 15-24 days, 15-23 days, 15-22 days, 15-21 days, 15-20 days, 15-19 days, 15-18 days, 15-17 days, 15-16 days, 16-28 days, 16-27 days, 16-26 days, 16-25 days, 16-24 days, 16-23 days, 16-22 days, 16-21 days, 16-20 days, 16-19 days, 16-18 days, 16-17 days, 17-28 days, 17-27 days, 17-26 days, 17-25 days, 17-24 days, 17-23 days, 17-22 days, 17-21 days, 17-20 days, 17-19 days, 17-18 days, 18-28 days, 18-27 days, 18-26 days, 18-25 days, 18-24 days, 18-23 days, 18-22 days, 18-21 days, 18-20 days, 18-19 days, 19-28 days, 19-27 days, 19-26 days, 19-25 days, 19-24 days, 19-23 days, 19-22 days, 19-21 days, 19-20 days, 20-28 days, 20-27 days, 20-26 days, 20-25 days, 20-24 days, 20-23 days, 20-22 days, 20-21 days, 21-28 days, 21-27 days, 21-26 days, 21-25 days, 21-24 days, 21-23 days, 21-22 days, 22-28 days, 22-27 days, 22-26 days, 22-25 days, 22-24 days, 22-23 days, 23-28 days, 23-27 days, 23-26 days, 23-25 days, 23-24 days, 24-28 days, 24-27 days, 24-26 days, 24-25 days, 25-28 days, 25-27 days, 25-26 days, 26-28 days, 26-27 days, or 27-28 days of age at the time of administration of the vaccine composition described herein. In some embodiments, the human neonate is 1, 2, 3, 4, 5,6, 7, 8, 9, 10, 11, 12, 13, 14, 15, 16, 17, 18, 19, 20, 21, 22, 23, 24, 25, 26, 27, or 28 days of age at the time of administration of the vaccine composition described herein.

In some embodiments, the human infant is less than 28 days of age at the time of administration (vaccination). In some embodiments, the human infant is less than 4 days of age at the time of administration (vaccination). In some embodiments, the human infant is less than 2 days of age at the time of administration (vaccination). In some embodiments, the human infant is less than 24 days of age at the time of administration (vaccination). In some embodiments, the administration (vaccination) occurs at birth. In some embodiments, a human neonate (less than 28 days of age) receives 1 or 2 doses of the vaccine described herein. In some embodiments, the human neonate receives one dose before 28-days of age (e.g., 2, 3, 4, 5, 6, 7, 8, 9, 10, 11, 12, 13, 14, 15, 16, 17, 18, 19, 20 days of age) and a second dose before or at 28-days of age. In some embodiments, the human subject receives one dose at 2 months, 4 months, or 6 months of age, and a second dose after the first dose at 2 months, 4 months, or 6 months of age. In some embodiments, a human subject receives a second dose before or equal to 6-months of age (e.g., 1, 2, 3, 4, 5, 6 months of age). In some embodiments, the administration occurs when the human infant is 2 months, 4 months, and 6 months of age. In some embodiments, a human subject receives a second dose after 6-months of age (e.g., 1 year, 2 years, 3 years of age).

In some embodiments, the human subject is more than 28-days old (e.g., 1 month, 2 months, 3 months, 4 months, 5 months, 6 months, 7 months, 8 months, 9 months, 10 months, 11 months, 12 months, 2 years, 3 years, 4 years, 5 years, 10 years, 11 years, 12 years, 13 years, 14 years, 15 years, 16 years, 17 years old). In some embodiments, the human subject is an adult (e.g., more than 18 years old). In some embodiments, the human subject is an elderly (e.g., more than 60 years old). In some embodiments, the human subject is more than 65-years of age. In some embodiments, the human subject receives one or two doses of the vaccine described herein after 65-years of age.

In some embodiments, the human subject is born prematurely or has low birth weight. "Born prematurely" means the human subject is born before 40-weeks of term. In some embodiments, the human subject is born before 37-weeks of term. In some embodiments, the human subject is born before 32 weeks of term. In some embodiments, the human subject is born before 24 weeks of term. In some embodiments, the human subject is born before 40 weeks, 39 weeks, 38 weeks, 37 weeks, 36 weeks, 35 weeks, 34 weeks, 33 weeks, 32 weeks, 31 weeks, 30 weeks, 29 weeks, 28 weeks, 27 weeks, 26 weeks, 25 weeks, or 24 weeks of term. In some embodiments, the human subject is born with low birth weight (e.g., at least 20% lower than a normal birth weight).

In some embodiments, the human subject has an undeveloped (e.g., an infant or a neonate), weak (an elderly), or compromised immune system. Immunocompromised subjects include, without limitation, subjects with primary immunodeficiency or acquired immunodeficiency such as those suffering from sepsis, HIV infection, and cancers, including those undergoing chemotherapy and/or radiotherapy.

In some embodiments, the subject is a companion animal (a pet). The use of the TLR2 agonist (e.g., thiophene compound) described herein in veterinary vaccine is also within the scope of the present disclosure. "A companion animal," as used herein, refers to pets and other domestic animals. Non-limiting examples of companion animals include dogs and cats; livestock such as horses, cattle, pigs, sheep, goats, and chickens; and other animals such as mice, rats, guinea pigs, and hamsters. In some embodiments, the subject is a research animal. Non-limiting examples of research animals include: rodents (e.g., rats, mice, guinea pigs, and hamsters), rabbits, or non-human primates.

Some of the embodiments, advantages, features, and uses of the technology disclosed herein will be more fully understood from the Examples below. The Examples are intended to illustrate some of the benefits of the present disclosure and to describe particular embodiments, but are not intended to exemplify the full scope of the disclosure and, accordingly, do not limit the scope of the disclosure.

EXAMPLES

Example 1. Immunomodulatory Activity of TLR2 Agonists

Described herein is a novel molecular approach to shape human immune responses using formulations of small molecules, identified based on induction of unique cellular phenotype (i.e., adhesion), to act as adjuvants in vivo.

Human immunity is crucial to both health and illness, playing key roles in multiple major diseases including infectious diseases, allergy and cancer. In this context there is growing interest in development of approaches to modulate the human immune system to prevent and/or treat illness. Infectious diseases are the leading cause of morbidity and mortality in early life. Immunization is a key strategy for preventing infectious diseases, but immunization of newborns and infants may result in sub-optimal responses, often requires multiple booster doses and can be limited by waning immunity. Adjuvantation is a key approach to enhance vaccine-induced immunity. Adjuvants can enhance, prolong, and modulate immune responses to vaccinal antigens to maximize protective immunity, and may potentially enable effective immunization in vulnerable populations (e.g., in the very young and the elderly or for diseases lacking effective vaccines).

HTS Overview: To identify immunomodulators/adjuvants that robustly activate human immune cells, ~200,000 small molecules were screening in a THP1 cell-based assay. The chemical libraries screened included known bioactive and commercial libraries from various sources including commercial libraries such as ChemDiv, ChemBridge, and Asinex. All libraries were owned and provided by the Institute of Chemistry and Cell Biology (ICCB)—Longwood (Harvard Medical School). The project primary screen incorporated two distinct arms: a) a luciferase-based screen which corresponds to the relative activation of the NF-κB reporter; and b) a fluorescence-based screen, corresponding to the phenotypic adherence, a distinct marker of cell activation, of the human monocytic THP-1 cell lines. Described herein are small molecules identified in the screen that induce NF-kB activity based on a luciferase-based THP-1 cell screen.

Figure 1B:
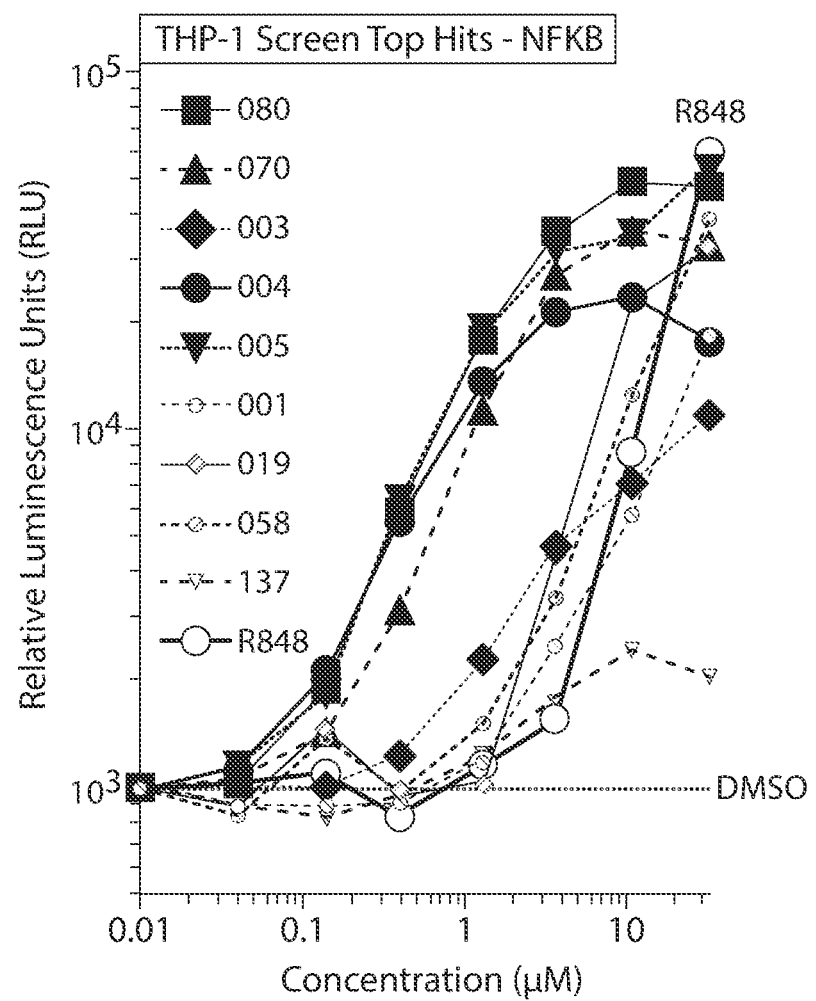

Overall, ~200,000 compounds were evaluated employing a luciferase-based screen and a phenotypic screen for adherence of human NF-κB Reporter THP-1 monocytic cell line in a 384 well format (Table 1). Further a confirmation screen based on the ~1,300 compounds identified was completed, using a high throughput CyBio CyBi-Well Vario, which works via a "Pocket Tip Transfer" methodology. As shown in Table 2, a final total of 167 compounds have confirmed, representing a final confirmation hit rate of ~13%. Based on a screen for luminescence of a stimulated human THP-1 monocytic cell line in a 384-well format, a novel adjuvant scaffolds, a thienopyridine named "080" (molecular weight 408 Da) and "004" (molecular weight 394 Da) were identified, which were the most effective NF-κB activators in THP1 cells (FIGS. 1A-1B).

TABLE 1

Overview of the full HTS for NF-kB and Adherence

| Hit Type | Readout | Hit # | Hit % |
|---|---|---|---|
| Type 1 | Luminescence only | 884 | 0.446 |
| Type 2 | Luminescence & Fluorescence | 139 | 0.070 |
| Type 3 | Fluorescence only | 285 | 0.144 |
| Combined | Combined | 1308 | 0.659 |

A total of ~200,000 compounds were evaluated employing a luciferase-based screen and a phenotypic screen for adherence of human NF-KB Reporter THP-1 monocytic cell line in a 384 well format.
~1300 lead compounds were identified, a combined hit rate of ~0.65%, for further for confirmation/titration screening.
Type 1: Luminescence (NF-kB activation);
Type 2: Luminescence (NF-kB activation) & Fluorescence (Adherence);
Type 3: Fluorescence (Adherence).

TABLE 2

Overview of the confirmed hits for NF-kB and adherence

| Hit Type | Readout | Hit # | Hit % |
|---|---|---|---|
| Type 1 | Luminescence only | 105 | 11.88 |
| Type 2 | Luminescence & Fluorescence | 24 | 17.27 |
| Type 3 | Fluorescence only | 38 | 13.33 |
| Combined | Combined | 167 | 12.77 |

A total of ~1,308 compounds were re-evaluated employing a luciferase-based screen and a phenotypic screen for adherence of human NF-KB Reporter THP-1 monocytic cell line in a 384 well format.
~167 lead compounds were confimred, a combined hit rate of ~0.65%, for further for confirmation/titration screening.
Type 1: Luminescence (NF-kb activation);
Type 2: Luminescence (NF-kB activation) & Fluorescence (Adherence);
Type 3: Fluorescence (Adherence).

Figure 3:
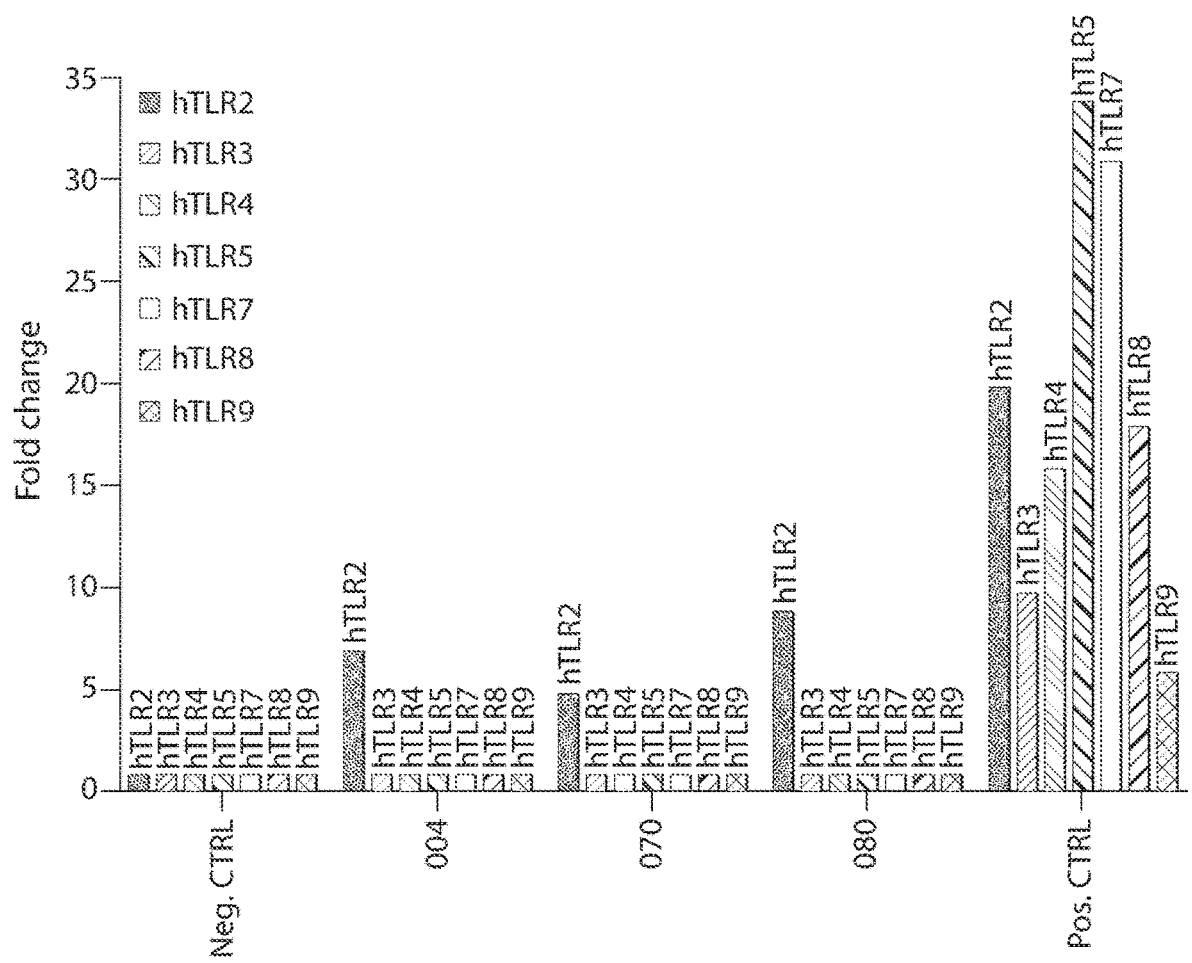
FIG. 3. Compounds 004, 007, and 080 activate human TLR2. Human TLR-expressing human embryonic kidney (HEK)-Blue cell lines were employed to monitor the activation of NF-κB upon stimulation with compounds 004, 070, 080 at 10 μM as well as positive controls (Pos. CTRL). Results for each cell line are shown as fold change over negative controls (Neg. CTRL) and represent the mean of 3 independent experiments.
Figure 4A:
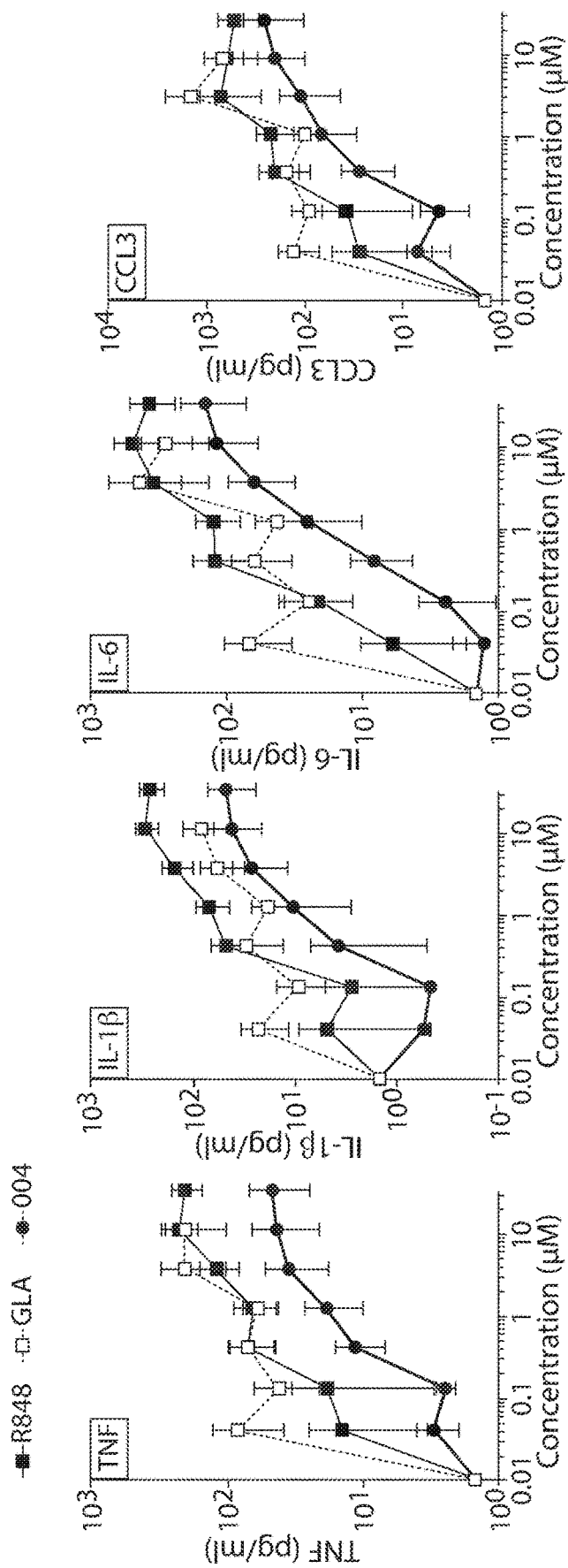
FIGS. 4A-4C. Compound 004 activates human adult PBMCs in a concentration-dependent manner. Human adult PBMCs were stimulated in 384-well plates for 24 hours with compound 004, glycopyranosyl lipid A (GLA; TLR4 agonist) and R848 (TLR7/8 agonist) at a concentration range of 0.05-33 μM. Cytokine levels were assessed in cell-free supernatants by multiplex assay.
Figure 4B:
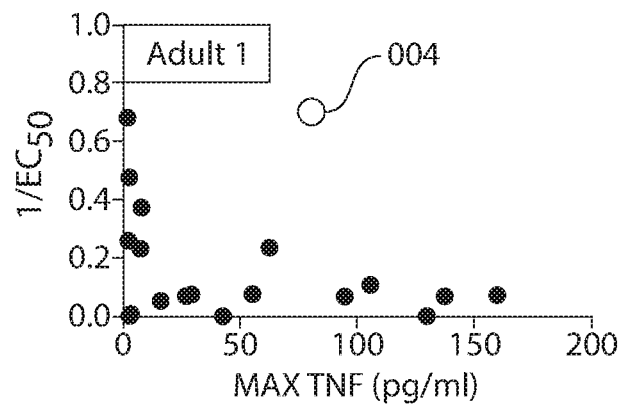
Figure 4C:
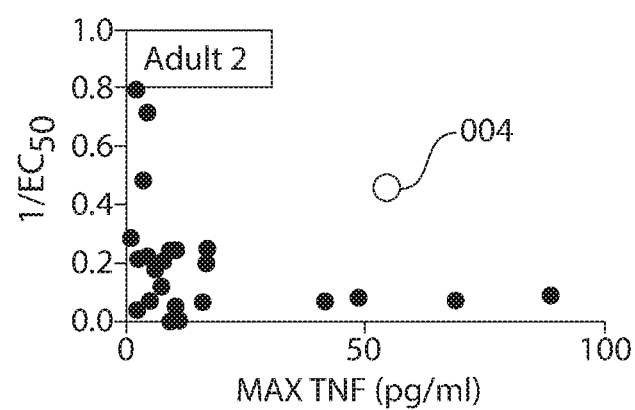
Figure 5:
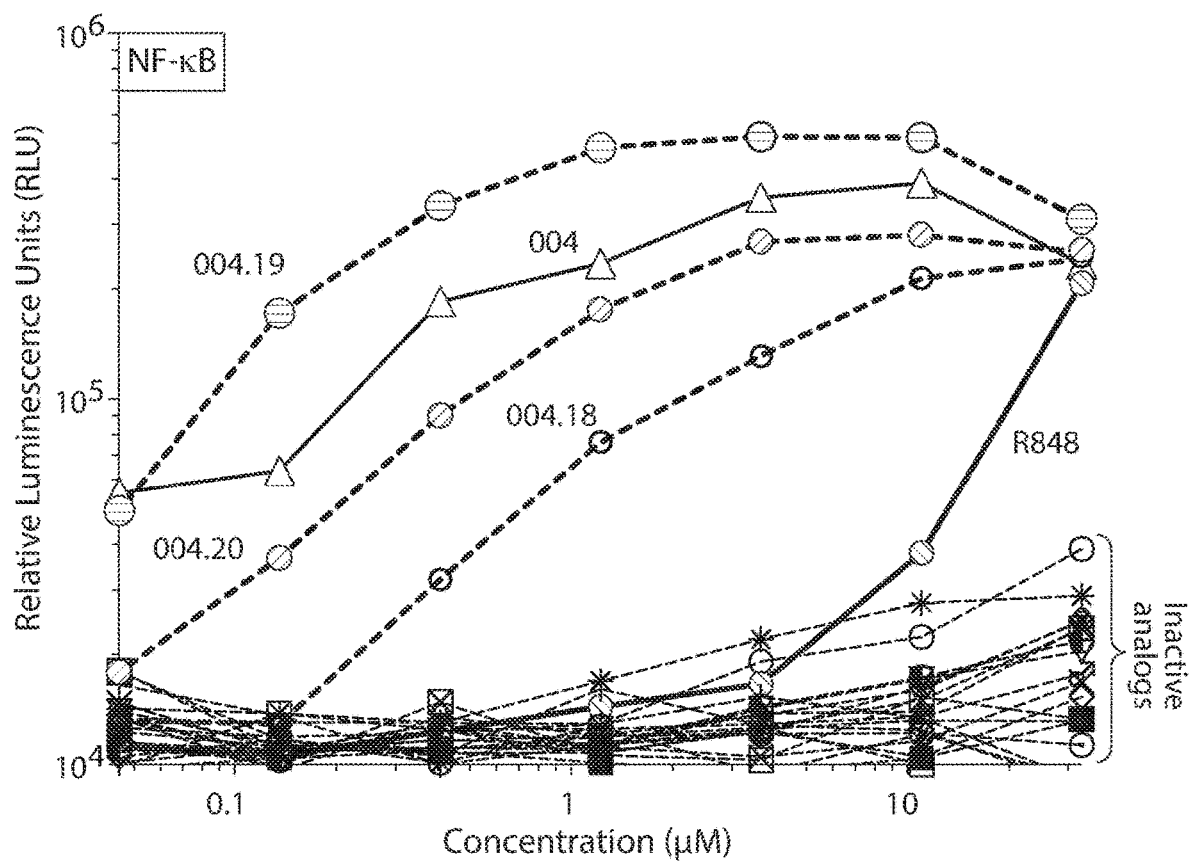
FIG. 5. Compound 004 analog activities on THP1-NF-κB cells. THP1-NF-κB cells were stimulated with compound 004, its analogs and the positive control R484 (concentration range 0.05-33 μM). NF-κB activation was measured by quantifying the luminescence from the secreted luciferase enzyme in cell-free supernatants. Compound 004 is depicted with triangles, R848 is depicted with a solid line and circles, inactive analogs are depicted in black and analogs with efficacy and potency comparable to or greater than compound 004 are depicted with thick dashed lines.
Figure 6:
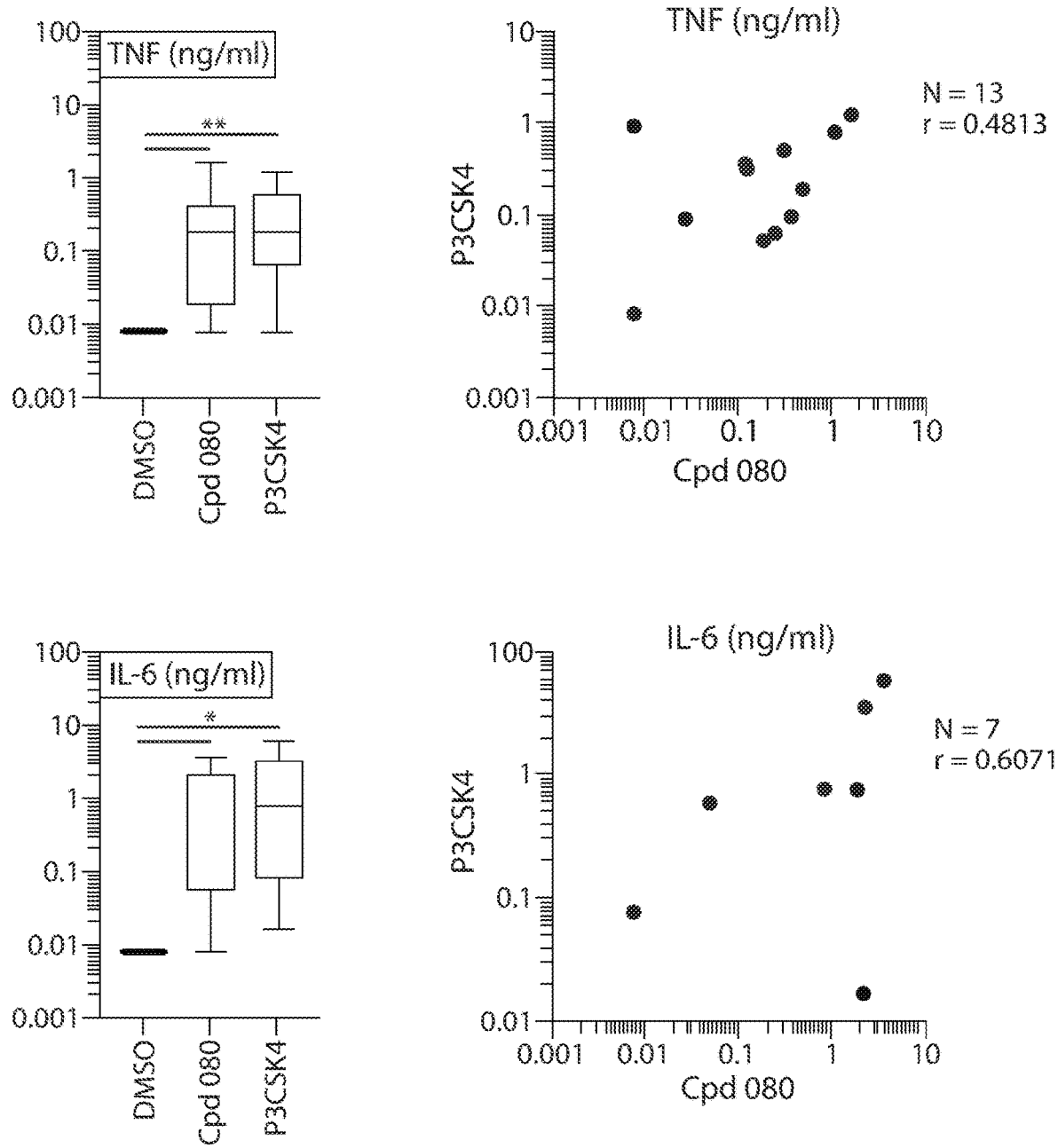
FIG. 6. Compound 080 induces cytokine production from human adult PBMCs. Human adult PBMCs were stimulate for 24 hours with compound 080 (100 μM) and the TLR2 agonist P3CSK4 (1 μg/ml). TNF and IL-6 levels were assessed in cell-free supernatants by ELISA and the results are shown in left panels show as the median, the 25th and 75th percentiles (boxes) and the 5th and 95th percentiles (whiskers) of TNF (N=13) and IL-6 (N=7). Right panels show the correlations between cytokine production elicited by compound 080 and the commercially available TLR2 agonist bacterial lipopeptide Pam3CysK4 (P3CSK4; InvivoGen; San Diego, CA). Each dot represents a single donor (N=13 for TNF and N=7 for IL-6). *$p<0.05$ and **$p<0.01$ determined by Friedman test with Dunn's multiple comparison test.
Figure 7:
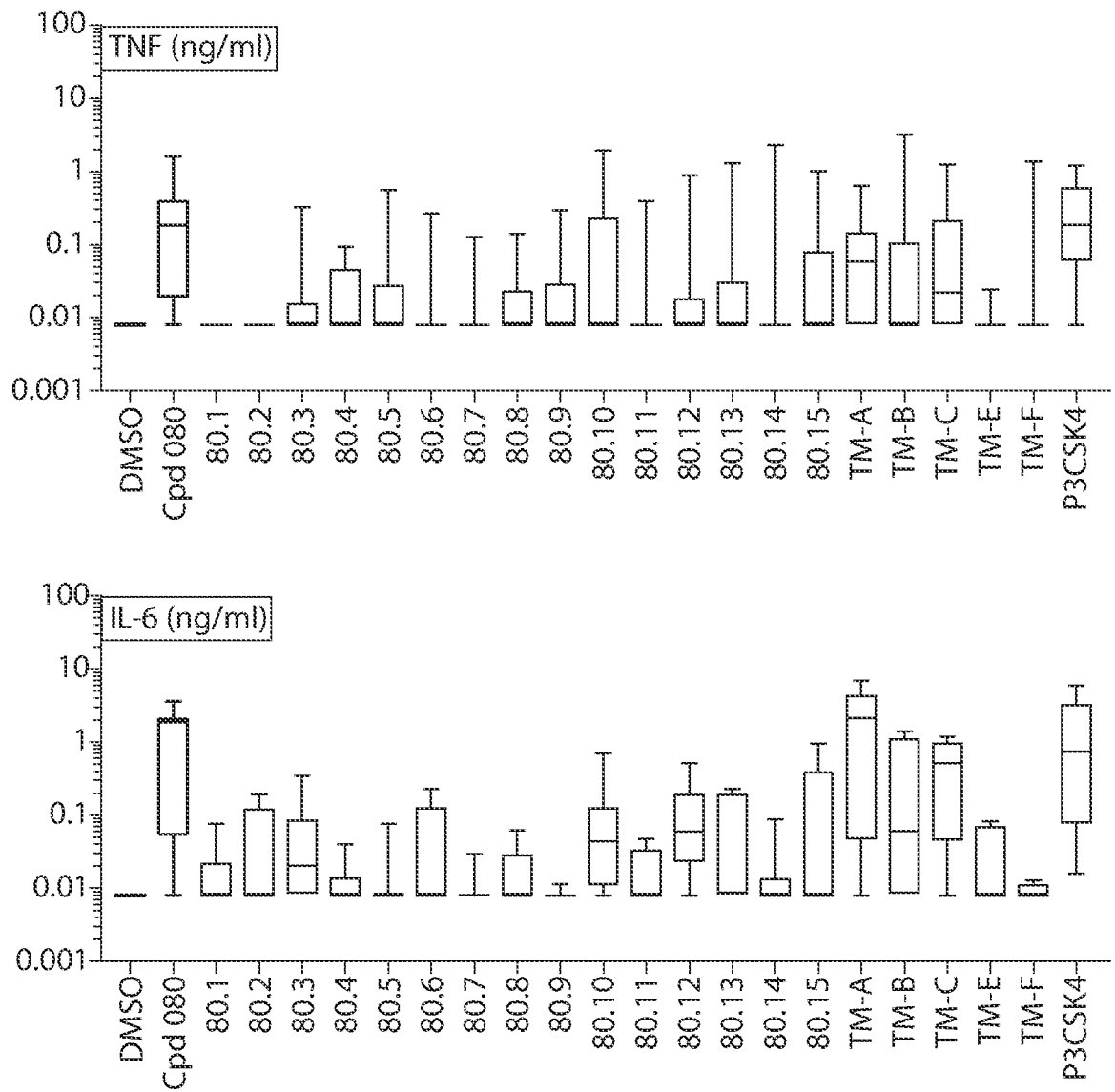
FIG. 7. Compound 080 analog activities in inducing cytokine production by human adults PBMCs. Human adult PBMCs were stimulated in vitro for 24 hours with compound 080, its analogs (80.1-80.15), published known TLR2 agonists (e.g., the "Tappling molecules (TM)" in Guan et al J Biol Chem 2010; 285:23755-23762), including TM-A, TM-B, TM-C, TM-E and TM-F, at 100 UM and the TLR2 agonist P3CSK4 at 1 μg/ml. TNF and IL-6 levels were assessed in cell-free supernatants by ELISA. Results are shown as the median, the 25th and 75th percentiles (boxes) and the 5th and 95th percentiles (whiskers) of TNF (N=13) and IL-6 (N=7).
Figure 9:
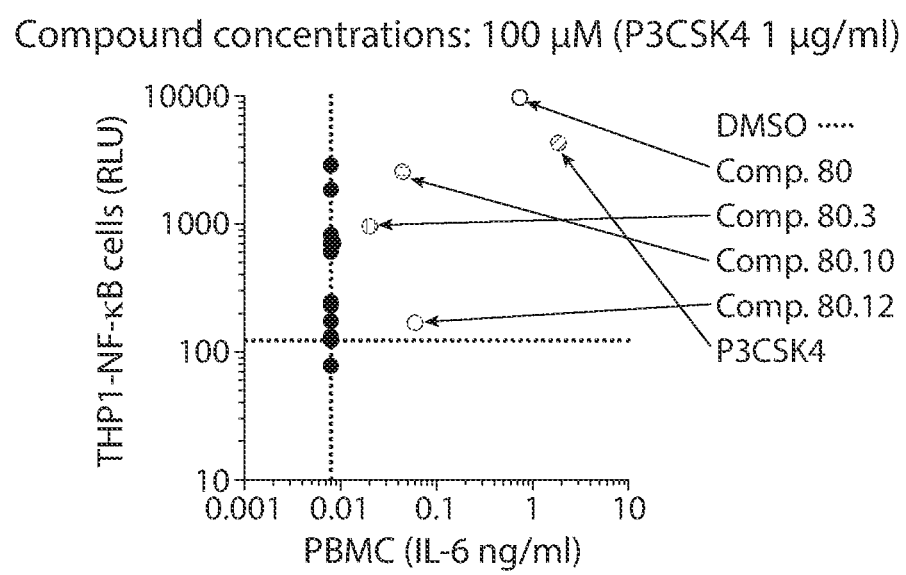
FIG. 9. Correlation between compound 080 family activities on human adult PBMCs and THP1-NF-κB cells. The figure depicts a scatter plot representing the activities on each compound at the indicated concentrations on THP1-NF-κB cells (quantified as luminescence from the secreted luciferase enzyme in cell-free supernatants) and on human adult PBMCs (quantified as IL-6 levels in cell-free supernatants) tested in vitro. Each dot represents median IL-6 (N=7) and luminescence (N=4) levels elicited by a single compound. Compounds whose median activities are above DMSO levels (depicted as dashed lines) are labelled. Other compounds, with undetectable IL-6 inducing activity towards PBMCs, are depicted in black.
Figure 10:
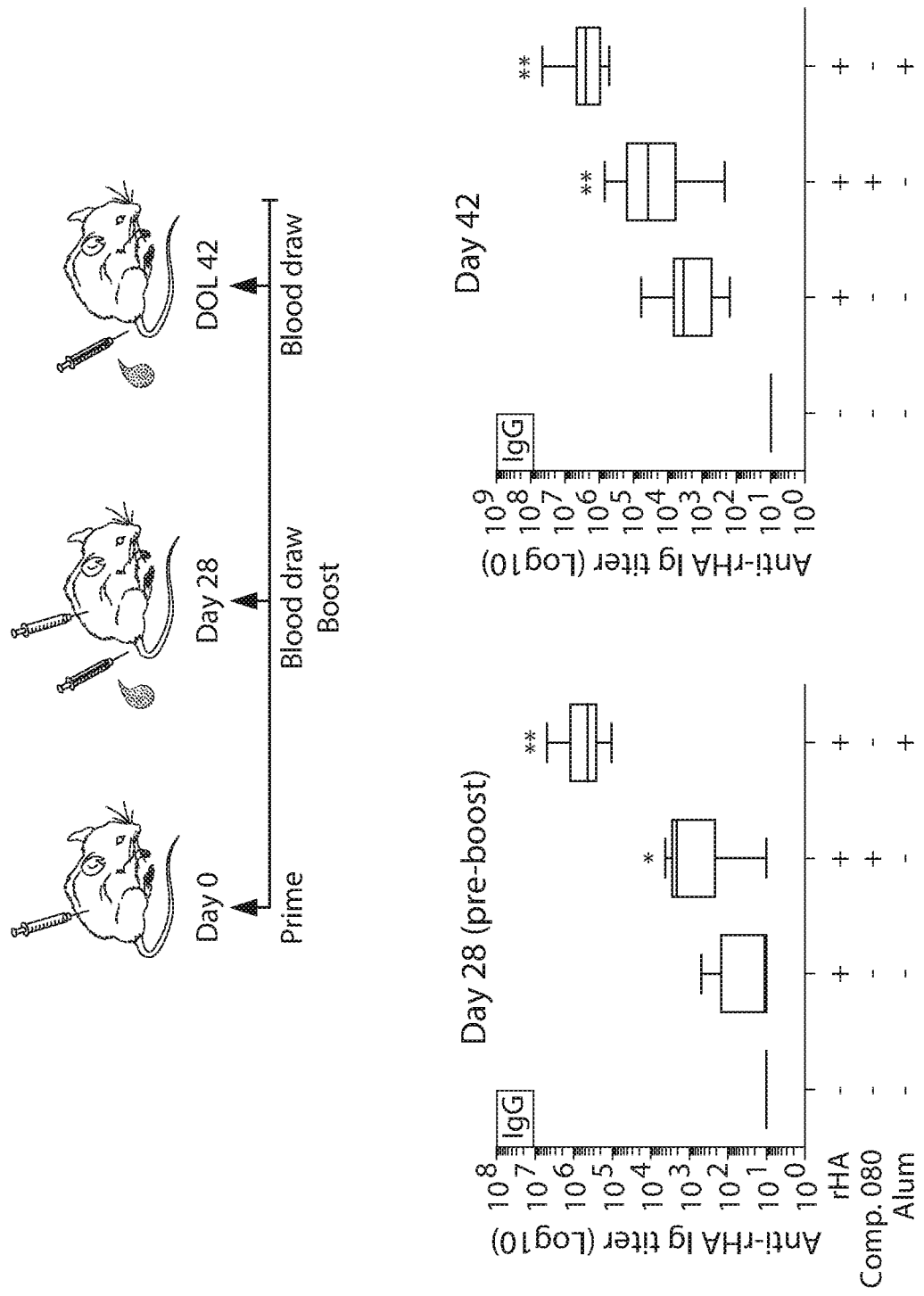
FIG. 10. Compound 080 exerts adjuvant activity in vivo. 6-8 week old C57BL/6 mice were immunized on Day 0 (prime) and at Day 28 (boost) with recombinant hemagglutinin (rHA) alone or formulated with compound 080 or alum. Serum samples were collected at Day 28 (pre-boost) and Day 42 (14 post-boost) and anti-rHA IgG titers were assessed by ELISA. Results are shown as the median, the 25th and 75th percentiles (boxes) and the 5th and 95th percentiles (whiskers) of 10 mice per group. *$p<0.05$ and **$p<0.01$ determined by Kruskal-Wallis with Dunn's multiple comparison test.
Figure 11A:
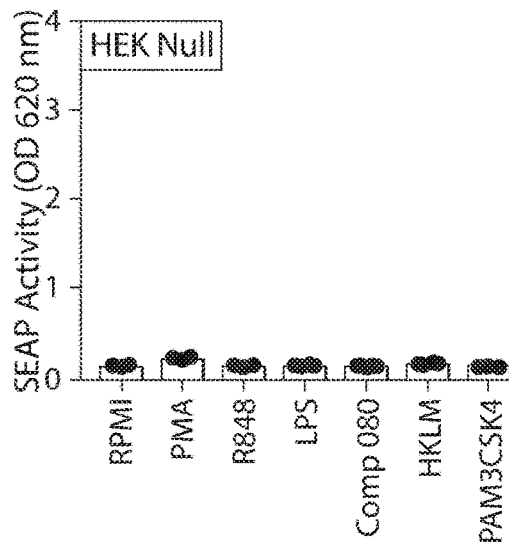
FIGS. 11A-11E. 080 and associated thiophene pharmacophores activates human TLR2 in a receptor specific and titratable fashion. Human Human Embryonic Kidney (HEK) HEK-293 null cells (FIG. 11A) and transfected human HEK TLR2 cell lines (FIG. 11B) (with a NF-kB-driven reporter SEAP gene) were stimulated for 18-24 hours with the mitogen PMA, known TLR agonists, human TNF and the thiophene pharmacophore. The y-axis shows the level of SEAP activity in the Quanti-blue assay optical density (OD) at 650 nm. The x-axis shows the mean, SD and each of 8 replicates of each treatment.
Figure 11B:
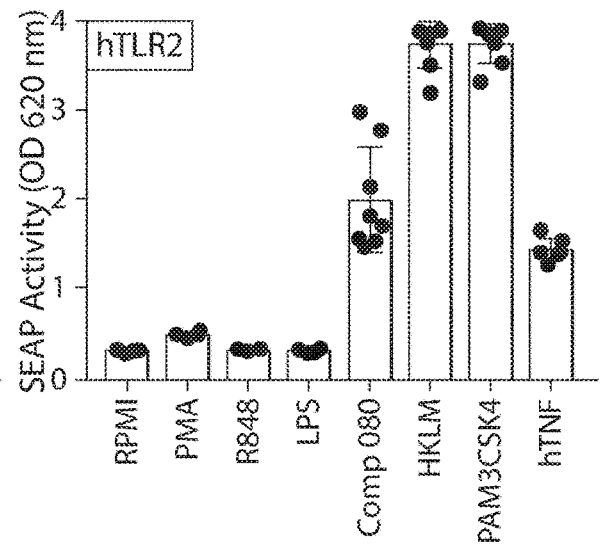
Figure 11C:
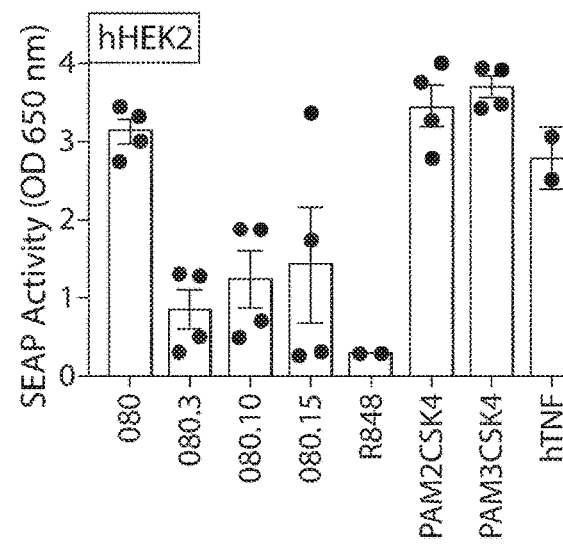
Figure 11D:
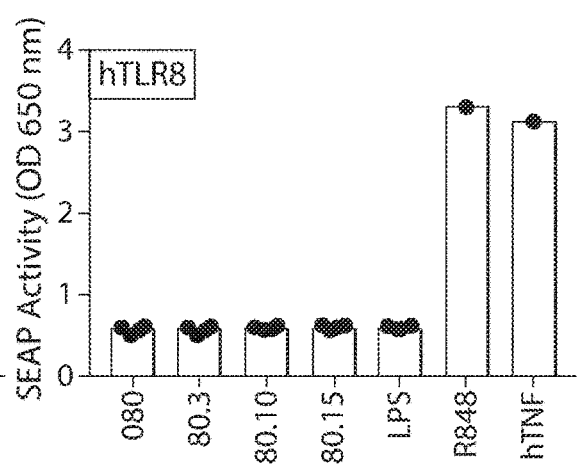
Figure 11E:
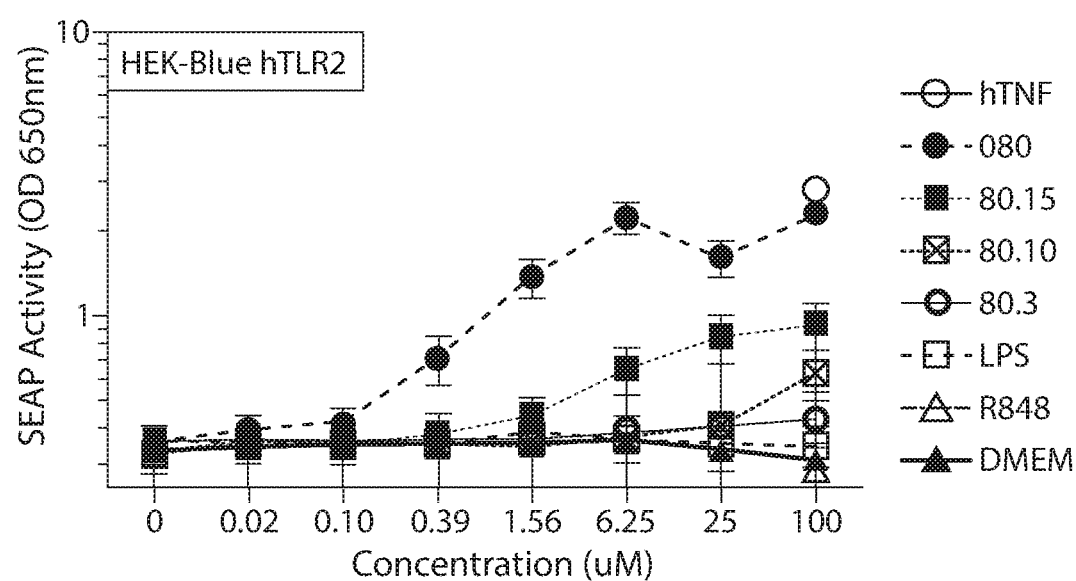

These results were confirmed in a more conventional 384 and 96 well assay, wherein compounds 004 (FIGS. 4A-5) and 080 (FIGS. 6-9) induced activation of THP1 cells and human adult PBMCs. Interestingly, compounds 004 and 080 activated the human TLR2-expressing human embryonic kidney (HEK)-Blue cell line, therefore qualifying them as TLR2 agonists (FIG. 3). In vivo studies in a murine model of immunization with the recombinant influenza vaccine indicate that the addition of compound 080 enhances vaccine responses of adult mice. Mice vaccinated with recombinant Influenza Hemagglutinin (rHA)+080 demonstrated higher antibody titers compared to mice vaccinated with rHA (FIG. 10).

In summary, small molecules with immunomodulatory activity were identified, which activate the NF-κB reporter THP1 cell line and human adult leukocytes in vitro at least one of which acts as an adjuvant that enhances immunogenicity of a vaccinal antigen in mice in vivo.

1) Compounds 004 and 080 were the most effective NF-kB activators in THP1 cells from ~200,000 tested.
2) Compound 080 demonstrates in vivo adjuvanticity.

Materials and Methods

Overview. To identify immunomodulators/adjuvants that robustly activate human immune cells, screening of ~200,000 small molecules tested against THP1 cells was conducted.

THP-1 Cell Line and Culture Conditions. The THP1-Lucia™ cell line was obtained from Invivogen (San Diego, CA). THP1-Lucia cells, which are human monocytic cells derived from the blood of a boy with leukemia, contain an NF-kB-inducible Luc reporter construct. This allows NF-kB activation to be measured by quantifying the luminescence from the secreted luciferase enzyme. THP1-Lucia cells were cultured in RPMI 1640 supplemented with 10% non-heat inactivated fetal bovine serum (FBS), 10 mM HEPES, 1.0 mM sodium pyruvate, 50 ug/ml Pen-Strep, and 100 ug/mL Normocin™. Once cultured, the cells were stored in a 37° C. incubator with 5% $CO_2$ and a humidified atmosphere. Cells were passaged every 2-3 days and not allowed to exceed a concentration of $2.0 \times 10^6$ cells/ml media.

Chemical Libraries. The chemical libraries screened included known bioactive and commercial libraries from various sources (e.g., commercial libraries such as ChemDiv, ChemBridge, and Asinex; see attached pdf of all libraries). All libraries were owned and provided by the Institute of Chemistry and Cell Biology (ICCB)-Longwood (Harvard Medical School).

NF-kB-induced Luminescence Assay. THP1-Lucia cells between passage 15 and 18 and suspended in culture medium were dispensed into 384-well black clear-bottom plates (Corning 3712) at 30,000 cells/30 μl/well using a Combi liquid dispenser. To allow comparison to a benchmark small molecule with known immune stimulating activity, cells at the same concentration were stimulated with 50 μM R848, a TLR7/8 agonist, in 0.3% DMSO and added to every other well of column 24, which was left empty of cells, by multichannel pipette at the same volume. Five μl of 700 nM Phorbol myristate acetate (PMA) in THP1 culture media and 2.3% DMSO, a known peripheral blood cell mitogen, was added to every other well of column 23 by multichannel pipette (final concentration in well: 100 nM in 0.3% DMSO). Five μl of THP1 culture media with 2.3% DMSO was added to the remaining wells of column 23 by multichannel pipette (final concentration 0.3% DMSO). One hundred nl aliquots of library compounds diluted in 100% DMSO were transferred from their original 384-well plates to the assay plates using a Seiko pin transfer machine. Each library plate was pinned in duplicate, yielding two assay plates with identical conditions for comparison. Plates were then incubated for 24 hours at 37 C with 5% $CO_2$ in humid conditions. Following incubation, 10 μL of supernatant was removed from each well and transferred to a white plate (Corning 3570) using a Vprep liquid transfer machine. 10 μL of recombinant Lucia protein (Invivogen) diluted 1:2000 in THP1 culture media was added to empty well 24P. Using a Combi liquid dispenser, 50 μL/well of Quanti-Luc substrate (Invivogen) diluted 1:3 in sterile water was added to the assay plate. Immediately after adding the substrate, the luminescence was read using a PerkinElmer Envision plate reader.

THP1 Cell Adherence Assay. Following incubation and supernatant transfer described above, each black assay plate was manually washed. First, remaining suspension cells were expelled into a bath of 15% bleach by shaking the plate upside down. The plate was then submerged in a 7 L bath of 1×PBS. Once submerged, each plate was shaken vigorously side-to-side to release any air bubbles forming in the wells. The plate was then removed and shaken into the bleach bath once again. This process was repeated 3 times per plate. 30 μL/well of a mix of 2 μg/ml. Hoechst 33342 in PBS with 1% Para-formaldehyde was added using a Combi liquid dispenser to the washed assay plates. Plates were left in the dark to stain and fix for 20 minutes. Washed and stained assay plates were then loaded onto an Acumen laser scanning cytometer. Total fluorescence area and number of objects (nuclei) were measured using the instrument for each well.

Hit Calling Method. Test compounds that resulted in a robust Z score>2 in both duplicates and at ≥2 of the 3 human samples of PBMCs were considered hits. The following hit calling standard operating procedure (SOP) was used for the THP-1 screen:

All Data is log 10-transformed (log 10)—CrossTalk Corrected luminescence data from columns E, and F is log-transformed (log 10) in columns K, and L. Only experimental wells are evaluated, referencing column C with an "if" logic statement. An example of the calculation in column Q, log-transforming data from column E, is shown below:

=IF($C2$="$X$",LOG 10($E2$)," ")

A robust Z score is calculated for each experimental well with adjusted median absolute deviation (MAD) values. First, the plate median and MAD values are generated from the log-transformed data. The absolute deviation for each well value is calculated in columns M and N, an example of which is shown below:

=IF($C2$="$X$",ABS($K2$-$I$3)," ")

wherein K2 is a log transformed data point, and I3 is the median value for that plate for that readout.

The MAD is then calculated as the median of each of columns U-X multiplied by 1.4286, an example of which is shown below:

=MEDIAN($M2:M385$)*1.4286

The robust Z score is then calculated as (well_value−median_plate)/(MAD_plate*1.4286), an example calculation is shown below:

=IF($C2$="$X$",(($K2$-$I$3)/$I$5)," ")

wherein K2 is a log-transformed well value, I3 is the plate experimental median for that readout, and I5 is the plate experimental MAD for that readout.

Any wells with robust Z score values of 2 or greater in both replicates are considered a hit. This is evaluated in column Q as shown in the example below:

=IF(AND(($O2$>$I$7),($P2$>$J$7),($C2$="$X$")),TRUE, FALSE)

wherein O2 and P2 are robust Z scores for replicates of the luminescence readout, while I7 and J7 represent the luminescence robust Z score threshold (2). "TRUE" will be returned in column Q if the compound meets these hit criteria.

For any well that is determined to be a hit, the Plate: Well compound ID will be displayed in column R as shown in the example below:

=IF($Q2$,CONCATENATE($A2$,":",$B2$)," ")

in which Q2 is the TRUE/FALSE value determining the hit status of the compound while A2 is the plate ID and B2 is the well ID.

HEK cell screening. Human embryonic kidney (HEK)-Blue cell lines expressing human TLRs (hTLRs) and a secreted embryonic alkaline phosphatase (SEAP) reporter under the control of an NF-κB-inducible promoter were cultured in 96-well plates (50,000-75,000 cells/200 μl/well) and stimulated with the indicated compounds at 10 UM or positive controls. The media added to the wells is designed for detection of NF-κB-induced SEAP expression. After 16-24 hours of incubation optical density (OD) was read at 650 nm on a Molecular Devices SpectraMax 340PC absorbance detector. Positive controls employed in this assay were: heat-killed *Listeria monocytogenes* ($1 \times 10^8$ cells/ml) for hTLR2, Poly (I:C) HMW (1 μg/ml) for hTLR3, *E. coli* K12 LPS (100 ng/ml) for hTLR4, *S. typhimurium* flagellin (100 ng/ml) for hTLR5, CL307 (1 μg/ml) for hTLR7, CL075 (1 μg/ml) for hTLR8 and CpG ODN 2006 (1 μg/ml) for hTLR9.

ELISAs and Multiplex-Analyte Assays. Supernatants derived from human PBMCs stimulations were assayed by ELISA for TNF and IL-6 (ThermoFisher Scientific; Waltham, MA, USA). Cytokine and chemokine expression profiles (e.g., IFNγ, IL-9, IL-10, IL-12 (p70), IL-13, IL-1β, IL-23, IL-27, IL-28A, IL-33, IL-6, MIP-3α/CCL20, and TNF) in cell culture supernatants were measured using a customized Milliplex® Human Th17 Magnetic Bead Panel according to the manufacturer's instructions (Millipore, Chicago, IL, USA). Assays were read and analyzed on the Luminex® 100/200TM System and xPOTENT® software (Luminex, Austin, TX). A minimum threshold was set at the minimum detectable concentration for each individual assay, defined as three standard deviations above the mean background.

In Vitro PBMC and Stimulation.

PBMCs were isolated from blood using a Ficoll density gradient. PBMCs either used fresh or were stored at $5 \times 10^7$ cells per vial in 1 mL RPMI containing 20% autologous plasma and 10% DMSO at −80° C. until use. Stimulation plates were prepared by transferring 0.66 μl of DMSO-dissolved compounds (30 or 7.5 mM) to each well of a round bottom 96-well plate. PBMCs isolated from human adult donors or THP1-NF-κB cells were resuspended at a concentration of $10^5$ cells/200 μl of RPMI supplemented with 10% of platelet-poor plasma or THP1 culture medium, respectively. 200 μl of the cell suspension were transferred to each well resulting in a final compound concentration of 100 or 25 μM. After 24 hours of incubation (37° C., 5% $CO_2$), plates were spun down (500×g, room temperature, 5 minutes) and supernatants were harvested for further analysis.

Animals

C57BL/6 mice were obtained from Charles River Laboratories and housed in specific pathogen-free conditions in the animal research facilities at Boston Children's Hospital.

Antigens, Immunization and Antibody Quantification

For immunization experiments, adult mice were immunized intramuscularly (i.m.) in the right posterior thigh with 50 μl of vaccine containing 0.33 μg of each of the following recombinant influenza virus hemagglutinins (rHA): A/Michigan/45/2015 (H1N1), A/Hong Kong/4801/2014 (H3N2), and B/Brisbane/60/2008, contained in the 2016-2017 formulation of the FluBlok vaccine (Protein Sciences Corp.). Mice were immunized with a prime-boost schedule (two injections four weeks apart). Vaccine in all experimental groups was formulated with 10% (v/v) DMSO (except for the groups immunized with the small molecules since they were dissolved in DMSO) and 5% (v/v) Tween-80. As indicated for specific experimental groups, vaccine was also formulated with Aluminium hydroxide (100 μg) or compound 080 (100 nmol, final DMSO concentration 10%).

Serum was collected 28 days post-prime (pre-boost blood sample) and 14 days post-boost for antibody detection. rHA-specific IgG were quantified by ELISA. High binding flat bottom 96-well plates (Corning Life Sciences) were coated with 1 µg/ml rHA in carbonate buffer pH 9.6, incubated overnight at 4° C. and blocked with PBS+BSA 1% (Sigma-Aldrich) for 1 h at room temperature (RT). Then, sera from vaccinated mice were added with an initial dilution of 1:100 and 1:4 serial dilutions in PBS+BSA 1% and incubated for 2 hrs at RT. Plates were then washed and incubated for 1 hr at RT with HRP-conjugated anti-mouse IgG (Southern Biotech). At the end of the incubation plates were washed again and developed with tetramethylbenzidine (BD Biosciences) for 5 minutes, then stopped with 1 N $H_2SO_4$. The optical density was read at 450 nm Versamax microplate reader with SoftMax Pro Version 5 (both from Molecular Devices) and endpoint titers were calculated using as cutoff three times the optical density of the background.

Statistical analysis. Statistical significance and graphic output were generated using Prism v. 5.0b (GraphPad Software) Results were considered significant at p values<0.05, and indicated as follows: *p<0.05, **p<0.01.

HEK293 assay for human TLR2 and TLR8 selectivity: Human embryonic kidney (HEK) 293 cells expressing human TLR2 or TLR8 with an NF-κB-responsive secreted embryonic alkaline phosphatase (SEAP) reporter gene were obtained from Invivogen (San Diego, CA). Cells were maintained in RPMI or DMEM with 10% heat inactivated-FBS and selection antibiotics per the manufacturer's instructions. Cells were plated at $5 \times 10^5$ cells/96-well and stimulated with indicated agonist(s) for 24 hours. Supernatants were harvested and analyzed for NF-κB/SEAP activation using the QuantiBlue kit (Invivogen). Values are expressed as fold change in $OD_{650}$ over vehicle-only treated samples.

Example 2. Structure Activity Relationship Analysis of Compounds

TABLE 3

Activity of Exemplary Compounds (Compound 080 series molecules) in Stimulating TNF-α and IL-6 Production from human adult PBMCs or NF-κB-dependent luminescence in THP1 cells.

| Molecule | Structure | Adult PBMCs (median ng/ml) | | THP1 cells (relative luminescence units, N = 4) | |
| --- | --- | --- | --- | --- | --- |
| | | TNFa (N = 13) | IL-6 (N = 7) | Comp at 100 uM | Comp at 25 uM |
| 80 | | 0.1958 | 1.868 | 12174 | 8280 |
| 80.3 | | 0.008 | 0.008 | 3630 | 2835 |
| 80.5 | | 0.008 | 0.008 | 777 | 436.5 |
| 80.6 | | 0 008 | 0 008 | 2816 | 2505 |

TABLE 3-continued

Activity of Exemplary Compounds (Compound 080 series molecules) in Stimulating
TNF-α and IL-6 Production from human adult PBMCs or NF-κB-dependent luminescence in
THP1 cells.

| Molecule | Structure | Adult PBMCs (median ng/ml) | | THP1 cells (relative luminescence units, N = 4) | |
|---|---|---|---|---|---|
| | | TNFa (N = 13) | IL-6 (N = 7) | Comp at 100 uM | Comp at 25 uM |
| 80.8 | 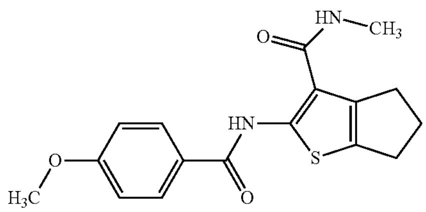 [SMILES: CNC(=O)c1c(NC(=O)c2ccc(OC)cc2)sc2c1CCC2] | 0.008 | 0.008 | 2552 | 258.5 |
| 80.10 | 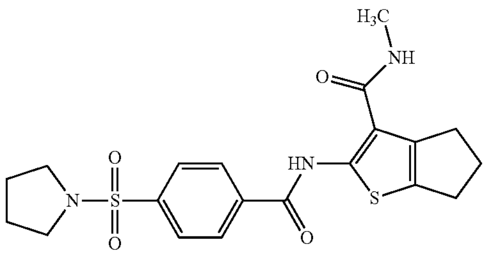 [SMILES: CNC(=O)c1c(NC(=O)c2ccc(S(=O)(=O)N3CCCC3)cc2)sc2c1CCC2] | 0.008 | 0.012 | 4814 | 3576 |
| 80.11 | 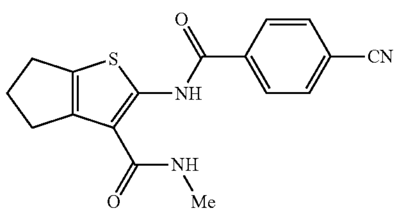 [SMILES: CNC(=O)c1c(NC(=O)c2ccc(C#N)cc2)sc2c1CCC2] | 0.008 | 0.0225 | 2420 | 1108 |
| 80.13 | 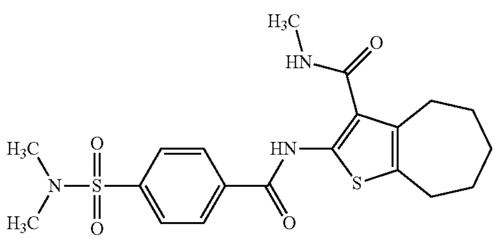 [SMILES: CNC(=O)c1c(NC(=O)c2ccc(S(=O)(=O)N(C)C)cc2)sc2c1CCCCC2] | 0.008 | 0.008 | 11361 | 348 |
| 80.14 | 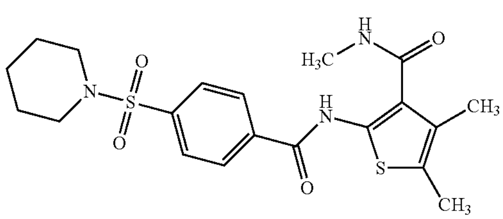 [SMILES: CNC(=O)c1c(NC(=O)c2ccc(S(=O)(=O)N3CCCCC3)cc2)sc(C)c1C] | 0.008 | 0.008 | 1475 | 517 |
| 80.15 | 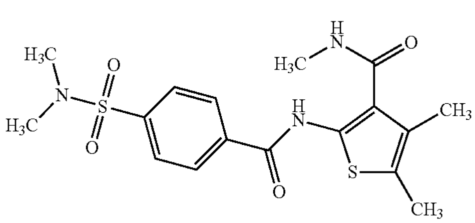 | 0.0225 | 0.008 | 9715 | 6369 |

TABLE 3-continued

Activity of Exemplary Compounds (Compound 080 series molecules) in Stimulating TNF-α and IL-6 Production from human adult PBMCs or NF-κB-dependent luminescence in THP1 cells.

| Molecule | Structure | Adult PBMCs (median ng/ml) | | THP1 cells (relative luminescence units, N = 4) | |
|---|---|---|---|---|---|
| | | TNFa (N = 13) | IL-6 (N = 7) | Comp at 100 uM | Comp at 25 uM |
| TM-A | | 0.092 | 2.154 | 13092 | 8777 |
| TM-B | | 0.008 | 0.057 | 681 | 1204 |
| TM-C | | 0.01575 | 0.5145 | 4031 | 3440 |
| TM-E | | 0.008 | 0.008 | 428.5 | 320 |

TABLE 3-continued

Activity of Exemplary Compounds (Compound 080 series molecules) in Stimulating
TNF-α and IL-6 Production from human adult PBMCs or NF-κB-dependent luminescence in
THP1 cells.

| Molecule | Structure | Adult PBMCs (median ng/ml) | | THP1 cells (relative luminescence units, N = 4) | |
|---|---|---|---|---|---|
| | | TNFa (N = 13) | IL-6 (N = 7) | Comp at 100 uM | Comp at 25 uM |
| TM-F | [structure] | 0.008 | 0.008 | 2012 | 348.5 |
| Vehicle control | | 0.008 | 0.008 | 333.5 | 220.5 |

All publications, patents, patent applications, publication, and database entries (e.g., sequence database entries) mentioned herein, e.g., in the Background, Summary, Detailed Description, Examples, and/or References sections, are hereby incorporated by reference in their entirety as if each individual publication, patent, patent application, publication, and database entry was specifically and individually incorporated herein by reference. In case of conflict, the present application, including any definitions herein, will control.

EQUIVALENTS AND SCOPE

Those skilled in the art will recognize, or be able to ascertain using no more than routine experimentation, many equivalents of the embodiments described herein. The scope of the present disclosure is not intended to be limited to the above description, but rather is as set forth in the appended claims.

Articles such as "a," "an," and "the" may mean one or more than one unless indicated to the contrary or otherwise evident from the context. Claims or descriptions that include "or" between two or more members of a group are considered satisfied if one, more than one, or all of the group members are present, unless indicated to the contrary or otherwise evident from the context. The disclosure of a group that includes "or" between two or more group members provides embodiments in which exactly one member of the group is present, embodiments in which more than one members of the group are present, and embodiments in which all of the group members are present. For purposes of brevity those embodiments have not been individually spelled out herein, but it will be understood that each of these embodiments is provided herein and may be specifically claimed or disclaimed.

It is to be understood that the disclosure encompasses all variations, combinations, and permutations in which one or more limitation, element, clause, or descriptive term, from one or more of the claims or from one or more relevant portion of the description, is introduced into another claim. For example, a claim that is dependent on another claim can be modified to include one or more of the limitations found in any other claim that is dependent on the same base claim. Furthermore, where the claims recite a composition, it is to be understood that methods of making or using the composition according to any of the methods of making or using disclosed herein or according to methods known in the art, if any, are included, unless otherwise indicated or unless it would be evident to one of ordinary skill in the art that a contradiction or inconsistency would arise.

Where elements are presented as lists, e.g., in Markush group format, it is to be understood that every possible subgroup of the elements is also disclosed, and that any element or subgroup of elements can be removed from the group. It is also noted that the term "comprising" is intended to be open and permits the inclusion of additional elements or steps. It should be understood that, in general, where an embodiment, product, or method is referred to as comprising particular elements, features, or steps, embodiments, products, or methods that consist, or consist essentially of, such elements, features, or steps, are provided as well. For purposes of brevity those embodiments have not been individually spelled out herein, but it will be understood that each of these embodiments is provided herein and may be specifically claimed or disclaimed.

Where ranges are given, endpoints are included. Furthermore, it is to be understood that unless otherwise indicated or otherwise evident from the context and/or the understanding of one of ordinary skill in the art, values that are expressed as ranges can assume any specific value within the stated ranges in some embodiments, to the tenth of the unit of the lower limit of the range, unless the context clearly dictates otherwise. For purposes of brevity, the values in each range have not been individually spelled out herein, but it will be understood that each of these values is provided herein and may be specifically claimed or disclaimed. It is also to be understood that unless otherwise indicated or otherwise evident from the context and/or the understanding of one of ordinary skill in the art, values expressed as ranges can assume any subrange within the given range, wherein the endpoints of the subrange are expressed to the same degree of accuracy as the tenth of the unit of the lower limit of the range.

Where websites are provided, URL addresses are provided as non-browser-executable codes, with periods of the respective web address in parentheses. The actual web addresses do not contain the parentheses.

In addition, it is to be understood that any particular embodiment of the present disclosure may be explicitly excluded from any one or more of the claims. Where ranges are given, any value within the range may explicitly be excluded from any one or more of the claims. Any embodiment, element, feature, application, or aspect of the compositions and/or methods of the disclosure, can be excluded from any one or more claims. For purposes of brevity, all of the embodiments in which one or more elements, features, purposes, or aspects is excluded are not set forth explicitly herein.

What is claimed is:

1. A composition comprising an antigen and a Toll-like receptor 2 (TLR2) agonist, wherein the TLR2 agonist is a compound of Formula (I):

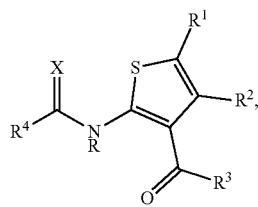

or a pharmaceutically acceptable salt thereof, wherein:
  $R^1$ is hydrogen or optionally substituted alkyl;
  $R^2$ is hydrogen or optionally substituted alkyl; or $R^1$ and $R^2$ are joined together with the intervening atoms to form a substituted or unsubstituted carbocyclic ring, substituted or unsubstituted heterocyclic ring, or substituted or unsubstituted heteroaryl ring;
  $R^3$ is hydrogen, halogen, optionally substituted alkyl, —$OR^{a1}$, or —$N(R^{a2})_2$, wherein $R^{a1}$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group when attached to an oxygen atom;
  wherein each occurrence of $R^{a2}$ is independently hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group;
  R is hydrogen or optionally substituted alkyl;
  X is O or S; and
  $R^4$ is hydrogen, optionally substituted heterocyclyl, or optionally substituted aryl.

2. The composition of claim 1, wherein the antigen comprises a protein or polypeptide.

3. The composition of claim 1, wherein the antigen comprises a nucleic acid encoding a protein or a polypeptide.

4. The composition of claim 1, wherein the antigen is from a microbial pathogen.

5. The composition of claim 1, wherein the antigen is a cancer-specific antigen.

6. The composition of claim 1, wherein the composition is a vaccine composition and the TLR2 agonist is an adjuvant.

7. The composition of claim 1, wherein the compound is of Formula (IA):

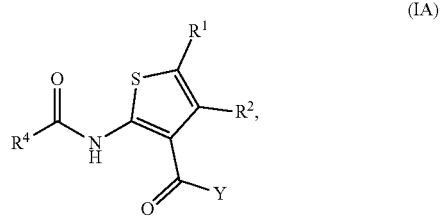

or a pharmaceutically acceptable salt thereof, wherein:
  $R^1$ and $R^2$ are joined together with the intervening atoms to form a substituted or unsubstituted carbocyclic ring, substituted or unsubstituted heterocyclic ring, or substituted or unsubstituted heteroaryl ring;
  Y is —$OR^{a1}$, or —$N(R^{a2})_2$, wherein $R^{a1}$ is optionally substituted $C_{1-6}$ alkyl; and each occurrence of $R^{a2}$ is independently hydrogen or optionally substituted $C_{1-6}$ alkyl.

8. A method of enhancing an immune response to an antigen in a subject in need thereof, the method comprising administering to the subject the composition of claim 1.

9. The method of claim 8, wherein the administration is prophylactic.

10. The method of claim 8, wherein the subject is a human neonate, an infant, an adult, or an elderly.

11. The method of claim 10, wherein the infant is less than 28 days of age at the time of administration.

12. A method of vaccinating a subject in need thereof, the method comprising administering to the subject an effective amount of the composition of claim 1.

13. The composition of claim 7, wherein $R^1$ and $R^2$ are joined together with the intervening atoms to form a 5-membered carbocyclic ring, 6-membered carbocyclic ring, or 7-membered carbocyclic ring.

14. The composition of claim 7, wherein the compound is of formula:

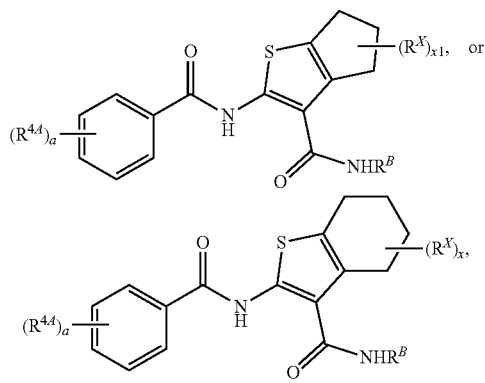

or a pharmaceutically acceptable salt thereof, wherein:

$R^{4A}$ is halogen, optionally substituted alkyl, optionally substituted acyl, —CN, —SO₂N(R$^a$)₂, —OR$^b$, optionally substituted alkenyl, optionally substituted alkynyl, optionally substituted carbocyclyl, optionally substituted heterocyclyl, optionally substituted aryl, or optionally substituted heteroaryl;

each instance of $R^X$ is independently hydrogen, halogen, or optionally substituted alkyl;

$R^B$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, or optionally substituted heteroaryl;

x is 0, 1, 2, 3, 4, 5, or 6;

x1 is 0, 1, 2, 3, 4, 5, or 6;

a is 0, 1, 2, 3, 4, or 5;

each instance of $R^a$ is independently hydrogen, optionally substituted alkyl, a nitrogen protecting group, or two instances of $R^a$ are joined together with the intervening atoms to form optionally substituted heterocyclyl; and $R^b$ is hydrogen, optionally substituted alkyl, or an oxygen protecting group.

15. The composition of claim 14, wherein the compound is of formula:

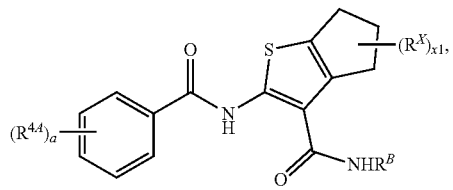

or a pharmaceutically acceptable salt thereof.

16. The composition of claim 15, wherein at least one instance of $R^{4A}$ is halogen, —CN, or —SO₂N(R$^a$)₂, wherein each instance of $R^a$ is independently optionally substituted alkyl, or two instances of $R^a$ are joined together with the intervening atoms to form an optionally substituted heterocyclyl.

17. The composition of claim 15, wherein a is 1; and $R^{4A}$ is —SO₂N(R$^a$)₂, wherein each instance of $R^a$ is independently optionally substituted alkyl, or two instances of $R^a$ are joined together with the intervening atoms to form an optionally substituted heterocyclyl.

18. The composition of claim 1, wherein the compound is of formula:

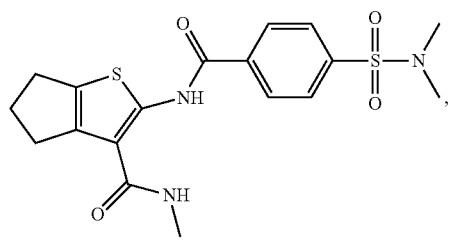

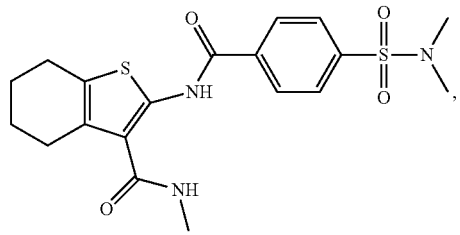

(80.3)

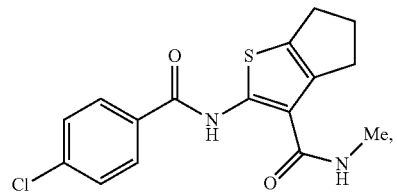

(80.5)

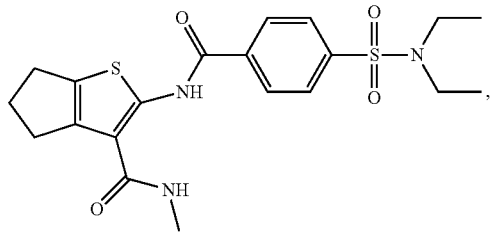

(80.6)

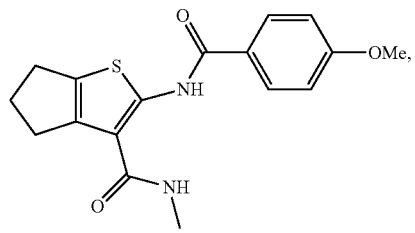

(80.8)

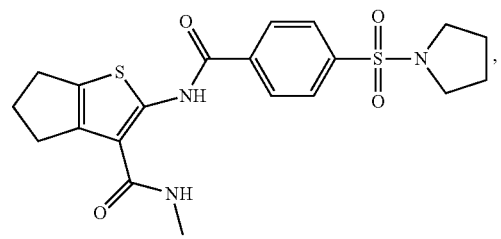

(80.10)

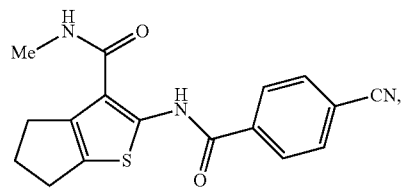

(80.11)

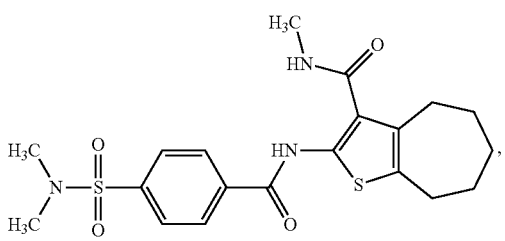

(80.13)

(80.14)
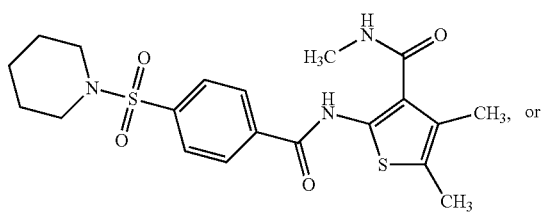
(80.15)
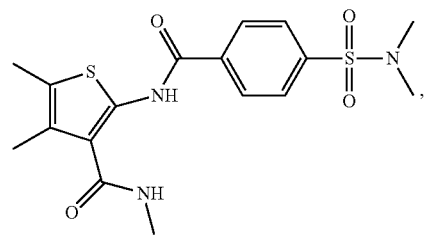
(TM-B)
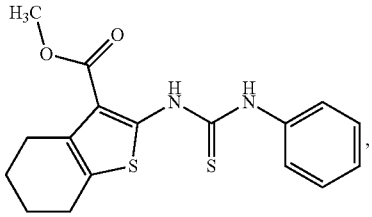
(TM-C)
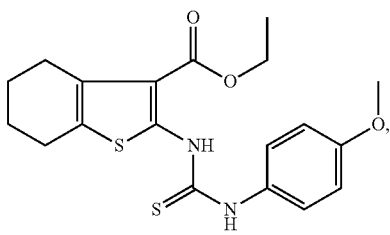
or a pharmaceutically acceptable salt thereof.
* * * * *